(12) United States Patent
Vavvas et al.

(10) Patent No.: US 9,492,432 B2
(45) Date of Patent: Nov. 15, 2016

(54) METHODS AND COMPOSITIONS FOR PRESERVING PHOTORECEPTOR AND RETINAL PIGMENT EPITHELIAL CELLS

(71) Applicant: Massachusetts Eye and Ear Infirmary, Boston, MA (US)

(72) Inventors: Demetrios Vavvas, Boston, MA (US); Georgios Trichonas, Boston, MA (US); Joan W. Miller, Winchester, MA (US); Yusuke Murakami, Newton, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 14/934,810

(22) Filed: Nov. 6, 2015

(65) Prior Publication Data
US 2016/0250189 A1 Sep. 1, 2016

Related U.S. Application Data

(63) Continuation of application No. 13/642,887, filed as application No. PCT/US2011/033704 on Apr. 23, 2011, now abandoned.

(60) Provisional application No. 61/472,153, filed on Apr. 5, 2011, provisional application No. 61/472,144, filed on Apr. 5, 2011, provisional application No. 61/414,862, filed on Nov. 17, 2010, provisional application No. 61/409,055, filed on Nov. 1, 2010, provisional application No. 61/405,003, filed on Oct. 20, 2010, provisional application No. 61/327,476, filed on Apr. 23, 2010.

(51) Int. Cl.
| | | |
|---|---|---|
| A61K 31/40 | (2006.01) | |
| A61K 31/4178 | (2006.01) | |
| A61K 38/00 | (2006.01) | |
| A61K 38/05 | (2006.01) | |
| A61K 38/55 | (2006.01) | |
| A61K 9/00 | (2006.01) | |
| A61K 38/06 | (2006.01) | |

(52) U.S. Cl.
CPC ........ *A61K 31/4178* (2013.01); *A61K 9/0048* (2013.01); *A61K 31/40* (2013.01); *A61K 38/005* (2013.01); *A61K 38/05* (2013.01); *A61K 38/06* (2013.01)

(58) Field of Classification Search
None
See application file for complete search history.

(56) References Cited

U.S. PATENT DOCUMENTS

| | | |
|---|---|---|
| 5,443,505 A | 8/1995 | Wong et al. |
| 5,766,242 A | 6/1998 | Wong et al. |
| 6,245,523 B1 | 6/2001 | Altieri |
| 6,251,090 B1 | 6/2001 | Avery et al. |
| 6,299,895 B1 | 10/2001 | Hammang et al. |
| 6,375,972 B1 | 4/2002 | Guo et al. |
| 6,413,540 B1 | 7/2002 | Yaacobi |
| 6,416,777 B1 | 7/2002 | Yaacobi |
| 7,622,106 B1 | 11/2009 | Wang et al. |
| 2007/0049565 A1 | 3/2007 | Gwag et al. |
| 2007/0298129 A1 | 12/2007 | Gwag et al. |
| 2009/0099242 A1 | 4/2009 | Cuny et al. |
| 2011/0071088 A1 | 3/2011 | Benowitz |
| 2013/0137642 A1 | 5/2013 | Vavvas et al. |
| 2014/0024598 A1 | 1/2014 | Vavvas et al. |
| 2014/0357570 A1 | 12/2014 | Vavvas |

FOREIGN PATENT DOCUMENTS

| | | |
|---|---|---|
| WO | WO-00/40089 | 7/2000 |
| WO | WO-01/28474 | 4/2001 |
| WO | WO-01/28493 A2 | 4/2001 |
| WO | WO-01/39792 | 6/2001 |
| WO | WO-02/089767 | 11/2002 |
| WO | WO-03/061519 | 7/2003 |
| WO | WO-2005/077344 A2 | 8/2005 |
| WO | WO-2007/071448 A2 | 6/2007 |
| WO | WO-2007/075772 A2 | 7/2007 |
| WO | WO-2008/045406 A2 | 4/2008 |
| WO | WO-2009/023272 A1 | 2/2009 |
| WO | WO-2010/075290 A1 | 7/2010 |
| WO | WO-2011/071088 A1 | 6/2011 |
| WO | WO-2011/133964 A2 | 10/2011 |
| WO | WO-2012/061045 A2 | 5/2012 |
| WO | WO-2013/059791 A2 | 4/2013 |

OTHER PUBLICATIONS

Ambati, et al. (2000) "Transscleral Delivery of Bioactive Protein to the Choroid and Retina," Investigative Opthalmology & Visual Science, 41:1186-1191.

Ambati, et al. (2000) "Diffusion of High Molecular Weight Compounds through Sclera," Investigative Ophthalmology & Visual Science, 41:1181-1185.

Arimura, et al. (2009) "Intraocular Expression and Release of High-mobility Group Box 1 Protein in Retinal Detachment," Laboratory Investigation, 89:278-289.

Arroyo, et al. (2005) "Photoreceptor Apoptosis in Human Retinal Detachment," American Journal of Opthalmology, 139: 605-610.

(Continued)

*Primary Examiner* — Christine J Saoud
*Assistant Examiner* — Jon M Lockard
(74) *Attorney, Agent, or Firm* — Goodwin Procter LLP

(57) ABSTRACT

Provided are methods and compositions for maintaining the viability of photoreceptor cells and/or retinal pigment epithelial cells in a subject with an ocular disorder including, for example, age-related macular degeneration (AMD) (e.g., dry or neovascular AMD), retinitis pigmentosa (RP), or a retinal detachment. The viability of the photoreceptor cells and/or the retinal pigment epithelial cells can be preserved by administering a necrosis inhibitor either alone or in combination with an apoptosis inhibitor to a subject having an eye with the ocular condition. The compositions, when administered, maintain the viability of the cells, thereby minimizing the loss of vision or visual function associated with the ocular disorder.

15 Claims, 36 Drawing Sheets

(56) References Cited

OTHER PUBLICATIONS

Balkwill (2009) "Tumor Necrosis Factor and Cancer," Nature Reviews Cancer, 9(5):361-371.
Barber, et al. (1998) "Neural Apoptosis in the Retina During Experimental and Human Diabetes, Early Onset and Effect of Insulin," Journal of Clinical Investigation, 102:783-791.
Campo, et al. (1999) "Pars Plana Vitrectomy Without Scleral Buckle for Pseudophakic Retinal Detachments," Opthalmology, 106:1811-1815.
Candé, et al. (2004) "Apoptosis-Inducing Factor (AIF): Caspase-Independent After All," Cell Death and Differentiation, 11:591-595.
Cavassani, et al. (2008) "TLR3 is an Endogenous Sensor of Tissue Necrosis During Acute Inflammatory Events," The Journal of Experimental Medicine, 205:2609-2621.
Chan, et al., (2011) "Rescue of Cybids Containing Leber Hereditary Optic Neuropathy (Ihon) Mutation Using Necrostatin-1 and Pancaspase Inhibitor Combination," Annual Meeting of the Association-for-Research-in-Vision-and-Ophthalmology (ARVO), May 1, 2011, (Abstract).
Chang, et al. (2002) "Retinal Degeneration Mutants in the Mouse," Vision Research, 42:517-525.
Chaudhary, et al. (1999) "Caspase Inhibitors Block the Retinal Ganglion Cell Death Following Optic Nerve Transection," Molecular Brain Research, 67:36-45.
Chauvier (2007) "Broad-Spectrum Caspase Inhibitors: From Myth to Reality?," Cell Death and Differentiation, 14,387-391.
Cho, et al. (2009) "Phosphorylation-Driven Assembly of RIP1-RIP3 Complex Regulates Programmed Necrosis and Virus-Induced Inflammation," Cell, 137:1112-1130.
Chua, et al. (2010) "Neuroprotective Agents in Glaucoma Therapy: Recent Developments and Future Directions," Expert Reviews Ophthalmology, 5(5):627-636.
Chua, et al. (2006) "Necrostatin-1 is a Novel Protector of Myocardial Infarction," 79th Annual Scientific Session of the American Heart Association, Chicago, IL, 114(18):212. (Abstract).
Cook, et al. (1995) "Apoptotic Photoreceptor Degeneration in Experimental Retinal Detachment," Investigative Ophthalmology & Visual Science, 36: 990-996.
Cuervo, et al. (1996) "A Receptor for the Selective Uptake and Degradation of Proteins by Lysosomes," Science, 273:501-503.
Cuny, et al. (2008) "Necroptosis-A Novel Cell Death Mechanism," Drugs of the Future, 33(3):225-233.
D'Onofrio, et al. (2011) "Involvement of Caspase-6 and Caspase-8 in Neuronal Apoptosis and the Regenerative Failure of Injured Retinal Ganglion Cells," Investigative Ophthalmology & Visual Science, p. 5448. (Abstract).
Degterev, et al. (2005) "Chemical Inhibitor of Nonapoptotic Cell Death with Therapeutic Potential for Ischemic Brain Injury," Nature Chemical Biology, 1:112-119.
Degterev, et al. (2008) "Identification of RIP1 Kinase as a Specific Cellular Target of Necrostatins," Nature Chemical Biology, 4:313-321.
Deveraux, et al. (1998) "IAPs Block Apoptotic Events Induced by Caspase-8 and Cytochrome c by Direct Inhibition of Distinct Caspases," The EMBO Journal, 17:2215-2223.
Dice (2007) "Chaperone-Mediated Autophagy," Autophagy, 3:295-299.
Donovan, et al. (2009) " Caspase-Independent Photoreceptor Apoptosis in vivo and Differential Expression of Apoptotic Protease Activating Factor-1 and Caspase-3 During Retinal Development," Cell Death and Differentiation, 9:1220-1231.
Dreyer, et al. (1996) "Elevated Glutamate Levels in the Vitreous Body of Humans and Monkeys with Glaucoma," Arch Ophthalmology, 114(3):299-305.
Dunaief, et al. (2002) "The Role of Apoptosis in Age-Related Macular Degeneration," Arch Ophthalmology, 120:1435-1442.
Ekert, et al. (1999) "Caspase Inhibitors," Cell Death and Differentiation, 6:1081-1086.

Erickson, et al. (1983) "Retinal Detachment in the Cat: The Outer Nuclear and Outer Plexiform Layers," Investigative Ophthalmology & Visual Science, 24: 927-942.
Festjens, et al. (2006) "Necrosis, a Well-Orchestrated Form of Cell Demise: Signaling Cascades, Important Mediators and Concomitant Immune Response," Biochim Biophys Acta, 1757:1371-1387.
Festjens, et al. (2007) "RIP1, A Kinase on the Crossroads of a Cell's Decision to Live or Die," Cell Death and Differentiation 14:400-410.
Fulton, et al. (2001) "The Rod Photoreceptors in Retinopathy of Prematurity, An Electroretinographic Study," Arch Ophthalmology, 119:499-505.
Galluzzi, et al. (2008) "Necroptosis: A Specialized Pathway of Programmed Necrosis," Cell, 135:1161-1163.
Galluzzi, et al. (2009) "RIP Kinases Initiate Programmed Necrosis," Journal of Molecular Cell Biology, 1:8-10.
Golstein, et al. (2007) "Cell Death by Necrosis: Towards a Molecular Definition," Trends in Biochemical Sciences, 32:37-43.
Grasl-Kraupp, et al. (1995) "In Situ Detection of Fragmented DNA (TUNEL Assay) Fails to Discriminate Among Apoptosis, Necrosis, and Autolytic Cell Death: A Cautionary Note," Hepatology, 21:1465-1468.
Hagimura, et al. (2002) "Persistent Foveal Retinal Detachment After Successful Rhegmatogenous Retinal Detachment Surgery," American Journal of Ophthalmology, 133:516-520.
He, et al. (2009) "Receptor Interacting Protein Kinase-3 Determines Cellular Necrotic Response to TNF-α," Cell, 137:1100-1111.
Hisatomi, et al. (2001) "Relocalization of Apoptosis-Inducing Factor in Photoreceptor Apoptosis Induced by Retinal Detachment In Vivo," American Journal of Pathology, 158:1271-1278.
Hisatomi, et al. (2003) "Elimination of Apoptotic Debris into the Subretinal Space and Macrophage-Mediated Phagocytosis via Phosphatidylserine Receptor and Integrin αvβ3," American Journal of Pathoogy, 162:1869-1879.
Histatomi, et al. (2008) "HIV Protease Inhibitors Provide Neuroprotection Through Inhibition of Mitochondrial Apoptosis in Mice," Journal of Clinical Investigation, 118:2025-2038.
Hoglen, et al. (2004) "Characterization of IDN-6556 (3-{2-(2-tert-Butyl-Phenylaminooxalyl)-Amino]-Propionylamino}-4-oxo-5-(2,3,5,6-Tetrafluoro-Phenoxy-Pentanoic Acid): A Liver-Targeted Caspase Inhibitor," Journal of Pharmacology and Experimental Therapeutics, 309:634-640.
Holler, et al. (2000) "Fas Triggers an Alternative, Caspase-8-Independent Cell Death Pathway Using the Kinase RIP as Effector Molecule," Journal of Nature Immunology, 1:489-495.
Ichimura, et al. (2000) "A Ubiquitin-Like System Mediates Protein Lipidation," Nature, 408:488-492.
International Search Report and Written Opinion for PCT/US2011/057327, mailed May 21, 2013, (15 pages).
International Search Report and Written Opinion for PCT/US2012/061324, mailed May 16, 2013, (17 pages).
International Search Report and Written Opinion for PCT/US2011/033704, mailed Jun. 22, 2012, (14 pages.).
Jones (2005) "Neurodegenerative Disorders: Blocking a Path to Cell Death," [online] [retrieved on Mar. 12, 2015] Retrieved from 22.signaling-gateway.org/Update/Updates/200508/nrn1732.html. (2 pages).
Kabeya, et al. (2000) "LC3, a Mammalian Homologue of Yeast Apg8p, is Localized in Autophagosome Membranes After Processing," EMBO Journal, 19(21):5720-5728.
Kaiser, et al. (2008) "Receptor-Interacting Protein Homotypic Interaction Motif-Dependent Control of NF-β Activation via the DNA-Dependent Activator of IFN Regulatory Factors," Journal of Immunology, 181:6427-6434.
Karl, et al. (2008) "Stimulation of Neural Regeneration in the Mouse Retina," Proceedings of the National Academy of Science U.S.A. 105(49):19508-19513.
Kayama, et al. (2010) "Transfection with pax6 Gene of Mouse Embryonic Stem Cells and Subsequent Cell Cloning Induced Retinal Neuron Progenitors, including Retinal Ganglion Cell-Like Cells, In Vitro," Ophthalmic Research, 43(2):79-91.
Kelliher, et al. (1998) "The Death Domain Kinase RIP Mediates the TNF-Induced NF-κβ Signal," Immunity, 8:297-303.

(56) References Cited

OTHER PUBLICATIONS

Kermer, et al., (1998) "Inhibition of CPP32-Like Proteases Rescues Axotomized Retinal Ganglion Cells from Secondary Cell Death in vivo," Journal of Neuroscience, 18:4656-4662.

Kermer, et al. (2000) "Caspase-9: Involvement in Secondary Death of Axotomized Rat Retinal Ganglion Cells In Vivo," Molecular Brain Research, 85:144-150.

Kerrigan, et al. (1997) "TUNEL-Positive Ganglion Cells in Human Primary Open-Angle Glaucoma," Arch Ophthalmology, 115:1031-1035.

Kim, et al. (2007) "TNF-Induced Activation of the Nox1 NADPH Oxidase and Its Role in the Induction of Necrotic Cell Death," Molecular Cell, 26:675-687.

Knöferle, et al. (2010) "Mechanisms of Acute Axonal Degeneration in the Optic Nerve In Vivo," Proceedings of the National Academy of Science U.S.A., 107(13):6064-6069.

Kourtis, et al. (2009) "Autophagy and Cell Death in Model Organisms," Cell Death and Differentiation, 16:21-30.

Krantic, et al. (2007) "Apoptosis-Inducing Factor: A Matter of Neuron Life and Death," Progress in Neurobiology, 81:179-196.

Kroemer, et al. (2009) "Classification of Cell Death: Recommendations of the Nomenclature Committee on Cell Death 2009," Cell Death and Differentiation, 16:3-11.

Kubay, et al. (2005) "Retinal Detachment Neuropathology and Potential Strategies for Neuroprotection," Survey of Ophthalmology, 50:463-475.

Lee, et al. (2004) "The Kinase Activity of Rip1 is Not Required for Tumor Necrosis Factor-α-Induced IκB Kinase or p38 MAP Kinase Activation or for the Ubiquitination of Rip1 by Traf2," The Journal of Biological Chemistry, 279(32):33185-33191.

Leon, et al. (2000) "Lens Injury Stimulates Axon Regeneration in the Mature Rat Optic Nerve," The Journal of Neuroscience, 20(12):4615-4626.

Levine, et al. (2004) "Development by Self-Digestion: Molecular Mechanisms and Biological Functions of Autophagy," Developmental Cell, 6(4):463-477.

Levine, et al. (2005) "Autophagy in Cell Death: An Innocent Convict?," The Journal of Clinical Investigation, 115(10):2679-2688.

Levkovitch-Verbin (2004) "Animal Models of Optic Nerve Diseases," Eye, 18(11):1066-1074.

Li, et al. (2006) "Ubiquitination of RIP is Required for Tumor Necrosis Factor α-induced NF-κB Activation," The Journal of Biological Chemistry, 281(19):13636-13643.

Libby, et al. (2005) "Susceptibility to Neurodegeneration in a Glaucoma is Modified by Bax Gene Dosage," PLoS Genetics, 1(1):0017-0026.

Lin, et al. (1999) "Cleavage of the Death Domain Kinase RIP by Caspase-8 Prompts TNF-induced Apoptosis," Genes & Development, 13:2514-2526.

Lin, et al. (2004) "Tumor Necrosis Factor-Induced Nonapoptotic Cell Death Requires Receptor-Interacting Protein-Mediated Cellular Reactive Oxygen Species Accumulation," The Journal of Biological Chemistry, 279(11):10822-10828.

Linton (2005) "Caspase Inhibitors: A Pharmaceutical Industry Perspective," Current Topics in Medicinal Chemistry, 5:1697-1717.

Mahoney, et al. (2008) "Both cIAP1 and cIAP2 Regulate TNFα-Mediated NF-κB Activation," Proceedings of the National Academy of Science U.S.A., 105:11778-11783.

Mann, et al. (1948) "The Perception of the Vertical: I. Visual and Non-Labyrinthine Cues," Investigation conducted jointly with the School of Aviation Medicine and Research with the Office of Naval Research, Journal of Experimental Psychology, 39(4):538-547.

Merfeld (2011) "Signal Detection Theory and Vestibular Thresholds: I. Basic Theory and Practical Considerations," Experimental Brain Research, 210:389-405.

Moubarak, et al. (2007) "Sequential Activation of Poly(ADP-Ribose) Polymerase 1, Calpains, and Bax is Essential in Apoptosis-Inducing Factor-Mediated Programmed Necrosis," Molecular Cell Biology, 27(13):4844-4862.

Murakami, et al. (2008) "Cell Injury, Repair, Aging and Apoptosis, Inhibition of Nuclear Translocation of Apoptosis-Inducing Factor is an Essential Mechanism of the Neuroprotective Activity of Pigment Epithelium-Derived Factor in a Rat Model of Retinal Degeneration," American Journal of Pathology, 173(5):1326-1338.

Murakami, et al. (2010) "Receptor Interacting Protein 1 Kinase is an Essential Mediator of Programmed Photoreceptor Necrosis After Retinal Detachment," Association for Research in Vision and Ophthalmology (ARVO) 2010 Annual Meeting, Ft. Lauderdale, FL May 2-6, 2010, Program #/Poster #:4034/A427, (2 pages (Abstract available online Apr. 23, 2010).

Nakazawa, et al. (2006) "Characterization of Cytokine Responses to Retinal Detachment in Rats," Molecular Vision, 12:867-878.

Nakazawa, et al. (2006) "Tumor Necrosis Factor-α Mediates Oligodendrocyte Death and Delayed Retinal Ganglion Cell Loss in a Mouse Model of Glaucoma," Journal of Neuroscience, 26(49):12633-12641.

Nakazawa, et al. (2007) "Monocyte Chemoattractant Protein 1 Mediates Retinal Detachment-Induced Photoreceptor Apoptosis," Proceedings of National Academy of Science, U.S.A., 104:2425-2430.

Newton, et al. (2004) "Kinase RIP3 Is Dispensable for Normal NF-1Bs, Signaling by the β-Cell and T-Cell Receptors, Tumor Necrosis Factor Receptor 1, and Toll-Like Receptors 2 and 4," Molecular Cellular Biology, 24:1464-1469.

Papapetropoulos, et al. (2000) "Angiopoietin-1 Inhibits Endothelial Cell Apoptosis via the Akt/Survivin Pathway," Journal of Biological Chemistry, 275:9102-9105.

Rosenbaum, et al. (2009) "Necroptosis, a Novel Form of Caspase-Independent Cell Death, Contributes to Neuronal Damage in a Retinal Ischemia-Reperfusion Injury Model," Journal of Neuroscience Research, 88:1569-1576.

Saggu, et al. (2010) "Wallerian-like Axonal Degeneration in the Optic Nerve After Excitotoxic Retinal Insult: An Ultrastructural Study," BMC Neuroscience, 11:97-113.

Sanges, et al. (2006) "Apoptosis in Retinal Degeneration Involves Cross-Talk Between Apoptosis-Inducing Factor (AIF) and Caspase-12 and is Blocked by Calpain Inhibitors," Proceedings of National Academy of Science, U.S.A., 103:17366-17371.

Scaffidi, et al. (2002) "Release of Chromatin Protein HMGB1 by Necrotic Cells Triggers Inflammation," Nature, 418:191-195.

Seglen, et al. (1982) "3-Methyladenine: Specific Inhibitor of Autophagic/Lysosomal Protein Degradation in Isolated Rat Hepatocytes," Proceedings of National Academy of Science, U.S. A., Cell Biology, 79:1889-1892.

Sintzel, et al. (1996) "Biomaterials in Ophthalmic Drug Delivery," European Journal of Pharmaceutics and Biopharmaceutics, 42:358-374.

Susin (2000) "Two Distinct Pathways Leading to Nuclear Apoptosis," Journal of Experimental Medicine, 192(4): 571-580.

Susin, et al. (1999) "Molecular Characterization of Mitochondrial Apoptosis-Inducing Factor," Nature, 397:441-446.

Tatton, et al. (2001) "Maintaining Mitochondrial Membrane Impermeability: An Opportunity for New Therapy in Glaucoma?," Survey of Ophthalmology, 45(3):S277-S283.

Teng, et al. (2007) "Structure-Activity Relationship Study of [1,2,3] Thiadiazole Necroptosis Inhibitors," Bioorganic & Medicinal Chemistry Letters, 17:6836-6840.

Teng, et al. (2008) "Structure-Activity Relationship and Liver Microsome Stability Studies of Pyrrole Necroptosis Inhibitors," Bioorganic & Medicinal Chemistry Letters, 18:3219-3223.

Tezel, et al. (2001) "TNF-α and TNF-α Receptor-1 in the Retina of Normal and Glaucomatous Eyes," Investigative Ophthalmology & Visual Science, 42(8):1787-1794.

Trichonas, et al. (2009) "Identification of Necroptosis as a Mechanism of Photoreceptor Damage After Retinal Detachment and Nec-1 as a Potential Treatment," Investigative Ophthalmology & Visual Science, 50:5187 (2 pages) (e-Abstract).

Trichonas, et al. (2010) "Receptor Interacting Protein Kinases Mediate Retinal Detachment-Induced Photoreceptor Necrosis and Compensate for Inhibition of Apoptosis," Proceedings of National Academy of Science, U.S.A., 107:21695-21700.

(56) References Cited

OTHER PUBLICATIONS

Tuo, et al. (2007) "Murine Ccl2/Cx3cr1 Deficiency Results in Retinal Lesions Mimicking Human Age-Related Macular Degeneration," Investigative Ophthalmology & Visual Science, 48(8):3827-3836.

Vandenabeele, et al. (2010) "The Role of the Kinases RIP1 and RIP3 in TNF-Induced Necrosis," Scientific Signaling, 3:re4.

Vanlangenakker, et al. (2011) "cIAP1 and TAK1 protect cells from TNF-induced necrosis by preventing RIP1/RIP3-dependent reactive oxygen species production," Cell Death and Differentiation, 18:656-665.

Vavvas, et al., (2008) "Identification of Necroptosis as a Mechanism of Photoreceptor Damage after Retinal Detachment and Nec-1 as a Potential Treatment," 41st Annual Meeting of the Retina Society, Sep. 25-28, 2008, Scottsdale, AZ (1 page). (Abstract first available online Jun. 1, 2008).

Vercammen, et al. (1998) "Dual Signaling of the Fas Receptor: Initiation of Both Apoptotic and Necrotic Cell Death Pathways," Journal of Experimental Medicine, 188:919-930.

Wang, et al. (2008) "TNF-α Induces Two Distinct Caspase-8 Activation Pathways," Cell, 133:693-703.

Xu, et al. (2010) "Synergistic Protective Effects of Humanin and Necrostatin-1 on Hypoxia and Ischemia/Reperfusion Injury," Brain Research, 1355:189-194, (NIH Public Access author manuscript) (10 pages).

Yan, et al. (2000) "Matrix Metalloproteinases and Tumor Necrosis Factor-α in Glaucomatous Optic Nerve Head," Arch Ophthalmology, 118:666-673.

Yang, et al. (2008) "Toll-Like Receptor 3 and Geographic Atrophy in Age-Related Macular Degeneration," New England Journal of Medicine, 359:1456-1463.

Yu, L. et al. (2004) "Regulation of an ATG7-Beclin 1 Program of Autophagic Cell Death by Caspase-8," Science, 304(5676):1500-1502.

Yuan, et al. (2000) "Tumor Necrosis Factor-α: A Potentially Neurodestructive Cytokine Produced by Glia in the Human Glaucomatous Optic Nerve Head,", Glia, 32:42-50.

Zacks, et al. (2003) "Caspase Activation in an Experimental Model of Retinal Detachment," Investigative Ophthalmology & Visual Science, 44:1262-1267.

Zacks, et al. (2004) "FAS-Mediated Apoptosis and Its Relation to Intrinsic Pathway Activation in an Experimental Model of Retinal Detachment," Investigative Ophthalmology & Visual Science, 45:4563-4569.

Zacks, et al. (2007) "Role of the Fas-Signaling Pathway in Photoreceptor Neuroprotection," Arch Ophthalmology, 125:1389-1395.

Zhang, et al. (2009) "RIP3, an Energy Metabolism Regulator that Switches TNF-Induced Cell Death from Apoptosis to Necrosis," Science, 325:332-336.

Zheng, et al. (2008) "Structure-Activity Relationship Study of a Novel Necroptosis Inhibitor, Necrostatin-7," Bioorganic & Medicinal Chemistry Letters, 18:4932-4935.

Zhu, et al. (2000) "Stabilization of Proteins Encapsulated in Injectable Poly (Lactide-co-glycolide)," Nature Biotechnology, 18:52-57.

Zhu, et al. (2011) "Necrostatin-1 Ameliorates Symptoms in R6/2 Transgenic Mouse Model of Disease," Cell Death and Disease, 2:e115:1-114.

Zitvogel, et al. (2010) "Decoding Cell Death Signals in Inflammation and Immunity," Cell, 140:798-804.

Kong et al., (2009) "P25 Rescue of Motor Neurons in ALS by Targeting the BNIP3 Cell Death Pathway" Abstracts of the 20th International Symposium on Amyotrophic Lateral Sclerosis/Motor Neuron Diseases (ALS/MND). Dec. 8-10, 2009. Berlin, Germany. Amyotrophic Lateral Sclerosis, 10(Suppl 1):78-79.

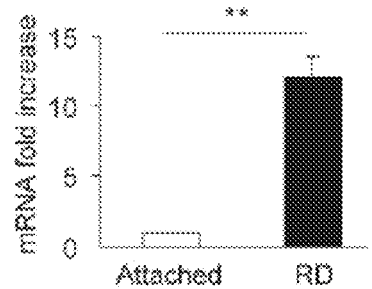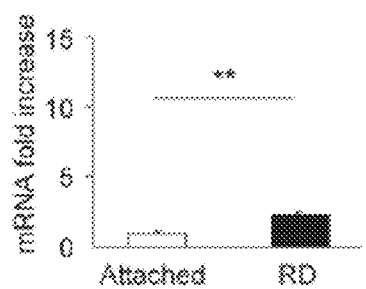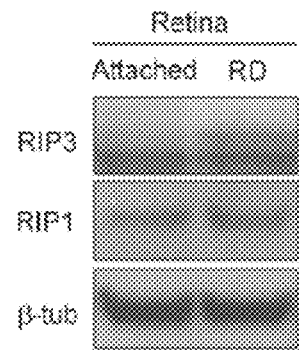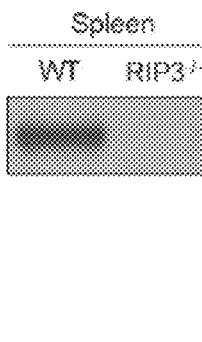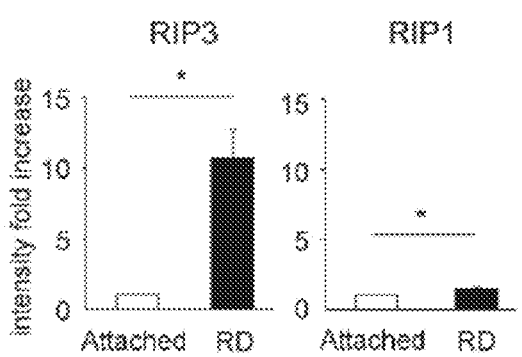
FIG. 1B FIG. 1C
FIG. 1D

FIG. 4A
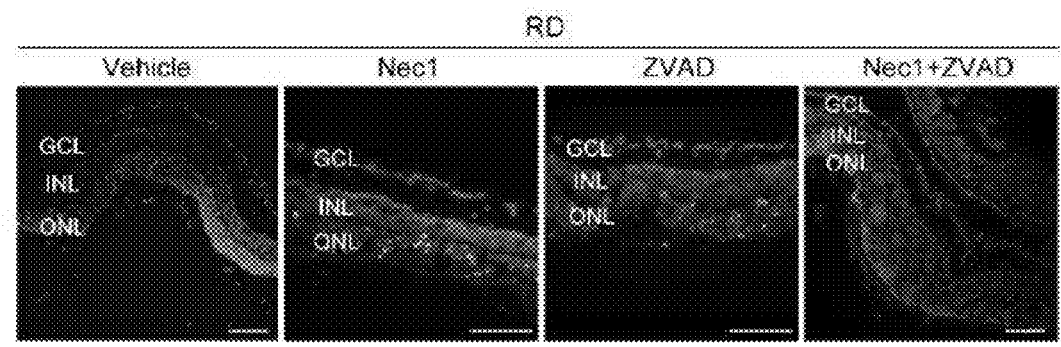
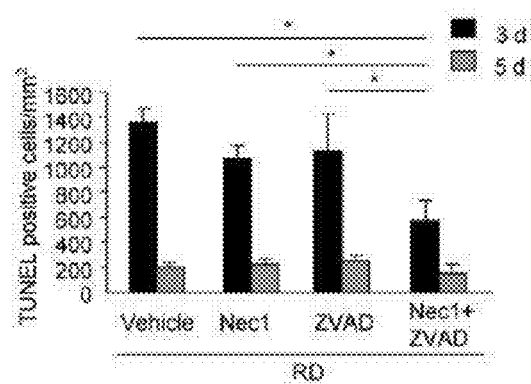
FIG. 4B
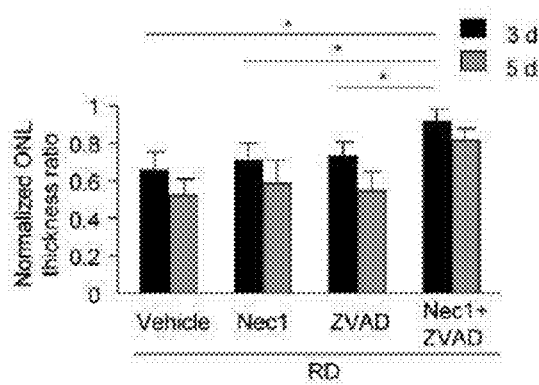
FIG. 4C

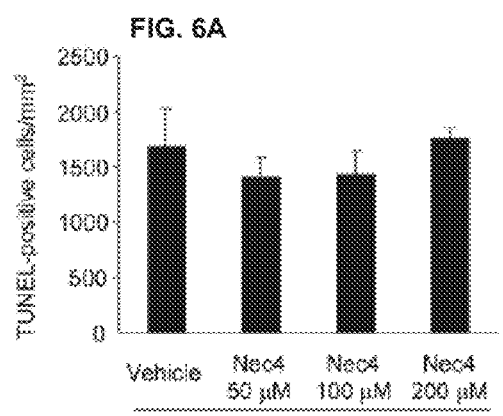
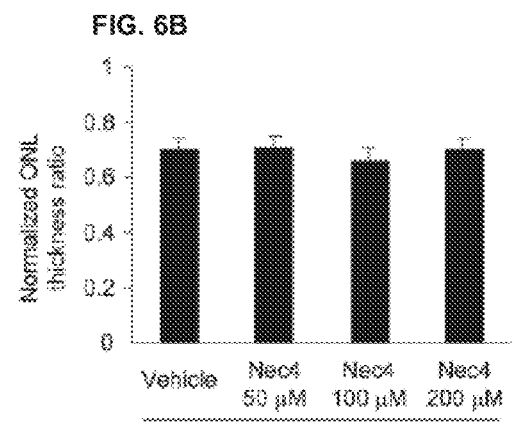
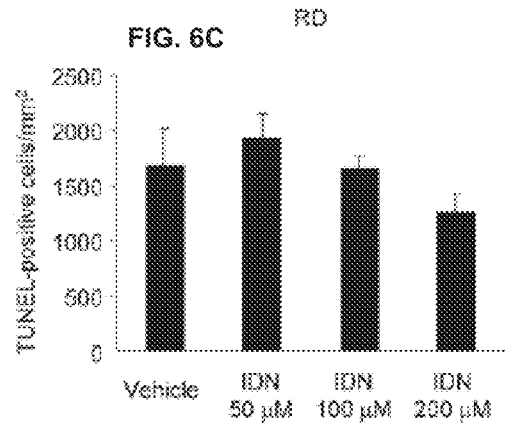
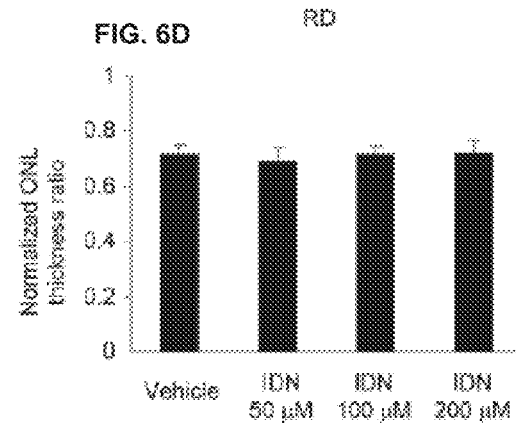
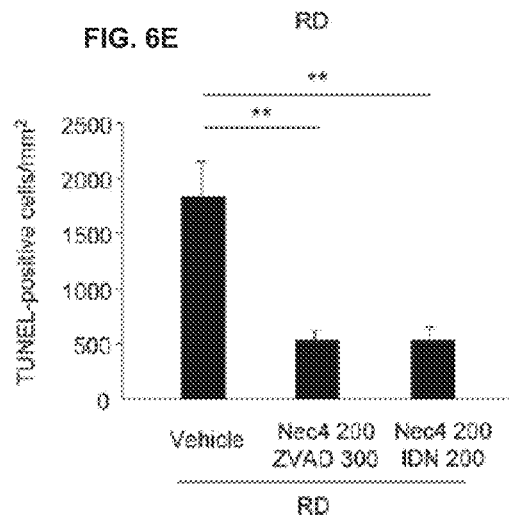
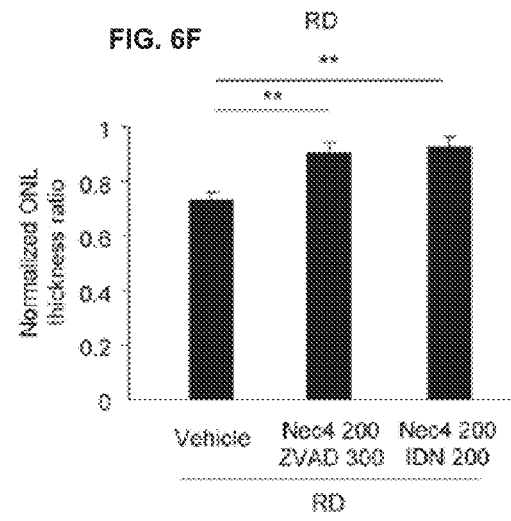

FIG. 7A 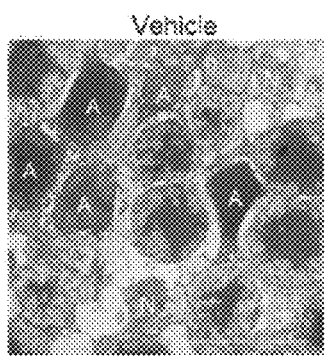 FIG. 7B 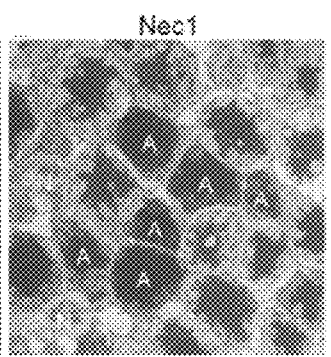 FIG. 7E 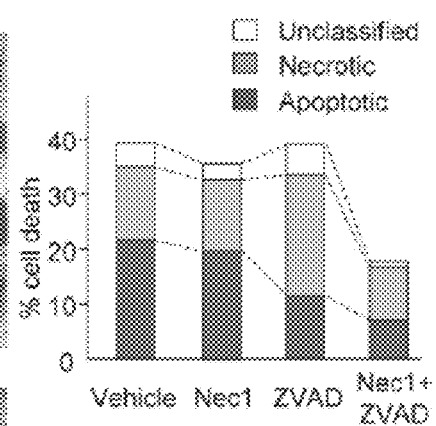
FIG. 7C 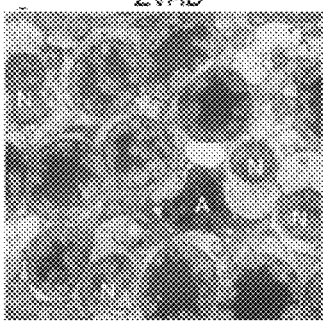 FIG. 7D FIG. 8A
FIG. 8B
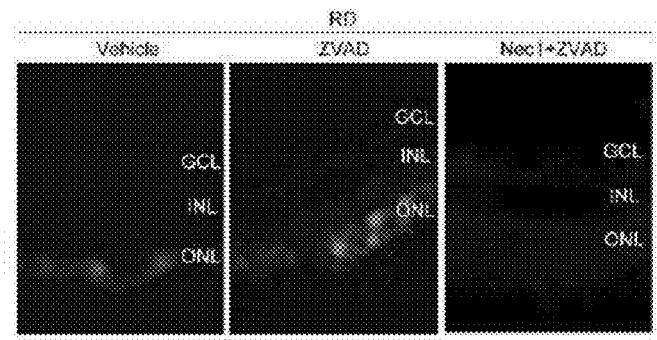
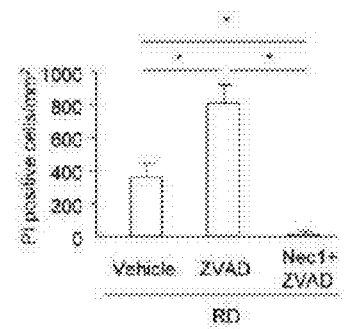
FIG. 8C
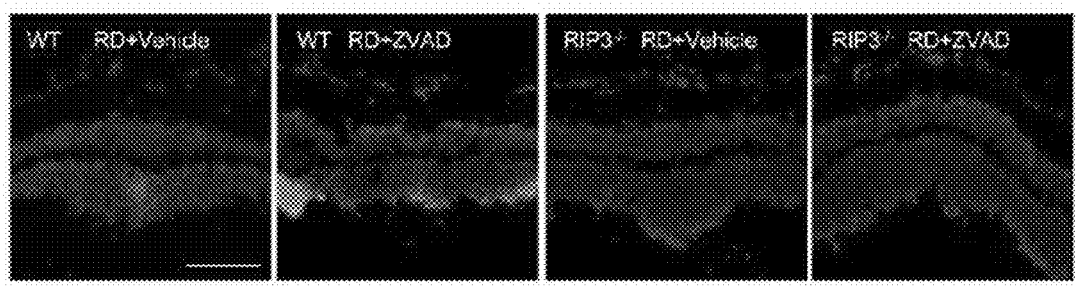
FIG. 8D
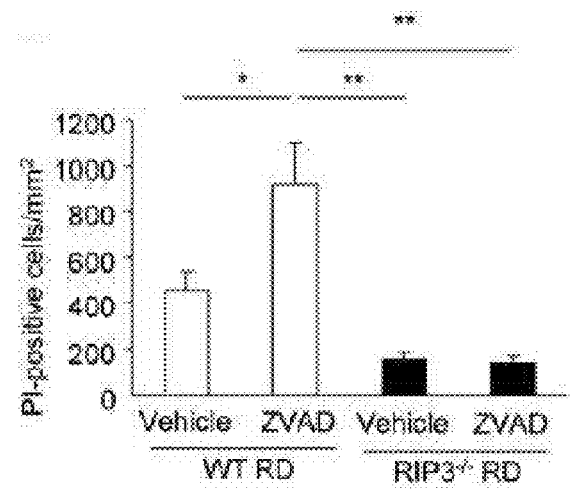

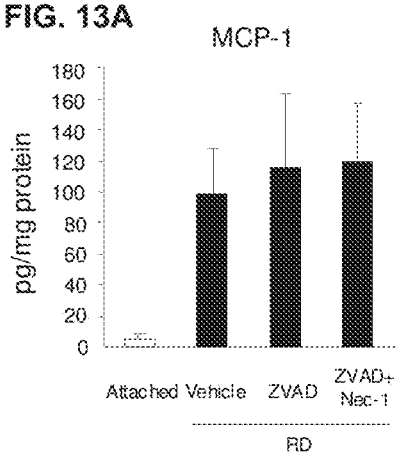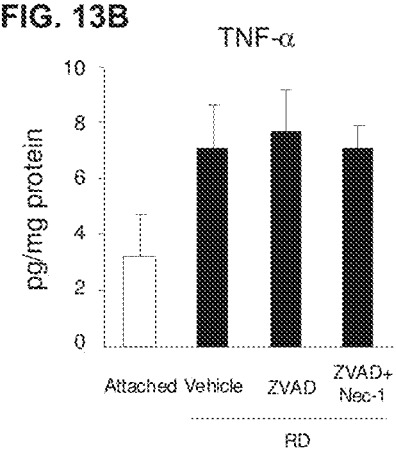

FIG. 18A
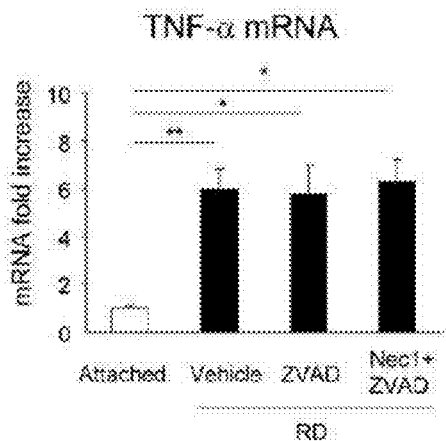
FIG. 18B
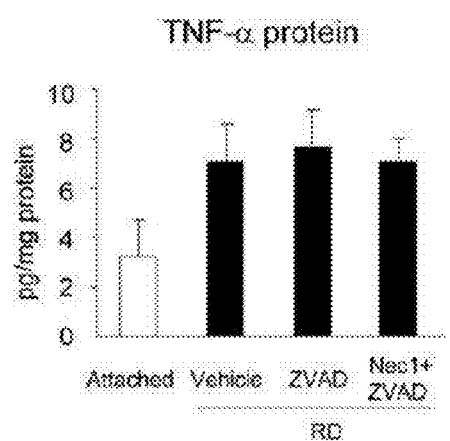
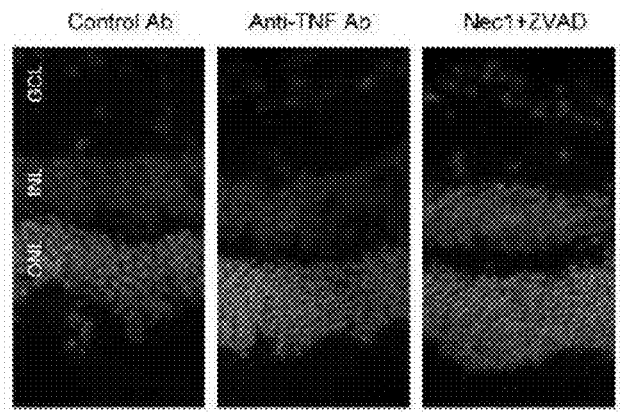
FIG. 18C
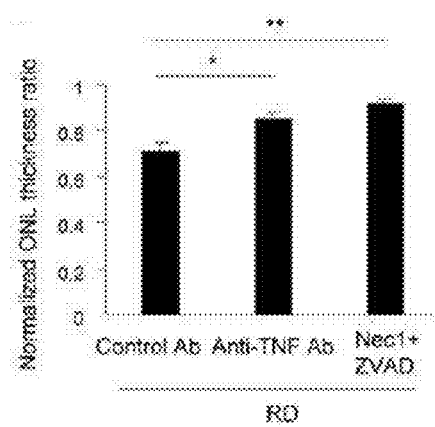
FIG. 18D

Primary RPE (WT)

Primary RPE (WT vs. RIP3KO)

SEQUENCE LISTING

```
<160> NUMBER OF SEQ ID NOS: 57

<210> SEQ ID NO 1
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Ala
<220> FEATURE:
<221> NAME/KEY: MOD_RES
<222> LOCATION: (19)..(19)
<223> OTHER INFORMATION: Asp-aldehyde

<400> SEQUENCE: 1

Ala Ala Val Ala Leu Leu Pro Ala Val Leu Leu Ala Leu Leu Pro Tyr
1               5                   10                  15

Val Ala Asp

<210> SEQ ID NO 2
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Ala
<220> FEATURE:
<221> NAME/KEY: MOD_RES
<222> LOCATION: (20)..(20)
<223> OTHER INFORMATION: Asp-aldehyde

<400> SEQUENCE: 2

Ala Ala Val Ala Leu Leu Pro Ala Val Leu Leu Ala Leu Leu Ala Pro
1               5                   10                  15

Asp Glu Val Asp
            20

<210> SEQ ID NO 3
<211> LENGTH: 20
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Ala
<220> FEATURE:
<221> NAME/KEY: MOD_RES
<222> LOCATION: (20)..(20)
<223> OTHER INFORMATION: Pro-aldehyde

<400> SEQUENCE: 3

Ala Ala Val Ala Leu Leu Pro Ala Val Leu Leu Ala Leu Leu Ala Pro
1               5                   10                  15

Leu Glu Val Pro
            20

<210> SEQ ID NO 4
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Ala
<220> FEATURE:
<221> NAME/KEY: MOD_RES
<222> LOCATION: (20)..(20)
<223> OTHER INFORMATION: Asp-aldehyde

<400> SEQUENCE: 4

Ala Ala Val Ala Leu Leu Pro Ala Val Leu Leu Ala Leu Leu Ala Pro
1               5                   10                  15

Val Glu Ile Asp
            20

<210> SEQ ID NO 5
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Ala
<220> FEATURE:
<221> NAME/KEY: MOD_RES
<222> LOCATION: (20)..(20)
<223> OTHER INFORMATION: Asp-aldehyde

<400> SEQUENCE: 5

Ala Ala Val Ala Leu Leu Pro Ala Val Leu Leu Ala Leu Leu Ala Pro
1               5                   10                  15

Ile Glu Thr Asp
            20

<210> SEQ ID NO 6
<211> LENGTH: 20
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Ala
<220> FEATURE:
<221> NAME/KEY: MOD_RES
<222> LOCATION: (20)..(20)
<223> OTHER INFORMATION: Asp-aldehyde

<400> SEQUENCE: 6

Ala Ala Val Ala Leu Leu Pro Ala Val Leu Leu Ala Leu Leu Ala Pro
1               5                   10                  15

Leu Glu His Asp
            20

<210> SEQ ID NO 7
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-N-Me-Tyr
<220> FEATURE:
<221> NAME/KEY: MOD_RES
<222> LOCATION: (4)..(4)
<223> OTHER INFORMATION: Asp-aldehyde

<400> SEQUENCE: 7

Tyr Val Ala Asp
1

<210> SEQ ID NO 8
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Trp
<220> FEATURE:
<221> NAME/KEY: MOD_RES
<222> LOCATION: (4)..(4)
<223> OTHER INFORMATION: Asp-aldehyde

<400> SEQUENCE: 8

Trp Glu His Asp
1

<210> SEQ ID NO 9
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
```

```
<223> OTHER INFORMATION: Ac-Tyr
<220> FEATURE:
<221> NAME/KEY: MOD_RES
<222> LOCATION: (2)..(2)
<223> OTHER INFORMATION: N-Me-Val
<220> FEATURE:
<221> NAME/KEY: MOD_RES
<222> LOCATION: (4)..(4)
<223> OTHER INFORMATION: N-Me-Asp-aldehyde

<400> SEQUENCE: 9

Tyr Val Ala Asp
1

<210> SEQ ID NO 10
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (4)..(4)
<223> OTHER INFORMATION: Asp-aldehyde

<400> SEQUENCE: 10

Tyr Val Ala Asp
1

<210> SEQ ID NO 11
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (4)..(4)
<223> OTHER INFORMATION: Asp-chloromethylketone

<400> SEQUENCE: 11

Tyr Val Ala Asp
1

<210> SEQ ID NO 12
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (4)..(4)
<223> OTHER INFORMATION: Asp-2,6-dimethylbenzoyloxymethylketone
```

```
<400> SEQUENCE: 12

Tyr Val Ala Asp
1

<210> SEQ ID NO 13
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (4)..(4)
<223> OTHER INFORMATION: Asp(OtBu)-aldehyde-dimethyl acetol

<400> SEQUENCE: 13

Tyr Val Ala Asp
1

<210> SEQ ID NO 14
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (4)..(4)
<223> OTHER INFORMATION: Asp-aldehyde

<400> SEQUENCE: 14

Tyr Val Lys Asp
1

<210> SEQ ID NO 15
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (3)..(3)
<223> OTHER INFORMATION: Lys(biotinyl)
<220> FEATURE:
<221> NAME/KEY: MOD_RES
<222> LOCATION: (4)..(4)
<223> OTHER INFORMATION: Asp-2,6-dimethylbenzoyloxymethylketone

<400> SEQUENCE: 15

Tyr Val Lys Asp
1
```

```
<210> SEQ ID NO 16
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Biotinyl-Tyr
<220> FEATURE:
<221> NAME/KEY: MOD_RES
<222> LOCATION: (4)..(4)
<223> OTHER INFORMATION: Asp-chloromethylketone

<400> SEQUENCE: 16

Tyr Val Ala Asp
1

<210> SEQ ID NO 17
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ethoxycarbonyl-Ala
<220> FEATURE:
<221> NAME/KEY: MOD_RES
<222> LOCATION: (5)..(5)
<223> OTHER INFORMATION: Asp-aldehyde

<400> SEQUENCE: 17

Ala Tyr Val Ala Asp
1               5

<210> SEQ ID NO 18
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Tyr
<220> FEATURE:
<221> NAME/KEY: MOD_RES
<222> LOCATION: (4)..(4)
<223> OTHER INFORMATION: Asp-chloromethylketone

<400> SEQUENCE: 18

Tyr Val Ala Asp
1

<210> SEQ ID NO 19
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (1)..(1)
<223> OTHER INFORMATION: Carbobenzoxy-Tyr
<220> FEATURE:
<221> NAME/KEY: MOD_RES
<222> LOCATION: (4)..(4)
<223> OTHER INFORMATION: DL-Asp-fluoromethylketone

<400> SEQUENCE: 19

Tyr Val Ala Asp
1

<210> SEQ ID NO 20
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Biotin-Tyr
<220> FEATURE:
<221> NAME/KEY: MOD_RES
<222> LOCATION: (4)..(4)
<223> OTHER INFORMATION: Asp-fluoroacyloxymethylketone

<400> SEQUENCE: 20

Tyr Val Ala Asp
1

<210> SEQ ID NO 21
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (4)..(4)
<223> OTHER INFORMATION: Asp-acyloxymethylketone

<400> SEQUENCE: 21

Tyr Val Ala Asp
1

<210> SEQ ID NO 22
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Tyr
<220> FEATURE:
<221> NAME/KEY: MOD_RES
<222> LOCATION: (4)..(4)
<223> OTHER INFORMATION: Asp-fluoromethylketone

<400> SEQUENCE: 22

Tyr Val Ala Asp
```

```
<210> SEQ ID NO 23
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Val
<220> FEATURE:
<221> NAME/KEY: MOD_RES
<222> LOCATION: (5)..(5)
<223> OTHER INFORMATION: Asp-aldehyde

<400> SEQUENCE: 23

Val Asp Val Ala Asp
1               5

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Val
<220> FEATURE:
<221> NAME/KEY: MOD_RES
<222> LOCATION: (5)..(5)
<223> OTHER INFORMATION: Asp-fluoromethylketone

<400> SEQUENCE: 24

Val Asp Val Ala Asp
1               5

<210> SEQ ID NO 25
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Glu
<220> FEATURE:
<221> NAME/KEY: MOD_RES
<222> LOCATION: (4)..(4)
<223> OTHER INFORMATION: Asp-aldehyde

<400> SEQUENCE: 25

Glu Ser Met Asp
1

<210> SEQ ID NO 26
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
```

```
      Synthetic peptide"
<220> FEATURE:
<221> NAME/KEY: MOD_RES
<222> LOCATION: (1)..(1)
<223> OTHER INFORMATION: Ac-Ile
<220> FEATURE:
<221> NAME/KEY: MOD_RES
<222> LOCATION: (4)..(4)
<223> OTHER INFORMATION: Asp-aldehyde

<400> SEQUENCE: 26

Ile Glu Thr Asp
1

<210> SEQ ID NO 27
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Asp
<220> FEATURE:
<221> NAME/KEY: MOD_RES
<222> LOCATION: (4)..(4)
<223> OTHER INFORMATION: Asp-aldehyde

<400> SEQUENCE: 27

Asp Glu Val Asp
1

<210> SEQ ID NO 28
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Asp
<220> FEATURE:
<221> NAME/KEY: MOD_RES
<222> LOCATION: (4)..(4)
<223> OTHER INFORMATION: Asp-aldehyde

<400> SEQUENCE: 28

Asp Met Gln Asp
1

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Biotinyl-Asp
<220> FEATURE:
<221> NAME/KEY: MOD_RES
<222> LOCATION: (4)..(4)
<223> OTHER INFORMATION: Asp-aldehyde
```

```
<400> SEQUENCE: 29

Asp Glu Val Asp
1

<210> SEQ ID NO 30
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Asp
<220> FEATURE:
<221> NAME/KEY: MOD_RES
<222> LOCATION: (4)..(4)
<223> OTHER INFORMATION: Asp-chloromethylketone

<400> SEQUENCE: 30

Asp Glu Val Asp
1

<210> SEQ ID NO 31
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Asp(OMe)
<220> FEATURE:
<221> NAME/KEY: MOD_RES
<222> LOCATION: (2)..(2)
<223> OTHER INFORMATION: Glu(OMe)
<220> FEATURE:
<221> NAME/KEY: MOD_RES
<222> LOCATION: (4)..(4)
<223> OTHER INFORMATION: DL-Asp(OMe)-fluoromethylketone

<400> SEQUENCE: 31

Asp Glu Val Asp
1

<210> SEQ ID NO 32
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="Biotinylated"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Asp-fluoromethylketone

<400> SEQUENCE: 32
```

```
Xaa Asp Glu Val Asp
1               5

<210> SEQ ID NO 33
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Asp
<220> FEATURE:
<221> NAME/KEY: MOD_RES
<222> LOCATION: (4)..(4)
<223> OTHER INFORMATION: Asp-chloromethylketone

<400> SEQUENCE: 33

Asp Glu Val Asp
1

<210> SEQ ID NO 34
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: N-benzyloxycarbonal-Asp(OMe)
<220> FEATURE:
<221> NAME/KEY: MOD_RES
<222> LOCATION: (2)..(2)
<223> OTHER INFORMATION: Glu(OMe)
<220> FEATURE:
<221> NAME/KEY: MOD_RES
<222> LOCATION: (4)..(4)
<223> OTHER INFORMATION: Asp(Ome)-fluoromethylketone

<400> SEQUENCE: 34

Asp Glu Val Asp
1

<210> SEQ ID NO 35
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Leu
<220> FEATURE:
<221> NAME/KEY: MOD_RES
<222> LOCATION: (4)..(4)
<223> OTHER INFORMATION: Asp-aldehyde

<400> SEQUENCE: 35

Leu Glu Val Asp
1

<210> SEQ ID NO 36
<211> LENGTH: 4
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Tyr
<220> FEATURE:
<221> NAME/KEY: MOD_RES
<222> LOCATION: (4)..(4)
<223> OTHER INFORMATION: DL-Asp-fluoromethylketone

<400> SEQUENCE: 36

Tyr Val Ala Asp
1

<210> SEQ ID NO 37
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Trp
<220> FEATURE:
<221> NAME/KEY: MOD_RES
<222> LOCATION: (4)..(4)
<223> OTHER INFORMATION: Asp-fluoromethylketone

<400> SEQUENCE: 37

Trp His Glu Asp
1

<210> SEQ ID NO 38
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Trp
<220> FEATURE:
<221> NAME/KEY: MOD_RES
<222> LOCATION: (4)..(4)
<223> OTHER INFORMATION: Asp-aldehyde

<400> SEQUENCE: 38

Trp Glu His Asp
1

<210> SEQ ID NO 39
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Trp
```

```
<220> FEATURE:
<221> NAME/KEY: MOD_RES
<222> LOCATION: (2)..(2)
<223> OTHER INFORMATION: Glu(O-Me)
<220> FEATURE:
<221> NAME/KEY: MOD_RES
<222> LOCATION: (4)..(4)
<223> OTHER INFORMATION: Asp(O-Me) fluoromethylketone

<400> SEQUENCE: 39

Trp Glu His Asp
1

<210> SEQ ID NO 40
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Val
<220> FEATURE:
<221> NAME/KEY: MOD_RES
<222> LOCATION: (4)..(4)
<223> OTHER INFORMATION: Asp-aldehyde

<400> SEQUENCE: 40

Val Glu Ile Asp
1

<210> SEQ ID NO 41
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Val
<220> FEATURE:
<221> NAME/KEY: MOD_RES
<222> LOCATION: (4)..(4)
<223> OTHER INFORMATION: Asp-fluoromethylketone

<400> SEQUENCE: 41

Val Glu Ile Asp
1

<210> SEQ ID NO 42
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Asp(OMe)
<220> FEATURE:
<221> NAME/KEY: MOD_RES
<222> LOCATION: (4)..(4)
<223> OTHER INFORMATION: Asp(OMe) fluoromethylketone

<400> SEQUENCE: 42
```

Asp Gln Met Asp
1

<210> SEQ ID NO 43
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Asp
<220> FEATURE:
<221> NAME/KEY: MOD_RES
<222> LOCATION: (4)..(4)
<223> OTHER INFORMATION: Asp-aldehyde

<400> SEQUENCE: 43

Asp Glu Val Asp
1

<210> SEQ ID NO 44
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Biotin-Asp
<220> FEATURE:
<221> NAME/KEY: MOD_RES
<222> LOCATION: (4)..(4)
<223> OTHER INFORMATION: Asp-fluoromethylketone

<400> SEQUENCE: 44

Asp Glu Val Asp
1

<210> SEQ ID NO 45
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Asp
<220> FEATURE:
<221> NAME/KEY: MOD_RES
<222> LOCATION: (4)..(4)
<223> OTHER INFORMATION: Asp-fluoromethylketone

<400> SEQUENCE: 45

Asp Glu Val Asp
1

<210> SEQ ID NO 46
<211> LENGTH: 4
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Asp
<220> FEATURE:
<221> NAME/KEY: MOD_RES
<222> LOCATION: (4)..(4)
<223> OTHER INFORMATION: Asp-aldehyde

<400> SEQUENCE: 46

Asp Glu Val Asp
1

<210> SEQ ID NO 47
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Ile
<220> FEATURE:
<221> NAME/KEY: MOD_RES
<222> LOCATION: (4)..(4)
<223> OTHER INFORMATION: Asp-aldehyde

<400> SEQUENCE: 47

Ile Glu Pro Asp
1

<210> SEQ ID NO 48
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Ile
<220> FEATURE:
<221> NAME/KEY: MOD_RES
<222> LOCATION: (4)..(4)
<223> OTHER INFORMATION: Asp-aldehyde

<400> SEQUENCE: 48

Ile Glu Thr Asp
1

<210> SEQ ID NO 49
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Trp
<220> FEATURE:
<221> NAME/KEY: MOD_RES
<222> LOCATION: (4)..(4)
```

<223> OTHER INFORMATION: Asp-aldehyde

<400> SEQUENCE: 49

Trp Glu His Asp
1

<210> SEQ ID NO 50
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Boc-Ala
<220> FEATURE:
<221> NAME/KEY: MOD_RES
<222> LOCATION: (4)..(4)
<223> OTHER INFORMATION: Asp-aldehyde

<400> SEQUENCE: 50

Ala Glu Val Asp
1

<210> SEQ ID NO 51
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Ile
<220> FEATURE:
<221> NAME/KEY: MOD_RES
<222> LOCATION: (4)..(4)
<223> OTHER INFORMATION: Asp-fluoromethylketone

<400> SEQUENCE: 51

Ile Glu Thr Asp
1

<210> SEQ ID NO 52
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Asp
<220> FEATURE:
<221> NAME/KEY: MOD_RES
<222> LOCATION: (4)..(4)
<223> OTHER INFORMATION: Asp-aldehyde

<400> SEQUENCE: 52

Asp Glu Val Asp
1

<210> SEQ ID NO 53
<211> LENGTH: 4

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Leu
<220> FEATURE:
<221> NAME/KEY: MOD_RES
<222> LOCATION: (4)..(4)
<223> OTHER INFORMATION: Asp-aldehyde

<400> SEQUENCE: 53

Leu Glu His Asp
1

<210> SEQ ID NO 54
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ac-Leu
<220> FEATURE:
<221> NAME/KEY: MOD_RES
<222> LOCATION: (4)..(4)
<223> OTHER INFORMATION: Asp-chloromethylketone

<400> SEQUENCE: 54

Leu Glu His Asp
1

<210> SEQ ID NO 55
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Carbobenzoxy-Leu
<220> FEATURE:
<221> NAME/KEY: MOD_RES
<222> LOCATION: (4)..(4)
<223> OTHER INFORMATION: Asp-fluoromethylketone

<400> SEQUENCE: 55

Leu Glu His Asp
1

<210> SEQ ID NO 56
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
agcacaggac acatcagttg g                                           21
```

```
<210> SEQ ID NO 57
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
cttgaggcag tagttcttgg tg                                          22
```

METHODS AND COMPOSITIONS FOR PRESERVING PHOTORECEPTOR AND RETINAL PIGMENT EPITHELIAL CELLS

CROSS-REFERENCE TO RELATED APPLICATIONS

This application is a continuation of U.S. patent application Ser. No. 13/642,887, filed Feb. 14, 2013, which is the national stage of International (PCT) Patent Application No. PCT/US2011/033704, filed Apr. 23, 2011, which claims the benefit of and priority to U.S. Provisional Application No. 61/327,476, filed Apr. 23, 2010; U.S. Provisional Application No. 61/405,003, filed Oct. 20, 2010; U.S. Provisional Application No. 61/409,055, filed Nov. 1, 2010; U.S. Provisional Application No. 61/414,862, filed Nov. 17, 2010; U.S. Provisional Application No. 61/472,153, filed Apr. 5, 2011; and U.S. Provisional Application No. 61/472,144, filed Apr. 5, 2011, the disclosure of each of which is hereby incorporated by reference in its entirety.

GOVERNMENT FUNDING

The work described in this application was sponsored, in part, by the National Eye Institute under Grant No. EY14104. The United States Government has certain rights in the invention.

FIELD OF THE INVENTION

The field of the invention relates generally to methods and compositions for preserving the viability of photoreceptor cells and/or retinal pigment epithelial cells, for example, in a subject affected with an ocular condition wherein a symptom of the ocular condition is loss of photoreceptor cell viability and/or retinal pigment epithelial cell viability, e.g., age-related macular degeneration (AMD), retinitis pigmentosa (RP), or a retinal detachment. More particularly, the invention relates to the use of a necrosis inhibitor, e.g., a RIP kinase inhibitor, e.g., a necrostatin, either alone or in combination with an apoptosis inhibitor, e.g., a pan-caspase inhibitor, for preserving the viability of photoreceptor and/or retinal pigment epithelial cells during the treatment of the ocular disorder.

BACKGROUND OF THE INVENTION

The retina is a delicate neural tissue lining the back of the eye that converts light stimuli into electric signals for processing by the brain. Ocular disorders affecting the retina, including, for example, retinal detachment, AMID, and RP can lead to vision loss and blindness. Early detection and treatment are critical in correcting problems before vision is lost or in preventing further deterioration of vision.

Photoreceptor death after retinal detachment ("RD") is a major cause of permanent visual loss in various ocular diseases. During retinal detachment, the entire retina or a portion of the retina becomes dissociated from the underlying retinal pigment epithelium and choroid. As a result, the sensitive photoreceptor cells disposed in the detached portion of the retina become deprived of their normal supply of blood and nutrients. If untreated, the retina or, more particularly, the sensitive photoreceptor cells disposed within the retina die causing partial or even complete blindness. Physical separation of photoreceptors from the underlying retinal pigment epithelium occurs in age-related macular degeneration (Dunaief J L et al. (2002) ARCH. OPHTHALMOL. 120:1435-1442), diabetic retinopathy (Barber A J et al. (1998) J. CLIN. INVEST. 102:783-791), retinopathy of prematurity (Fulton A B et al. (2001) ARCH. OPHTHALMOL. 119:499-505), as well as rhegmatogenous (caused by a break in the retina), serous or tractional retinal detachment (Cook B et al. (1995) INVEST. OPHTHALMOL. VIS. SCI. 36:990-996; Arroyo et al. (2005) AM. J. OPHTHALMOL. 139:605-610). Although surgery may be carried out to reattach the retina, only two-fifths of patients with retinal detachment involving the macula, a region essential for central vision, recover 20/40 or better vision due to photoreceptor death (Arroyo et al. (2005) AM. J. OPHTHALMOL. 139:605-610; Campo et al. (1999) OPHTHALMOLOGY 106:1811-1815). Identification of the mechanisms that underlie photoreceptor death is critical to developing new treatment strategies for these diseases.

Age-related macular degeneration is the leading cause of irreversible vision loss in the developed world affecting approximately 15% of individuals over the age of 60. Macular degeneration is categorized as either dry (atrophic) or wet (neovascular). The dry form is more common than the wet, with about 90% of AMD patients diagnosed with dry AMD. In the dry form, there is a breakdown or thinning of the retinal pigment epithelial cells (RPE) in the macula, hence the term "atrophy." These RPE cells are important to the function of the retina, as they metabolically support the overlying photoreceptors. AMD is a challenging disease for both patients and doctors because there are very few treatment options. Current therapies, including laser photocoagulation, photodynamic therapy, and anti-angiogenic therapeutics have had mixed results, and, in certain instances, have caused deleterious side effects. A need therefore exists for a treatment that reduces or limits the effects of macular degeneration.

Retinitis pigmentosa (RP) is a group of genetic eye conditions that leads to incurable blindness. Though the majority of mutations target photoreceptors, some affect RPE cells directly. Together, these mutations affect such processes as molecular trafficking between photoreceptors and RPE cells and phototransduction, for example. Currently, there is no cure for RP.

Apoptosis and necrosis represent two different mechanisms of cell death. Apoptosis is a highly regulated process involving the caspase family of cysteine proteases, and characterized by cellular shrinkage, chromatin condensation, and DNA degradation. In contrast, necrosis is associated with cellular and organelle swelling and plasma membrane rupture with ensuing release of intracellular contents and secondary inflammation (Kroemer G et al. (2009) CELL DEATH DIFFER. 16:3-11). Necrosis has been considered a passive, unregulated form of cell death; however, recent evidence indicates that some necrosis can be induced by regulated signal transduction pathways such as those mediated by receptor interacting protein (RIP) kinases, especially in conditions where caspases are inhibited or cannot be activated efficiently (Golstein P & Kroemer G (2007) TRENDS BIOCHEM. SCI. 32:37-43; Festjens N et al. (2006) BIOCHIM. BIOPHYS. ACTA 1757:1371-1387). Stimulation of the Fas and TNFR family of death domain receptors (DRs) is known to mediate apoptosis in most cell types through the activation of the extrinsic caspase pathway. In addition, in certain cells deficient for caspase-8 or treated with pan-caspase inhibitor Z-VAD, stimulation of death domain receptors (DR) causes a RIP-1 kinase dependent programmed necrotic cell death instead of apoptosis (Holler N et al. (2000) NAT. IMMUNOL. 1:489-495; Degterev A et al. (2008) NAT. CHEM. BIOL. 4:313-321). This novel mechanism of cell death is termed "programmed necrosis" or "necroptosis" (Degterev A et al. (2005) NAT. CHEM. BIOL. 1:112-119).

Receptor Interacting Protein kinase 1 (RIP-1) is a serine/threonine kinase that contains a death domain and forms a death signaling complex with the Fas-associated death domain and caspase-8 in response to death receptor (DR) stimulation (Festjens N et al. (2007) CELL DEATH DIFFER. 14:400-410). During death domain receptor-induced apoptosis, RIP-1 is cleaved and inactivated by caspase-8, the process of which is prevented by caspase inhibition (Lin Y et al. (1999) GENES. DEV. 13:2514-2526). It has been unclear how RIP-1 kinase mediates programmed necrosis, but recent studies revealed that the expression of RIP-3 and the RIP-1-RIP-3 binding through the RIP homotypic interaction motif is a prerequisite for RIP-1 kinase activation, leading to reactive oxygen species (ROS) production and necrotic cell death (He S et al. (2009) CELL 137:1100-1111; Cho Y S et al. (2009) CELL 137:1112-1123; Zhang D W et al. (2009) SCIENCE 325:332-336).

There is still an ongoing need to minimize or eliminate photoreceptor and/or retinal pigment epithelial cell death in certain ocular disorders, e.g., in AMD, RP, and retinal detachment. It is contemplated that minimizing photoreceptor and/or retinal pigment epithelial cell death will reduce the loss of vision or the loss of visual function associated with these various disorders.

SUMMARY OF THE INVENTION

The invention is based, in part, on the discovery that a necrosis inhibitor, e.g., RIP kinase inhibitor, e.g., a necrostatin, e.g., necrostatin-1, can be used to reduce or prevent the loss of photoreceptor and/or retinal pigment epithelial cell viability, especially when the necrosis inhibitor is combined with an apoptotic inhibitor (e.g., a pan-caspase inhibitor, e.g., Z-VAD and/or IDN-6556). It was previously understood that photoreceptor cell death associated with AMD, RP, and retinal detachment was primarily caused by apoptosis. However, studies have shown that the administration of Z-VAD, a pan-caspase inhibitor, fails to prevent photoreceptor loss in these conditions. The studies described hereinbelow indicate that, in the presence of an apoptosis inhibitor (e.g., a pan-caspase inhibitor), photoreceptors die by necrosis, including necroptosis (or programmed necrosis). These studies show that programmed necrosis is a critical mechanism for ocular conditions wherein a symptom of the condition is the loss of photoreceptor cell viability in the presence of a pan-caspase inhibitor. As a result, it is possible to reduce the loss of visual function associated with an ocular disorder, in particular while the ocular disorder is being treated, by reducing the loss of photoreceptor viabilabilty and/or retinal pigment epithelial cell viability In one aspect, the invention provides a method preserving the visual function of an eye of a subject with an ocular condition, wherein a symptom of the ocular condition is the loss of photoreceptor cell viability in the retina of the eye with the condition. The method comprises (a) administering to the eye of the subject an effective amount of a necrostatin and an effective amount of an apoptosis inhibitor thereby preserving the viability of the photoreceptor cells disposed within the retina of the eye, and (b) then measuring the visual function (e.g., visual acuity) of the eye after the administration of the necrosis inhibitor and the apoptosis inhibitor. After administration of the necrosis inhibitor and the apoptosis inhibitor the visual function (e.g., visual acuity) of the eye may be preserved or improved relative to the visual function of the eye prior to administration of the necrosis inhibitor and the apoptosis inhibitor.

The ocular condition may be a condition selected from the group consisting of AMD, RP, macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. AMD may be the neovascular or the dry form of AMD. Retinal detachment may be a rhegmatogenous, a serous, or a tractional retinal detachment.

In another aspect, the invention provides a method of preserving the viability of retinal pigment epithelial (RPE) cells within the retina of a subject with an ocular condition, wherein a symptom of the ocular condition is the loss of retinal pigment epithelial cells in the retina of the eye with the condition. The method comprises administering to the eye of the subject an effective amount of a necrosis inhibitor and an apoptosis inhibitor thereby preserving the viability of the retinal pigment epithelial cells. The ocular condition may be selected from the group consisting of AMD, BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE), and other uveitis disorders.

In another aspect, the invention provides a method of preserving the viability of photoreceptor cells disposed within a retina of a subject with an ocular condition selected from the group consisting of AMD, RP, macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. The method comprises administering to the eye an effective amount of a necrosis inhibitor and an effective amount of an apoptosis inhibitor thereby to preserve the viability of the photoreceptor cells disposed within the retina of the subject with a condition.

In another aspect, the invention provides a method of preserving the viability of photoreceptor cells disposed within a retina of a mammalian eye following retinal detachment. The method comprises administering a necrostatin and an apoptosis inhibitor to the eye in which a region of the retina has been detached in amounts sufficient to preserve the viability of photoreceptor cells disposed within the region of the detached retina. When necrostatin-1 is the only necrostatin administered, the region is exposed to a final concentration of necrostatin-1 in the eye greater than about 100 µM.

The prevention of photoreceptor death following retinal detachment by co-administration of an apoptotic inhibitor and a necrostatin, e.g., necrostatin-1, at concentrations that exceed 100 µM was surprising because it had been believed that concentrations of necrostatin-1 exceeding 100 µM were toxic and, therefore, could not be administered at such a dosage. Moreover, it was an unexpected finding that the combination of a necrostatin, e.g., necrostatin-1, and a pan-caspase inhibitor, e.g., Z-VAD, achieved a synergistic effect in reducing photoreceptor cell death following retinal detachment compared to either drug alone.

In certain embodiments, the retinal detachment may be a rhegmatogenous retinal detachment, tractional retinal detachment, or serous retinal detachment. In other embodiments, the retinal detachment may occur as a result of a retinal tear, retinoblastoma, melanoma or other cancers, diabetic retinopathy, uveitis, choroidal neovascularization, retinal ischemia, pathologic myopia, or trauma.

In another aspect, the invention provides a method of preserving visual function of an eye of a subject with an ocular condition selected from the group consisting of AMD, RP, macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity, wherein a symptom of the ocular condition is the loss of photoreceptor cells viability in the retina of the eye. The method comprises reducing the production and/or activity of a RIP-1 kinase and/or RIP-3 kinase in the eye thereby preserving the viability of the photoreceptor cells disposed with the retina of the eye. In certain embodiments, the reduction in the production or activity of the RIP-1 kinase and/or the RIP-3 kinase can achieved by administering an effective amount of RIP kinase (RIPK) inhibitor, e.g., a necrostatin.

In another aspect, the invention provides a method of preserving the visual function of an eye of a subject with an ocular condition, wherein a symptom of the ocular condition is the loss of photoreceptor cell viability and/or RPE viability in the retina of the eye. The method comprises (a) reducing the production or activity of a RIP-1 kinase and/or a RIP-3 kinase in the eye thereby to preserve the viability of the photoreceptor cells and/or RPE cells disposed within the retina of the eye; and (b), after treatment, measuring visual function (e.g., visual acuity) of the eye. In certain embodiments, the reduction in the production or activity of the RIP-1 kinase and/or the RIP-3 kinase can be achieved by administering an effective amount of RIPK inhibitor, e.g., a necrostatin. After administration of the RIPK inhibitor the visual function of the eye may be preserved or improved relative to the visual function of the eye prior to administration of the RIPK inhibitor.

In another aspect, the invention provides a combination of a necrosis inhibitor (e.g., a RIPK inhibitor, e.g., a necrostatin) and an apoptosis inhibitor (e.g., a pan-caspase inhibitor, e.g., Z-VAD or IDN-6556), for use in preserving visual function of an eye of a subject with certain ocular conditions described herein, wherein a symptom of the ocular condition is the loss of photoreceptor cell and/or RPE cell viability in the retina of the eye with the condition.

In another aspect, the invention provides a combination of a necrosis inhibitor (e.g., a RIPK inhibitor, e.g., a necrostatin) and an apoptosis inhibitor (e.g., a pan-caspase inhibitor, e.g., Z-VAD or IDN-6556), for use in preserving the viability of photoreceptor cells disposed in the retina of an eye with an ocular condition, wherein a symptom of the ocular condition is the loss of photoreceptor cell viability in the retina of the eye with the condition. The ocular condition may be selected from AMD, RP, macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity.

In another aspect, the invention provides a combination of a necrosis inhibitor (e.g., a RIPK inhibitor, e.g., a necrostatin) and an apoptosis inhibitor (e.g., a pan-caspase inhibitor, e.g., Z-VAD or IDN-6556), for use in preserving the viability of photoreceptor cells disposed in the retina of an eye following retinal detachment, provided that when necrostatin-1 is the only necrostatin administered, the region of the retina that has been detached is exposed to a final concentration of necrostatin-1 in the eye greater than 100 µM.

In another aspect, the invention provides a combination of a necrosis inhibitor (e.g., a RIPK inhibitor, e.g., a necrostatin) and an apoptosis inhibitor (e.g., a pan-caspase inhibitor, e.g., Z-VAD or IDN-6556), for use in preserving the viability of retinal pigment epithelial cells disposed in the retina of an eye with an ocular condition, wherein a symptom of the ocular condition is the loss of retinal pigment epithelial cell viability in the retina of the eye with the condition. The ocular condition may be selected from the group consisting of AMD, BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE), and other uveitis disorders.

In each of the foregoing methods, the necrosis inhibitor can be a RIP kinase inhibitor, for example, a necrostatin. In certain embodiments of the foregoing methods, the necrostatin is necrostatin-1, necrostatin-2, necrostatin-3, necrostatin-4, necreostatin-5, necrostatin-7, or a combination thereof.

In certain embodiments when a necrostatin is administered, the necrostatin is administered to provide a final concentration of necrostatin in the eye greater than about 100 µM. For example, the final concentration of necrostatin in the eye may range from about 150 µM to about 1000 µM, from about 200 µM to about 800 µM or from about 200 µM to about 600 µM. In certain embodiments, the final concentration of necrostatin in the eye is about 400 µM. In other embodiments when a necrostatin is administered, from about 0.05 mg to about 2 mg, 0.1 mg to about 1 mg, from about 0.2 mg to about 1 mg, or from about 0.2 mg to about 0.8 mg, of necrostatin can be administered locally to the eye of a mammal. In an exemplary embodiment, about 0.5 mg of necrostatin can be administered locally to the eye of a mammal.

In certain embodiments when a pan-caspase inhibitor is administered, the pan-caspase inhibitor is administered to provide a final concentration of the pan-caspase inhibitor in eye greater than about 100 µM. For example, the final concentration of pan-caspase inhibitor in the eye may range from about 150 µM to about 500 µM or from about 200 µM to about 400 µM. In certain embodiments, the final concentration of the pan-caspase inhibitor in the eye is about 300 µM. Exemplary pan-caspase inhibitors include zVAD, IDN-6556 or a combination thereof. In other embodiments, from about 0.05 mg to about 1.5 mg, from about 0.15 mg to about 1.5 mg, from about 0.2 mg to about 1 mg, from about 0.2 mg to about 0.8 mg, from about 0.4 mg to about 1 mg, or from about 0.5 mg to about 0.8 mg, of the pan-caspase inhibitor can be administered locally to the eye of a mammal. In an exemplary embodiment, about 0.7 mg of a pan-caspase inhibitor can be administered locally to the eye of a mammal.

The necrosis inhibitor, e.g., a necrostatin, and/or the apoptosis inhibitor may be administered to the eye by intraocular, intravitreal, subretinal or trasscleral administration. The necrosis inhibitor, e.g., a necrostatin, and/or the apoptosis inhibitor may be solubilized in a viscoelastic carrier that is introduced into the eye. In other embodiments, the necrosis inhibitor, e.g., a necrostatin, and/or the apoptosis inhibitor may be administered systemically.

It is understood that the necrosis inhibitor, e.g., a necrostatin, and/or the apoptosis inhibitor may be administered sequentially or simultaneously. The necrosis inhibitor, e.g., a necrostatin, and the apoptosis inhibitor may be administered in the same or different carriers.

In certain embodiments, when the ocular condition is a retinal detachment, the necrostatin and/or the apoptosis inhibitor may be administered to the subject prior to reattachment and/or after reattachment of the retina or a region of the retina that has become detached.

In each of the foregoing methods and compositions, the necrostatin can be selected from one or more of the following necrostatins. For example, in certain embodiments, the necrostatin is a Nec-1 related compound of Formula I:

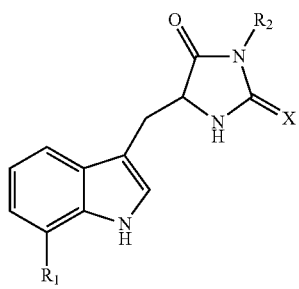

(I)

or a pharmaceutically acceptable salt, ester, or prodrug thereof, wherein

X is O or S;

$R_1$ is hydrogen, $C_1$-$C_6$alkyl, $C_1$-$C_6$alkoxyl, or halogen; and $R_2$ is hydrogen or $C_1$-$C_6$alkyl.

In each of the foregoing methods and compositions, the necrostatin can be a Nec-1 related compound of Formula I-A:

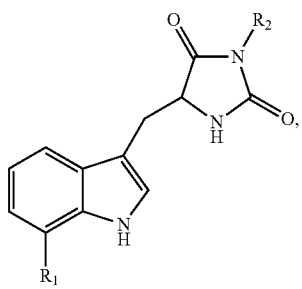

(I-A)

or a pharmaceutically acceptable salt, ester, or prodrug thereof, or optical isomers or racemic mixtures thereof, wherein $R_1$ is H, alkyl, alkoxyl, or a halogen and $R_2$ is H or an alkyl.

In each of the foregoing methods and compositions, the necrostatin can be a Nec-1 related compound of Formula I-B:

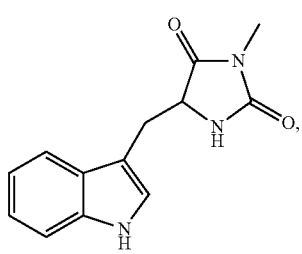

(I-B)

or a pharmaceutically acceptable salt, ester, or prodrug thereof.

In each of the foregoing methods and compositions, the necrostatin can be a Nec-1 related compound of Formula I-C:

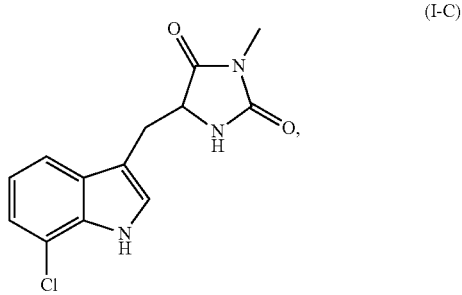 [SMILES: CN1C(=O)NC(Cc2c[nH]c3c(Cl)cccc23)C1=O]

(I-C)

or a pharmaceutically acceptable salt, ester, or prodrug thereof.

In each of the foregoing methods and compositions, the necrostatin can be a Nec-1 related compound of Formula I-D:

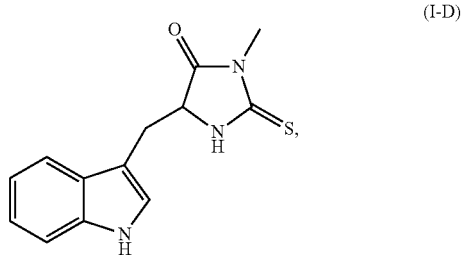 [SMILES: CN1C(=O)C(Cc2c[nH]c3ccccc23)NC1=S]

(I-D)

or a pharmaceutically acceptable salt, ester, or prodrug thereof.

In each of the foregoing methods and compositions, the necrostatin can be a Nec-1 related compound of Formula I-E:

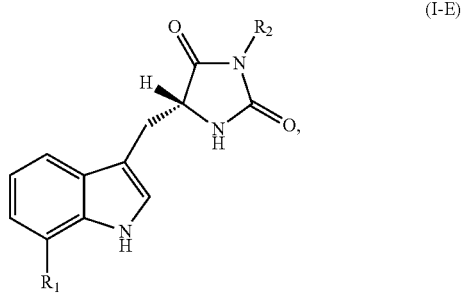

(I-E)

or a pharmaceutically acceptable salt, ester, or prodrug thereof, wherein $R_1$ is H, alkyl, alkoxyl, or a halogen (for example, F, Cl, Br or I) and $R_2$ is H or an alkyl.

In each of the foregoing methods and compositions, the necrostatin can be a Nec-1 related compound of Formula I-F:

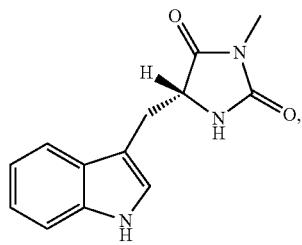

(I-F)

or a pharmaceutically acceptable salt, ester, or prodrug thereof.

In each of the foregoing methods and compositions, the necrostatin can be a Nec-1 related compound of Formula I-G:

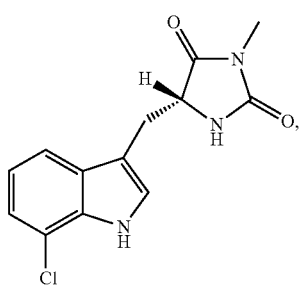

(I-G)

or a pharmaceutically acceptable salt, ester, or prodrug thereof.

In each of the foregoing methods and compositions, the necrostatin can be a Nec-2 related compound of Formula II:

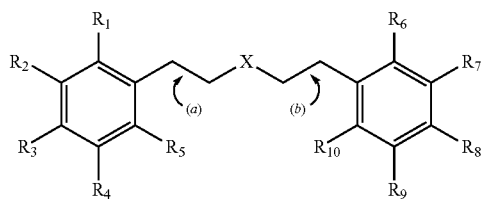

(II)

or a pharmaceutically acceptable salt, ester, or prodrug thereof, wherein:

X is —$CH_2$—, —C(H)($R_{14}$)—, —C(=S)—, —C(=NH)—, or —C(O)—;

$R_1$, $R_2$, $R_3$, $R_4$, $R_5$, $R_6$, $R_7$, $R_8$, $R_9$, and $R_{10}$ each represent independently hydrogen, acyl, acetyl, alkyl, halogen, amino, $C_1$-$C_6$alkoxyl, nitro, —C(O)$R_{12}$, —C(S)$R_{12}$, —C(O)O$R_{12}$, —C(O)N$R_{12}R_{13}$, —C(S)N$R_{12}R_{13}$, or —S($O_2$)$R_{12}$;

$R_{11}$ is hydrogen, acyl, acetyl, alkyl, or acylamino;

$R_{12}$ and $R_{13}$ each represent independently hydrogen, an optionally substituted alkyl, an optionally substituted aryl, an optionally substituted heteroaryl, an optionally substituted aralkyl, or an optionally substituted heteroaralkyl;

$R_{14}$ is acyl, acetyl, alkyl, halogen, amino, acylamino, nitro, —S$R_{11}$, —N($R_{11}$)$_2$, or —O$R_{11}$;

the bond indicated by (a) can be a single or double bond; and the bond indicated by (b) can be a single or double bond.

In each of the foregoing methods and compositions, the necrostatin can be a Nec-2 related compound of Formula IIA:

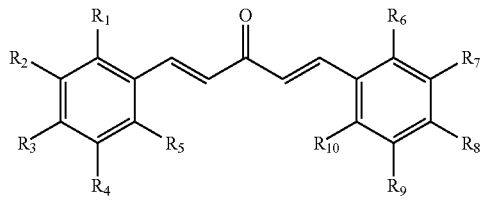

(II-A)

or a pharmaceutically acceptable salt thereof, wherein:

$R_1$, $R_2$, $R_5$, $R_6$, $R_7$, and $R_{10}$ each represent independently hydrogen, alkyl, halogen, amino, or methoxyl; and $R_3$, $R_4$, $R_8$, and $R_9$ are $C_1$-$C_6$alkoxyl.

In each of the foregoing methods and compositions, the necrostatin can be a Nec-3 related compound of Formula III:

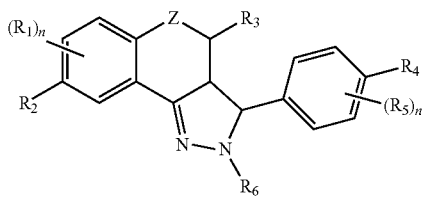

(III)

or a pharmaceutically acceptable salt, ester, or prodrug thereof, wherein:

Z is —$CH_2$—, —$CH_2CH_2$—, —O—, —S—, —S(O)—, —S($O_2$)—, or —N($R_7$)—;

$R_1$, $R_3$, and $R_5$ each represent independently for each occurrence hydrogen, halogen, hydroxyl, amino, $C_1$-$C_6$alkyl, $C_1$-$C_6$alkoxy, $C_1$-$C_6$alkoxy-$C_1$-$C_6$alkyl, $C_1$-$C_6$alkanoyl, $C_1$-$C_6$alkylsulfinyl, $C_1$-$C_6$alkylsulfonyl, $C_1$-$C_6$alkylsulfonyl-$C_1$-$C_6$alkyl, aryl, aralkyl, heterocycloalkyl, heteroaryl, or heteroaralkyl;

$R_2$ and $R_4$ are $C_1$-$C_6$alkoxy;

$R_6$ is —C(O)$R_8$, —C(S)$R_8$, —C(O)O$R_8$, —C(O)N$R_8R_9$, —C(S)N$R_8R_9$, —C(NH)$R_8$, or —S($O_2$)$R_8$;

$R_7$ is alkyl, aralkyl, or heteroaralkyl;

$R_8$ and $R_9$ each represent independently hydrogen, $C_1$-$C_6$alkyl, heteroalkyl, aryl, heteroaryl, aralkyl, or heteroaralkyl; and n represents independently for each occurrence 0, 1, or 2.

In each of the foregoing methods and compositions, the necrostatin can be a Nec-4 related compound of Formula IV:

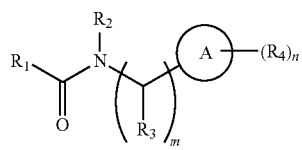

(IV)

or a pharmaceutically acceptable salt, ester, or prodrug thereof, wherein:

R₁ is

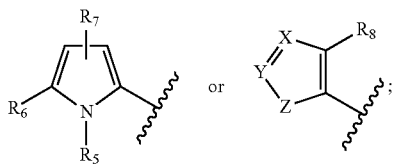

R₂ and R₃ each represent independently for each occurrence hydrogen or methyl;

R₄ represents independently for each occurrence halogen, hydrogen, C₁-C₆alkyl, C₂-C₆alkenyl, or C₂-C₄alkynyl;

R₅ is C₁-C₄alkyl;

R₆ is hydrogen, halogen, or —CN;

R₇ is hydrogen or C₁-C₄alkyl;

R₈ is C₁-C₆alkyl, or R₈ taken together with R₉, when present, forms a carbocyclic ring;

R₉ is hydrogen or C₁-C₆alkyl, or R₉ taken together with R₈ forms a carbocyclic ring;

R₁₀ is hydrogen or C₁-C₆alkyl;

A is phenylene or a 5-6 membered heteroarylene;

X is N or —C(R₉)—;

Y is N or —C(R₁₀)—;

Z is S or O; and m and n each represent independently 1, 2, or 3.

In each of the foregoing methods and compositions, the necrostatin can be a Nec-4 related compound of Formula IV-A:

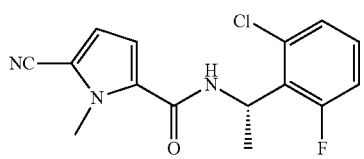 [SMILES: C[C@H](NC(=O)c1ccc(C#N)n1C)c1c(F)cccc1Cl]

or a pharmaceutically acceptable salt thereof.

In each of the foregoing methods and compositions, the necrostatin can be a Nec-5 related compound of Formula V:

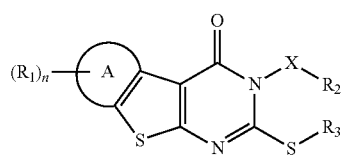

(V)

or a pharmaceutically acceptable salt, ester, or prodrug thereof, wherein:

A is a saturated or unsaturated 5-6 membered carbocyclic ring;

X is a bond or C₁-C₄alkylene;

R₁ is C₁-C₆ alkyl, halogen, hydroxyl, C₁-C₆alkoxyl, —N(R₄)₂, —C(O)R₄, CO₂R₄, or C(O)N(R₄)₂;

R₂ is

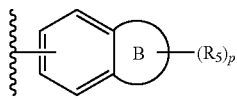

or

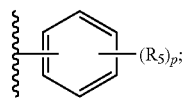

R₃ is —C₁-C₆alkylene-CN, —CN, C₁-C₆alkyl, or C₂-C₆alkenyl; R₄ represents independently for each occurrence hydrogen, C₁-C₆alkyl, aryl, or aralkyl;

R₅ represents independently for each occurrence C₁-C₆alkyl, halogen, hydroxyl, C₁-C₆alkoxyl, —N(R₄)₂, —C(O)R₄, CO₂R₄, or C(O)N(R₄)₂;

B is a 5-6 membered heterocyclic or carbocyclic ring; and n and p each represent independently 0, 1, or 2.

In each of the foregoing methods and compositions, the necrostatin can be a Nec-5 related compound of Formula V-A:

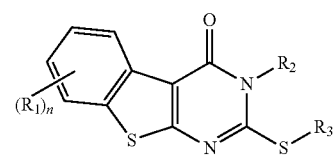

(V-A)

or a pharmaceutically acceptable salt, ester, or prodrug thereof, wherein:

R₁ is C₁-C₆alkyl, halogen, hydroxyl, C₁-C₆alkoxyl, or —N(R₄)₂;

R₂ is

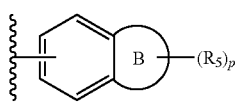

or

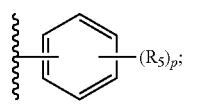

R₃ is —C₁-C₆alkylene-CN;

R₄ represents independently for each occurrence hydrogen, C₁-C₆alkyl, aryl, or aralkyl;

R₅ represents independently for each occurrence C₁-C₆alkyl, halogen, hydroxyl, C₁-C₆alkoxyl, —N(R₄)₂, —C(O)R₄, CO₂R₄, or C(O)N(R₄)₂;

B is a 5-6 membered heterocyclic or carbocyclic ring; and n and p each represent independently 0, 1, or 2.

In each of the foregoing methods and compositions, the necrostatin can be a Nec-7 related compound of Formula VII:

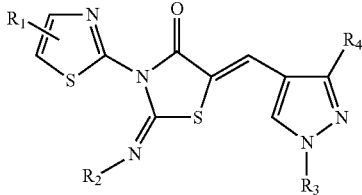

or a pharmaceutically acceptable salt, ester, or prodrug thereof, wherein:

$R_1$, $R_2$, and $R_3$ each represent independently hydrogen or $C_1$-$C_4$alkyl;

$R_4$ is

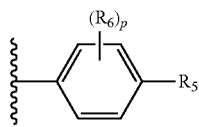

or

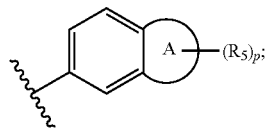

$R_5$ and $R_6$ each represent independently for each occurrence halogen, $C_1$-$C_6$alkyl, hydroxyl, $C_1$-$C_6$alkoxyl, —N(R_7)_2, —NO_2, —S—$C_1$-$C_6$alkyl, —S-aryl, —SO_2—$C_1$-$C_6$alkyl, —SO_2-aryl, —C(O)R_7, —CO_2R_7, —C(O)N(R_7)_2, heterocycloalkyl, aryl, or heteroaryl;

$R_7$ represents independently for each occurrence hydrogen, $C_1$-$C_6$alkyl, aryl, or aralkyl; or two occurrences of $R_7$ attached to the same nitrogen atom are taken together with the nitrogen atom to which they are attached to form a 3-7 membered heterocyclic ring;

A is a 5-6 membered heterocyclic ring; and p is 0, 1, or 2.

In each of the foregoing methods and compositions, the necrostatin can be a Nec-7 related compound of Formula VIII:

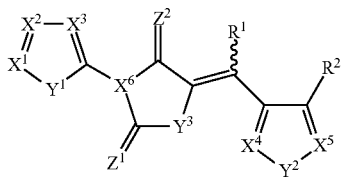

or a pharmaceutically acceptable salt, ester, or prodrug thereof, wherein:

each $X^1$, $X^2$, $X^3$, $X^4$, $X^5$, and $X^6$ is selected, independently, from N or $CR^{X1}$;

each $Y^1$, $Y^2$, and $Y^3$ is selected, independently, from O, S, $NR^{Y1}$, or $CR^{Y2}R^{Y3}$;

each $Z^1$ and $Z^2$ is selected, independently, from O, S, or $NR^{Z1}$;

each $R^{Y1}$ and $R^{Z1}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, optionally substituted heteroaryl, —C(=O)$R^{5A}$, —C(=O)O$R^{5A}$, or —C(=O)$NR^{5A}R^{6A}$;

each $R^{X1}$, $R^{Y2}$, and $R^{Y3}$ is selected, independently, from H, halogen, CN, NC, NO_2, N_3, OR^3, SR^3, $NR^3R^4$, —C(=O)$R^{5A}$, —C(=O)O$R^{5A}$, —C(=O)$NR^{5A}R^{6A}$, —S(=O)$R^{5A}$, —S(=O)_2$R^{5A}$, —S(=O)_2O$R^{5A}$, —S(=O)_2$NR^{5A}R^{6A}$, optionally substituted $C_{1-6}$alkyl, optionally substituted $C_{2-6}$alkenyl, optionally substituted $C_{2-6}$ alkynyl, optionally substituted cycloalkyl, optionally substituted heterocyclyl, optionally substituted aryl, or optionally substituted heteroaryl;

each $R^1$, $R^2$, $R^{5A}$, $R^{5B}$, $R^{6A}$, and $R^{6B}$ is selected from H, optionally substituted $C_{1-6}$ alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl; or $R^{5A}$ and $R^{6A}$, or $R^{5B}$ and $R^{6B}$ combine to form a heterocyclyl; and each $R^3$ and $R^4$ is selected from H, optionally substituted $C_{1-6}$ alkyl, optionally substituted cycloalkyl, optionally substituted heterocyclyl, optionally substituted aryl, optionally substituted heteroaryl, —C(=O)$R^{5B}$, —C(=S)$R^{5B}$, —C($NR^{6B}$)$R^{5B}$, —C(=O)O$R^{5B}$, —C(=O)$NR^{5B}R^{6B}$, —S(=O)$R^{5B}$, —S(=O)_2$R^{5B}$, —S(=O)_2O$R^{5B}$, or —S(=O)_2$NR^{5B}R^{6B}$. In certain embodiments when $R^1$ is H, $X^1$, $X^2$, and $X^4$ are each CH, $X^3$, $X^5$, and $X^6$ are each N, $Y^1$ and $Y^3$ are each S, $Y^2$ is NH, $Z^1$ is NH, and $Z^2$ is O, then $R^2$ is not 4-fluorophenyl.

In each of the foregoing methods and compositions, the necrostatin can be a Nec-4 related compound of Formula IX:

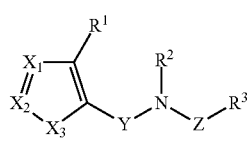

or a pharmaceutically acceptable salt, ester, or prodrug thereof, wherein:

$X_1$ and $X_2$ are, independently, N or $CR^4$;

$X_3$ is selected from O, S, $NR^5$, or —($CR^5$)_2;

Y is selected from C(O) or $CH_2$; and

Z is $(CR^6R^7)_n$;

$R^1$ is selected from H, halogen, optionally substituted $C_{1-6}$alkyl, or optionally substituted $C_{1-6}$cycloalkyl, or optionally substituted aryl;

$R^2$ is selected from H or optionally substituted $C_{1-6}$alkyl;

$R^3$ is optionally substituted aryl;

each $R^4$ is selected from H, halogen, carboxamido, nitro, cyano, optionally substituted $C_{1-6}$alkyl, or optionally substituted aryl;

$R^5$ is selected from H, halogen, optionally substituted $C_{1-6}$alkyl, or optionally substituted aryl;

each $R^6$ and $R^7$ is, independently, selected from H, optionally substituted $C_{1-6}$alkyl, or aryl; and n is 0, 1, 2, or 3. In certain embodiments, when $X_1$ and $X_2$ are N, $X_3$ is S, Y is C(O), Z is $CH_2$, $R^2$ is H, and $R^3$ is 2-chloro-6-fluoro-phenyl, then $R^1$ is not methyl.

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described herein.

FIG. 1B-D depict graphs and photographs that show the increase in RIP-3 (FIG. 1B) and RIP-1 (FIG. 1C) expression after retinal detachment, as determined by quantitative real-time PCR analysis, and by Western blot analysis (FIG. 1D).

FIG. 4A-C are photographs and graphs showing that necrostatin-1 (Nec-1) combined with Z-VAD prevents photoreceptor loss 3 and 5 days after retinal detachment.

FIG. 6A-F are graphs showing quantification of TUNEL-positive photoreceptors (FIGS. 6A, 6C and 6E) and ONL thickness ratio (FIGS. 6B, 6D and 6F) on day three after retinal detachment.

FIG. 7A-D are transmission electron microscope (TEM) photomicrographs and FIG. 7E is a graph depicting the involvement of programmed necrosis during retinal detachment induced photoreceptor death, wherein cells denoted as A represent apoptotic cells, and cells denoted as N represent necrotic cells.

FIG. 8A-D are photographs of PI staining (FIGS. 8A and 8C) and graphs showing quantification of PI-positive photoreceptors (FIGS. 8B and 8D) on day three after retinal detachment in retina treated with vehicle, Z-VAD or Z-VAD+Nec-1 in wild-type (FIGS. 8A and 8B) and RIP-3−/− retinas (FIGS. 8C and 8D).

FIG. 13A-B are graphs showing results from an ELISA for MCP-1 (FIG. 13A) and TNF-α (FIG. 13B) in retina without retinal detachment (n=5) and in retina three days after retinal detachment with treatment of vehicle (n=5), Z-VAD (n=5) or Z-VAD+Nec-1 (n=6).

(FIG. 15A) After retinal detachment, photoreceptor death is caused mainly by apoptosis. (FIG. 15B) Caspase inhibition by Z-VAD decreases apoptosis but promotes RIP-mediated programmed necrosis. (FIG. 15C) Blockade of both caspases and RIP kinases is essential for effective prevention of photoreceptor loss.

FIG. 18A is a graph showing quantitative real-time PCR analysis for TNF-α in control retina without retinal detachment (n=9) and in retina three days after retinal detachment with treatment of vehicle (n=9), Z-VAD (n=8) or Z-VAD+Nec-1 (n=9). *, P<0.05; **, P<0.01. FIG. 18B is a graph showing results from an ELISA for TNF-α in retina without retinal detachment (n=5) and in retina three days after retinal detachment with treatment of vehicle (n=5), Z-VAD (n=5) or Z-VAD+Nec-1 (n=6). FIG. 18C-D are a photograph and a graph showing DAPI staining (FIG. 18C) and quantification of the outer nuclear layer (ONL) thickness ratio (FIG. 18D) in detached retina treated with anti-TNF-α antibody or control antibody on day three after retinal detachment (n=4 each). *, P<0.05.

FIG. 25B provides graphs showing RIP-1 and RIP-3 expression in the retina of CX3CR1-/-CCL2-/- double knockout mice at 5 weeks (5 w) and 5 months (5M) of age.

Figure 26:
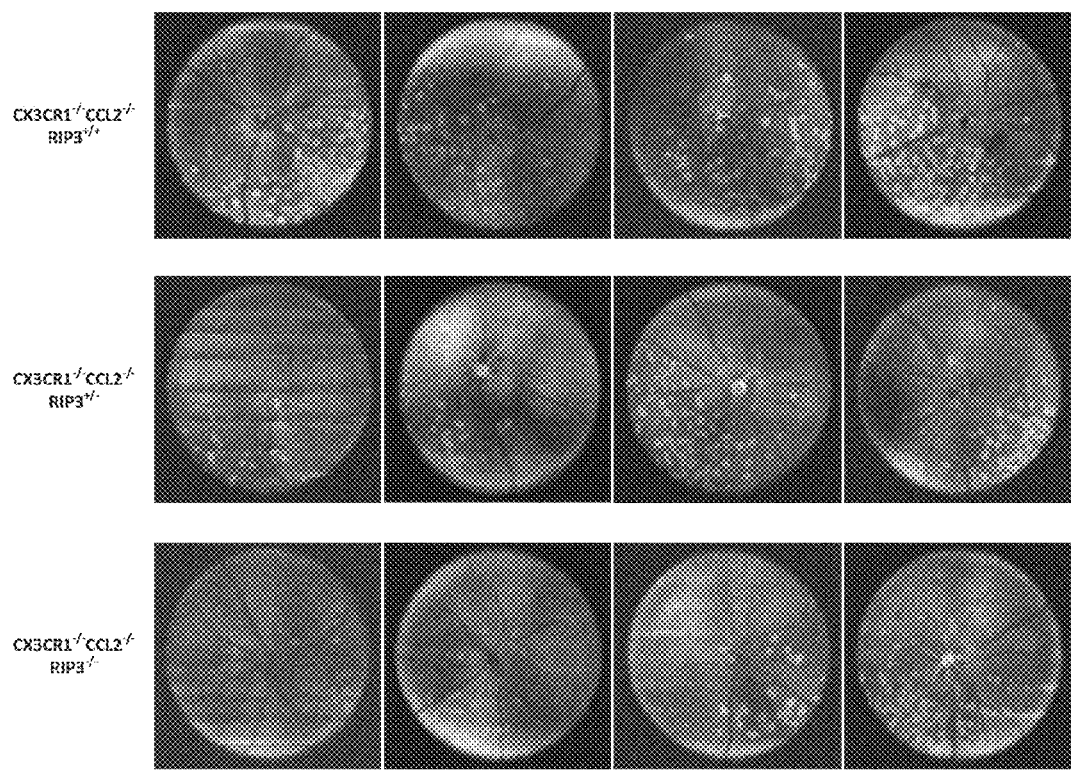

FIG. 26 provides photographs showing the development of drusen-like lesions in CX3CR1-/-CCL2-/-RIP-3+/+ knockout mice (first row), CX3CR1-/-CCL2-/- RIP-3+/- knockout mice (second row), and CX3CR1-/-CCL2-/- RIP-3-/- triple knockout mice (third row).

Figure 27:
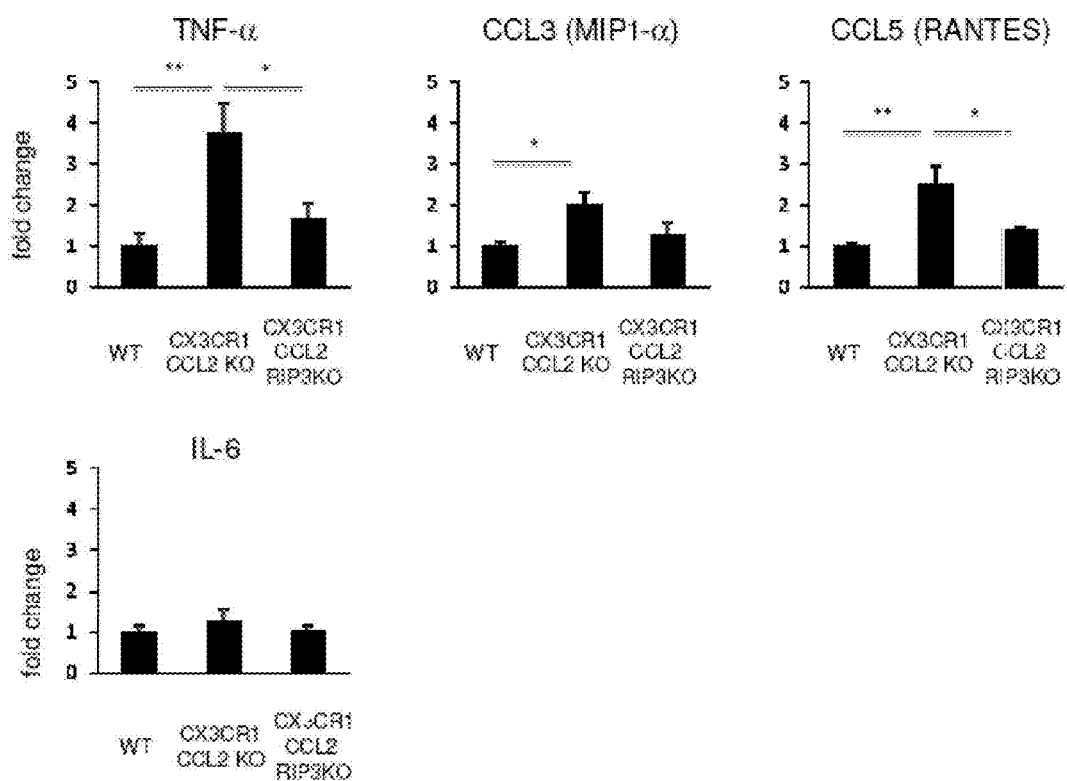

FIG. 27 provides graphs showing expression of various inflammatory cytokines in the retina of WT mice, CX3CR1-/-CCL2-/- double knockout mice, and CX3CR1-/-CCL2-/-RIP-3-/- triple knockout mice at 2 months of age.

Figure 28:
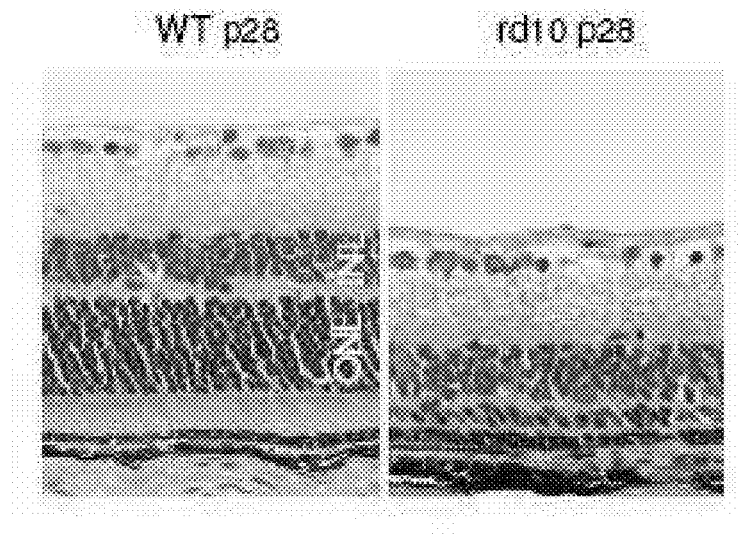

FIG. 28 provides photographs showing loss of photoreceptors and RPE in the ONL in rd10 mice at postnatal day 28.

Figure 29A:
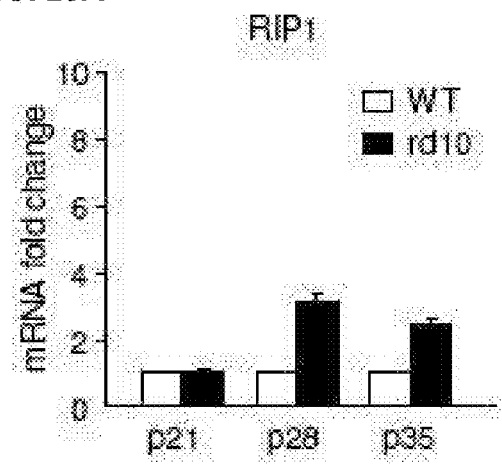
Figure 29B:
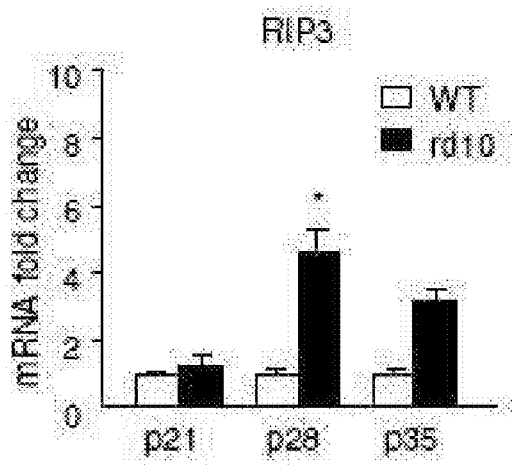

FIG. 29A-B are graphs showing RIP-1 and RIP-3 expression in the retina of rd10 mice at postnatal day 21, 28, and 35.

Figure 30A:
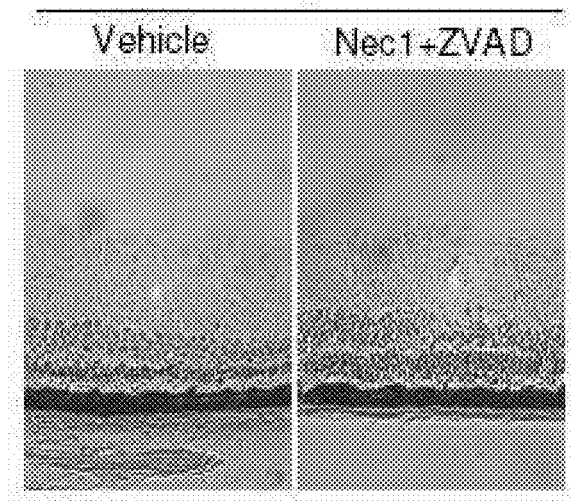
Figure 30B:
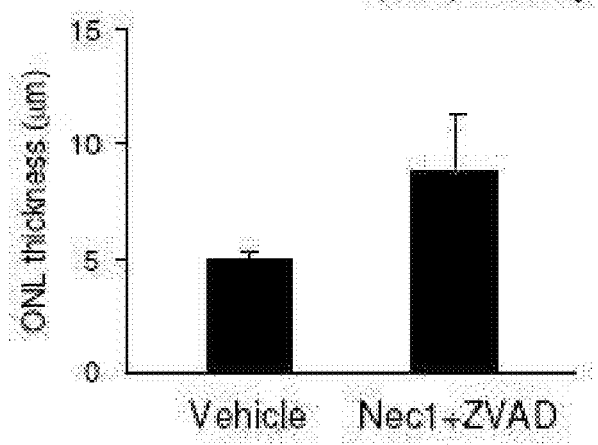

FIG. 30A-B are photographs and a graph showing ONL thickness in rd10 mice following Z-VAD+NEC-1 daily intraperitoneal injections from postnatal day 25 to postnatal day 28.

Figure 31A:
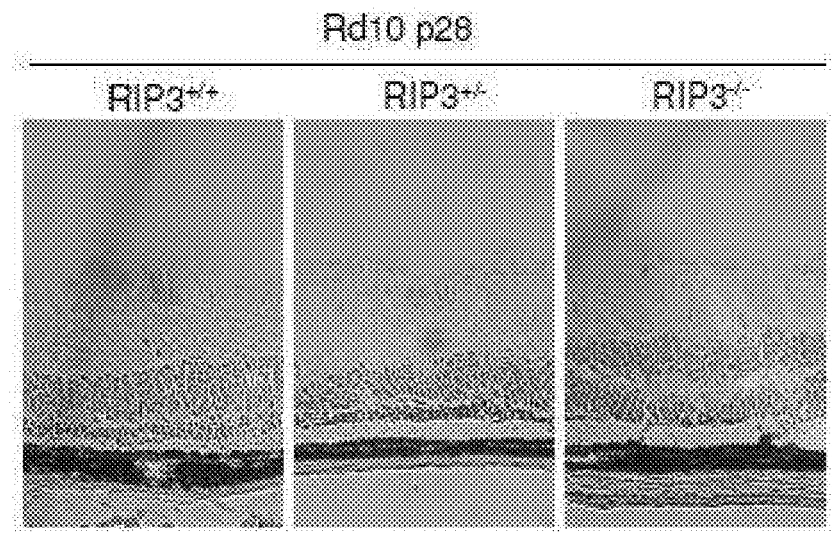
Figure 31B:
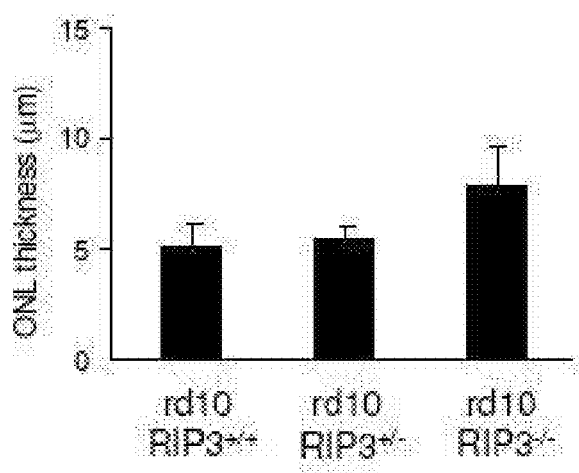

FIG. 31A-B are photographs and a graph showing ONL thickness in rd10 RIP-3 double mutant mice.

Figure 32A:
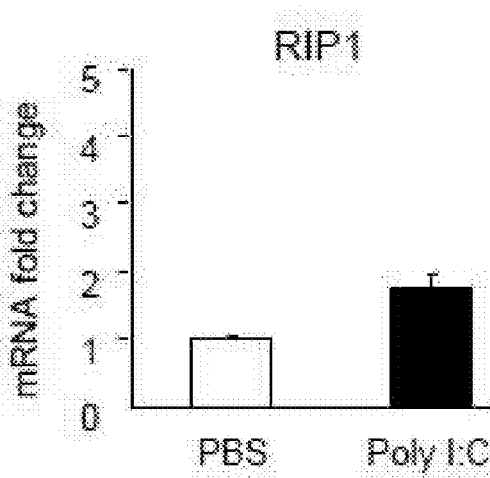
Figure 32B:
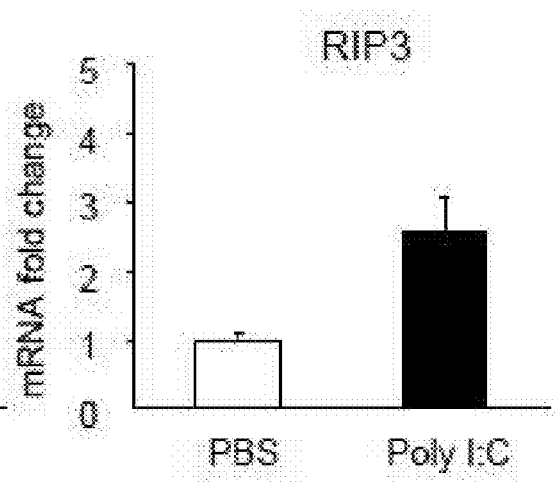

FIG. 32A-B are graphs showing RIP-1 (FIG. 32A) and RIP-3 (FIG. 32B) expression in poly I:C treated RPE cells.

Figure 33A:
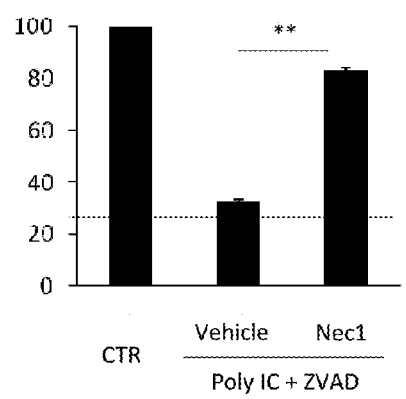
Figure 33B:
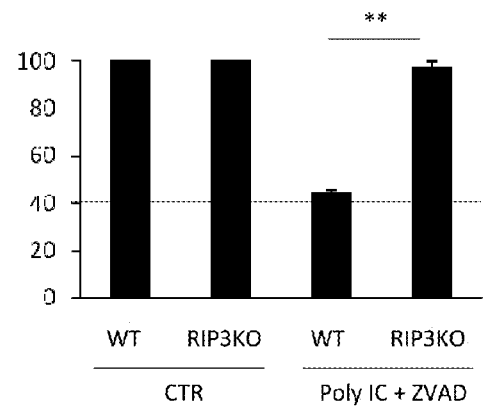

FIG. 33A is a graph showing the viability of RPE cells treated with poly I:C in combination with Z-VAD or Z-VAD+Nec1. FIG. 33B is a graph showing the viability of WT or RIP-3-/-RPE cells treated with poly I:C in combination with Z-VAD.

DETAILED DESCRIPTION

The invention relates to methods and composition for preserving the viability of photoreceptor cells and/or retinal pigment epithelial cells disposed within a retina of an eye of a subject with certain ocular conditions, wherein the viability of the photoreceptor cells and/or the retinal pigment epithelial cells are affected by the ocular disorder. As it result, using the methods and compositions described herein, it may be possible to preserve or improve visual function in the eye by maintaining photoreceptor viability and/or retinal pigment epithelial cell viability while the underlying ocular condition is being treated.

Figure 1A:
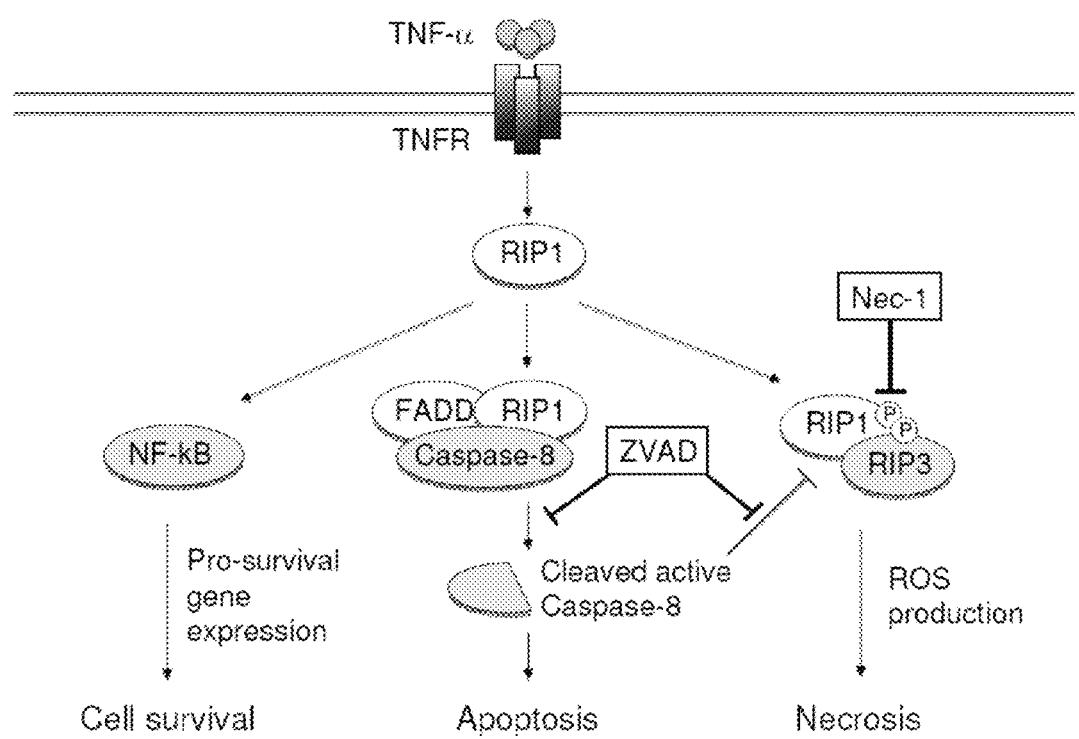
FIG. 1A provides a schematic representation of the RIP-1 signaling pathway.

As demonstrated herein, programmed necrosis appears to be a critical mechanism of photoreceptor death in certain ocular disorders, for example, AMD, RP, and following retinal detachment in the presence of an apoptosis inhibitor, e.g., a pan-caspase inhibitor. As depicted in FIG. 1A, there are two pathways for cell death—apoptosis and necrosis, which appear to be mediated by RIP-1, a serine/threonine kinase. RIP-1 can act on or modulate NF-κB to affect cell survival. RIP-1 can also form a complex with the Fas-associated death domain (FADD) and caspase-8 in response to death receptor stimulation to modulate the apoptotic pathway of cell death. In addition, RIP-1 can form a complex with RIP-3 to modulate the necrotic pathway of cell death. As shown in FIG. 1A, modulation of the apoptotic pathway (e.g., with a pan-caspase inhibitor, e.g., Z-VAD) can also affect the necrotic pathway.

The methods and compositions described herein are directed to therapies that target both the necrotic and apoptotic pathways of programmed cell death. In particular, the methods and compositions disclosed herein facilitate a combination therapy where a necrosis inhibitor, e.g, a necrostatin (e.g., necrostatin-1 or necrostatin-4), can be administered either alone or in combination (either sequentially or simultaneously) with an apoptosis inhibitor e.g., a pan-caspase inhibitor (e.g., Z-VAD or IDN-6556). In certain embodiments, the disclosed methods surprisingly use necrostatins at concentrations higher than those previously thought to be clinically tolerable. Moreover, it has been demonstrated that the combination of a necrostatin, e.g., necrostatin-1 or necrostatin-4, and a pan-caspase inhibitor, e.g., Z-VAD or IDN-6556, produce a superior effect, e.g., a synergistic effect in reducing photoreceptor cell death in AMD, RP and following retinal detachment, compared to either drug alone.

For convenience, certain terms in the specification, examples, and appended claims are collected in this section.

As used herein, the term "cell death" is understood to mean the death of a cell by either apoptosis or necrosis.

As used herein, the term "apoptosis" is understood to mean caspase-dependent cell death, which is characterized by any of the following properties: cell shrinkage, nuclear condensation, DNA fragmentation or membrane blebbing.

As used herein, the term "apoptosis inhibitor" is understood to mean any agent that, when administered to a mammal, reduces apoptotic cell death in photoreceptor and/or RPE cells. For example, it is understood that certain useful apoptosis inhibitors act by reducing or eliminating the activity of one or more members of the intrinsic or extrinsic or common apoptotic pathways. Furthermore, it is understood that an agent that either directly or indirectly affects the activity of one or more caspases (e.g., a pan-caspase inhibitor) is considered to be an apoptosis inhibitor. It is understood that a caspase inhibitor can affect the activity of a caspase either directly by modulating a specific caspase in the apoptotic pathway or indirectly by modulating a downstream caspase present in the apoptotic pathway.

As used herein, the term "pan-caspase inhibitor" is understood to mean a broad-spectrum caspase inhibitor that inhibits at least two, preferably at least three different caspases (e.g., caspase-1, caspase-2, caspase-3, caspase-4, caspase-5, caspase-6, caspase-7, caspase-8, caspase-9, caspase-10, caspase-11, caspase-12, caspase-13, and/or caspase-14. Z-VAD (also known as Benzyloxycarbonyl-Val-Ala-Asp(OMe)-fluoromethylketone and carbobenzoxy-valyl-alanyl-aspartyl-[O-methyl]-fluoromethylketone) is an exemplary pan-caspase inhibitor and is available from R&D Systems (Cat. No. FMK001) and Promega (Cat. No. G7231). Other exemplary pan-caspase inhibitors that may be used include IDN-6556 (also known as "PF-3,491,390") available from Conatus Pharmaceuticals, Inc. (formerly Idun Pharmaceuticals, Inc.), VX-799 available from Vertex Pharmaceuticals, Inc., MX1013 available Maxim Pharmaceuticals, Inc., Xyz033mp available from LG Chemical, Inc., all of which are described, for example, in Linton, S. D. (2005) CURRENT TOPICS IN MEDICAL CHEM. 5:1697-1717. It is understood that a "pan-caspase inhibitor" may also be a cocktail (e.g., a combination) of caspase inhibitors including two or more of specific caspase inhibitors (e.g., synthetic or endogenous caspase inhibitors).

As used herein, the term "necrosis" is understood to mean caspase-independent cell death characterized by any of the following properties: cellular and/or organelle swelling, plasma membrane rupture, or discontinuity in plasma, nuclear and/or organelle membranes. As used herein, the terms "necroptosis" and "programmed necrosis" refer to a form of necrosis and is understood to mean one form of programmed or regulated necrosis, and in certain embodiments, necroptosis is mediated by the serine/threonine kinase activity of receptor interacting protein (RIP) kinases, for example, RIP-1 kinase and/or RIP-3 kinase.

As used herein, the term "necrosis inhibitor" is understood to mean an agent, which, when administered to a mammal, reduces necrotic cell death in photoreceptor and/or RPE cells. For example, it is understood that certain necrosis inhibitors act by reducing or inhibiting necroptosis or programmed necrosis. A necrosis inhibitor can be an agent that modulates the production and/or activity of one or more RIP kinases (e.g., RIP-1 kinase and/or RIP-3 kinase). For example, an inhibitor of RIP-1 kinase is understood to modulate the activity of RIP-1 kinase as well as downstream RIP kinases, e.g., RIP-3 kinase, in the necrosis cascade. Accordingly, a RIP-1 kinase inhibitor is also understood to modulate RIP-3 kinase activity.

As used herein, the term "necrostatin" or "nec" is understood to mean an inhibitor of caspase-independent cell death or necroptosis. Exemplary necrostatins include necrostatin-1 ("Nec-1"), necrostatin-2 ("Nec-2"), necrostatin-3 ("Nec-3"), necrostatin-4 ("Nec-4"), necrostatin-5 ("Nec-5") and necrostatin-7 ("Nec-7").

In certain embodiments, the necrostatin is a Nec-1 related compound of Formula I:

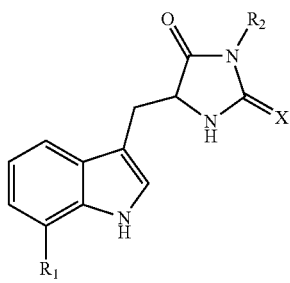

(I)

or a pharmaceutically acceptable salt, ester, or prodrug thereof, wherein

X is O or S;

$R_1$ is hydrogen, $C_1$-$C_6$alkyl, $C_1$-$C_6$alkoxyl, or halogen; and $R_2$ is hydrogen or $C_1$-$C_6$alkyl.

In certain embodiments, X is O. In certain embodiments, $R_1$ is hydrogen or halogen (such as chlorine). In certain embodiments, $R_2$ is a methyl or ethyl. In certain other embodiments, $R_1$ is hydrogen or Cl, and $R_2$ is a methyl.

In certain embodiments, the necrostatin is a Nec-1 related compound of Formula I-A, shown below:

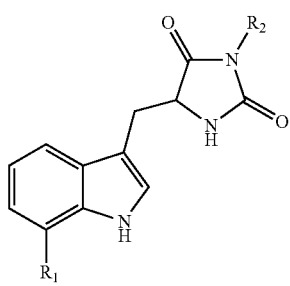

(I-A)

or a pharmaceutically acceptable salt, ester, or prodrug thereof, or optical isomers or racemic mixtures thereof, wherein $R_1$ is H, alkyl, alkoxyl, or a halogen (for example, F, Cl, Br or I) and $R_2$ is H or an alkyl. In certain embodiments, $R_1$ is H or Cl. In certain other embodiments, $R_2$ is a methyl or ethyl. In certain other embodiments, $R_1$ is H or Cl, and $R_2$ is a methyl.

In certain other embodiments, the necrostatin is a Nec-1 related compound of Formula I-B, shown below:

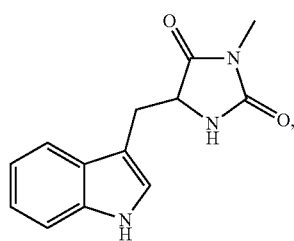

(I-B)

or a pharmaceutically acceptable salt, ester, or prodrug thereof.

In certain other embodiments, the necrostatin is a Nec-1 related compound of Formula I-C, shown below:

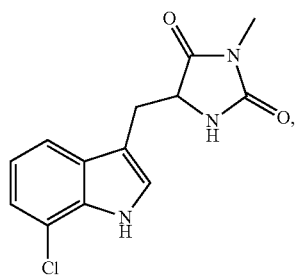

(I-C)

or a pharmaceutically acceptable salt, ester, or prodrug thereof.

In certain other embodiments, the necrostatin is a Nec-1 related compound of Formula I-D, shown below:

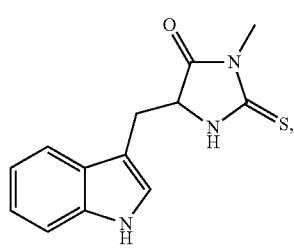

(I-D)

or a pharmaceutically acceptable salt, ester, or prodrug thereof.

In certain other embodiments, the necrostatin is a Nec-1 related compound of Formula I-E, shown below:

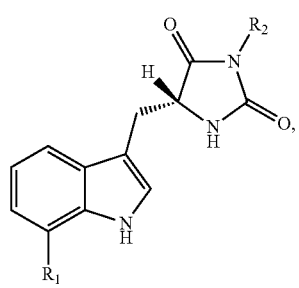

(I-E)

or a pharmaceutically acceptable salt, ester, or prodrug thereof, wherein $R_1$ is H, alkyl, alkoxyl, or a halogen (for example, F, Cl, Br or I) and $R_2$ is H or an alkyl. In certain embodiments, $R_1$ is H or Cl. In certain other embodiments, $R_2$ is a methyl or ethyl. In certain other embodiments, $R_1$ is H or Cl, and $R_2$ is a methyl.

In certain other embodiments, the necrostatin is a Nec-1 related compound of Formula I-F, shown below:

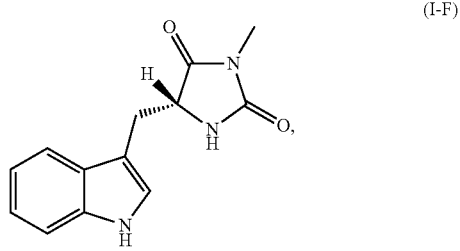 [SMILES: CN1C(=O)N[C@H](Cc2c[nH]c3ccccc23)C1=O]

(I-F)

or a pharmaceutically acceptable salt, ester, or prodrug thereof. In certain other embodiments, the necrostatin is a Nec-1 related compound of Formula I-G, shown below:

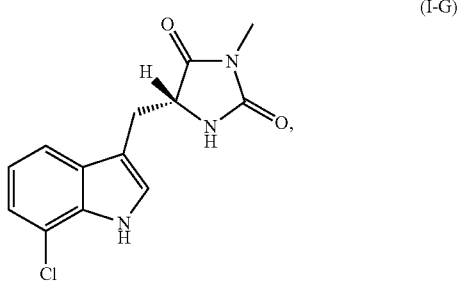 [SMILES: CN1C(=O)N[C@H](Cc2c[nH]c3c(Cl)cccc23)C1=O]

(I-G)

or a pharmaceutically acceptable salt, ester, or prodrug thereof.

The Nec-1 related compounds described above can be prepared based on synthetic procedures described in the literature, such as in Degterev et al. in *Nature Chemical Biology*, (2005), vol. 1, 112-119; Degterev et al. in *Nature Chemical Biology*, (2008), vol. 4, 313-321; and International Patent Application Publication No. WO 2007/075772, all of which are hereby incorporated by reference.

In certain embodiments, the necrostatin is a Nec-2 related compound of Formula II:

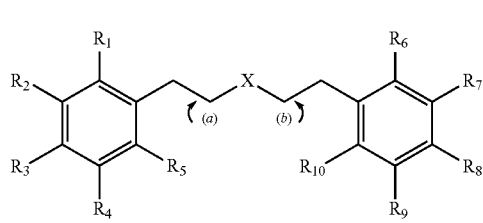

(II)

or a pharmaceutically acceptable salt, ester, or prodrug thereof, wherein:

X is —$CH_2$—, —C(H)($R_{14}$)—, —C(=S)—, —C(=NH)—, or —C(O)—;

$R_1$, $R_2$, $R_3$, $R_4$, $R_5$, $R_6$, $R_7$, $R_8$, $R_9$, and $R_{10}$ each represent independently hydrogen, acyl, acetyl, alkyl, halogen, amino, $C_1$-$C_6$alkoxyl, nitro, —C(O)$R_{12}$, —C(S)$R_{12}$, —C(O)O$R_{12}$, —C(O)N$R_{12}R_{13}$, —C(S)N$R_{12}R_{13}$, or —S($O_2$)$R_{12}$;

$R_{11}$ is hydrogen, acyl, acetyl, alkyl, or acylamino;

$R_{12}$ and $R_{13}$ each represent independently hydrogen, an optionally substituted alkyl, an optionally substituted aryl, an optionally substituted heteroaryl, an optionally substituted aralkyl, or an optionally substituted heteroaralkyl;

$R_{14}$ is acyl, acetyl, alkyl, halogen, amino, acylamino, nitro, —S$R_{11}$, —N($R_{11}$)$_2$, or —O$R_{11}$;

the bond indicated by (a) can be a single or double bond; and the bond indicated by (b) can be a single or double bond.

In certain embodiments, X is —C(O)—. In certain embodiments, $R_1$, $R_2$, $R_5$, $R_6$, $R_7$, and $R_{10}$ each represent independently hydrogen, acyl, alkyl, halogen, or amino. In certain embodiments, $R_3$, $R_4$, $R_8$, and $R_9$ are $C_1$-$C_6$alkoxyl. In certain embodiments, the bond indicated by (a) is a double bond; and the bond indicated by (b) is a double bond. In certain embodiments, when each of $R_1$, $R_4$, $R_5$, $R_6$, $R_9$ and $R_{10}$ is hydrogen and each of $R_2$, $R_3$, $R_7$, and $R_8$ is methoxyl, then X is not —C(O)—, —$CH_2$—, or —CH(OH)—.

In certain other embodiments, the necrostatin is a Nec-2 related compound of Formula II-A:

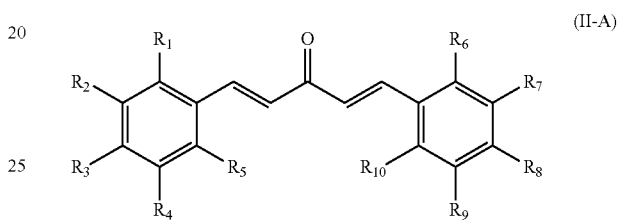

(II-A)

or a pharmaceutically acceptable salt thereof, wherein:

$R_1$, $R_2$, $R_5$, $R_6$, $R_7$, and $R_{10}$ each represent independently hydrogen, alkyl, halogen, amino, or methoxyl; and $R_3$, $R_4$, $R_8$, and $R_9$ are $C_1$-$C_6$alkoxyl.

In certain other embodiments, the Nec-2 related compound is

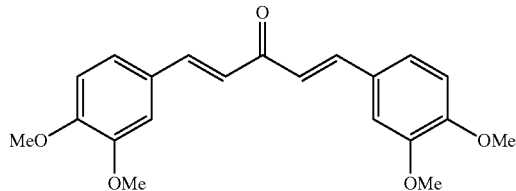 [SMILES: COc1ccc(/C=C/C(=O)/C=C/c2ccc(OC)c(OC)c2)cc1OC]

or a pharmaceutically acceptable salt thereof.

The Nec-2 related compounds described above can be prepared based on synthetic procedures described in the literature, such as in International Patent Application Publication No. WO 2007/075772, which is hereby incorporated by reference.

In certain embodiments, the necrostatin is a Nec-3 related compound of Formula III:

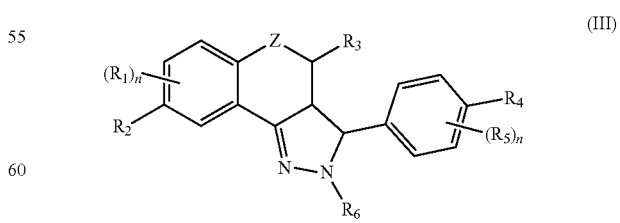

(III)

or a pharmaceutically acceptable salt, ester, or prodrug thereof, wherein:

Z is —$CH_2$—, —$CH_2CH_2$—, —O—, —S—, —S(O)—, —S($O_2$)—, or —N($R_7$)—;

$R_1$, $R_3$, and $R_5$ each represent independently for each occurrence hydrogen, halogen, hydroxyl, amino, $C_1$-$C_6$alkyl, $C_1$-$C_6$alkoxy, $C_1$-$C_6$alkoxy-$C_1$-$C_6$alkyl, $C_1$-$C_6$alkanoyl, $C_1$-$C_6$alkylsulfinyl, $C_1$-$C_6$alkylsulfonyl, $C_1$-$C_6$alkylsulfonyl-$C_1$-$C_6$alkyl, aryl, aralkyl, heterocycloalkyl, heteroaryl, or heteroaralkyl;

$R_2$ and $R_4$ are $C_1$-$C_6$alkoxy;

$R_6$ is —C(O)$R_8$, —C(S)$R_8$, —C(O)O$R_8$, —C(O)N$R_8R_9$, —C(S)N$R_8R_9$, —C(NH)$R_8$, or —S(O$_2$)$R_8$;

$R_7$ is alkyl, aralkyl, or heteroaralkyl;

$R_8$ and $R_9$ each represent independently hydrogen, $C_1$-$C_6$alkyl, heteroalkyl, aryl, heteroaryl, aralkyl, or heteroaralkyl; and n represents independently for each occurrence 0, 1, or 2.

In certain embodiments, Z is —CH$_2$—. In certain embodiments, $R_1$, $R_3$, and $R_5$ each represent independently for each occurrence hydrogen, halogen, hydroxyl, amino, or $C_1$-$C_6$alkyl. In certain embodiments, $R_2$ and $R_4$ are methoxy. In certain embodiments, $R_6$ is C(O)$R_8$, and $R_8$ is $C_1$-$C_6$alkyl. In certain embodiments, $R_7$ is alkyl. In certain embodiments, $R_8$ and $R_9$ each represent independently hydrogen or $C_1$-$C_6$alkyl. In certain embodiments, n is 0.

In certain embodiments, the Nec-3 related compound is

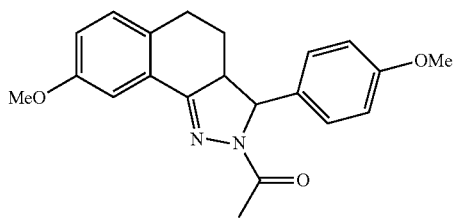 [SMILES: COc1ccc(C2C3CCc4ccc(OC)cc4C3=NN2C(C)=O)cc1]

or a pharmaceutically acceptable salt thereof.

In certain other embodiments, the Nec-3 related compound is

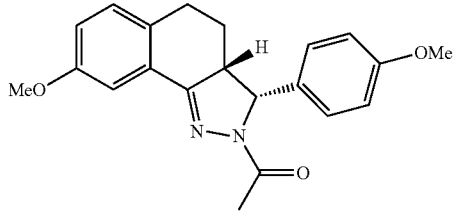 [SMILES: COc1ccc([C@H]2[C@H]3CCc4ccc(OC)cc4C3=NN2C(C)=O)cc1]

or a pharmaceutically acceptable salt thereof.

The Nec-3 related compounds described above can be prepared based on synthetic procedures described in the literature, such as in Degterev et al. in *Nature Chemical Biology*, (2008), vol. 4, 313-321; and International Patent Application Publication No. WO 2007/075772, both of which is hereby incorporated by reference.

In certain embodiments, the necrostatin is a Nec-4 related compound of Formula IV:

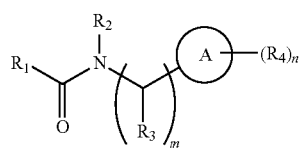

(IV)

or a pharmaceutically acceptable salt, ester, or prodrug thereof, wherein:

$R_1$ is

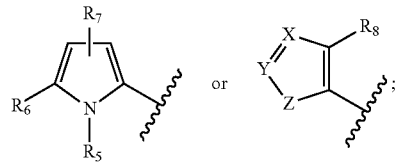

$R_2$ and $R_3$ each represent independently for each occurrence hydrogen or methyl;

$R_4$ represents independently for each occurrence halogen, hydrogen, $C_1$-$C_6$alkyl, $C_2$-$C_6$alkenyl, or $C_2$-$C_4$alkynyl;

$R_5$ is $C_1$-$C_4$alkyl;

$R_6$ is hydrogen, halogen, or —CN;

$R_7$ is hydrogen or $C_1$-$C_4$alkyl;

$R_8$ is $C_1$-$C_6$alkyl, or $R_8$ taken together with $R_9$, when present, forms a carbocyclic ring;

$R_9$ is hydrogen or $C_1$-$C_6$alkyl, or $R_9$ taken together with $R_8$ forms a carbocyclic ring;

$R_{10}$ is hydrogen or $C_1$-$C_6$alkyl;

A is phenylene or a 5-6 membered heteroarylene;

X is N or —C($R_9$)—;

Y is N or —C($R_{10}$)—;

Z is S or O; and m and n each represent independently 1, 2, or 3.

In certain embodiments, $R_1$ is

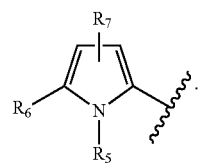

In certain other embodiments, $R_1$ is

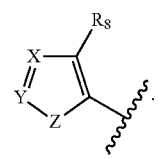

In certain embodiments, $R_2$ is hydrogen. In certain embodiments, $R_3$ is methyl. In certain other embodiments, $R_3$ is hydrogen. In certain embodiments, $R_4$ is halogen, such as fluorine or chlorine. In certain embodiments, $R_4$ is halogen. In certain embodiments, $R_5$ is methyl or ethyl. In certain embodiments, $R_6$ is —CN. In certain embodiments, A is phenylene. In certain embodiments, X is N. In certain embodiments, Y is N. In certain embodiments, Z is S. In certain embodiments, A is phenylene. In certain embodiments, $R_1$ is $C_1$-$C_6$alkyl, such as methyl. In certain embodiments, m is 1. In certain embodiments, n is 2.

In certain embodiments, the necrostatin is a Nec-4 related compound of Formula IV-A:

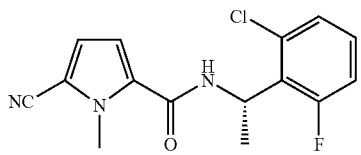 [SMILES: C[C@H](NC(=O)c1ccc(C#N)n1C)c1c(F)cccc1Cl]

or a pharmaceutically acceptable salt thereof.

In certain embodiments, the necrostatin is a Nec-4 related compound of Formula IV-B:

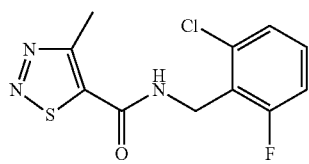 [SMILES: Cc1nnsc1C(=O)NCc1c(F)cccc1Cl]

or a pharmaceutically acceptable salt thereof.

The Nec-4 related compounds described above can be prepared based on synthetic procedures described in the literature, such as in Teng et al. (2007) BIOORG MED CHEM LETT, 17: 6836-6840; and Teng et al. (2008) BIOORG MED CHEM LETT, 18: 3219-3223, both of which are incorporated herein by reference.

In certain embodiments, the necrostatin is a Nec-5 related compound of Formula V:

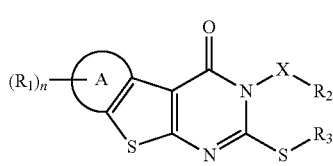

or a pharmaceutically acceptable salt, ester, or prodrug thereof, wherein:

A is a saturated or unsaturated 5-6 membered carbocyclic ring;

X is a bond or $C_1$-$C_4$alkylene;

$R_1$ is $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

$R_2$ is

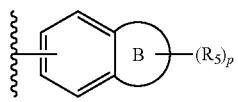

or

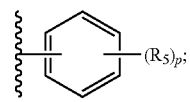

$R_3$ is —$C_1$-$C_6$alkylene-CN, —CN, $C_1$-$C_6$alkyl, or $C_2$-$C_6$alkenyl;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

B is a 5-6 membered heterocyclic or carbocylic ring; and n and p each represent independently 0, 1, or 2.

In certain embodiments, X is a bond. In certain embodiments, A is an unsaturated 6-membered carbocyclic ring. In certain embodiments, $R_1$ is $C_1$-$C_6$alkyl, halogen, hydroxyl, or $C_1$-$C_6$alkoxyl. In certain embodiments, $R_2$ is

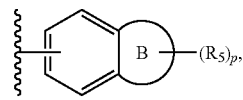

such as

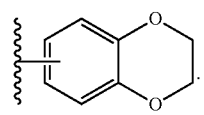

In certain embodiments, $R_3$ is —$C_1$-$C_6$alkylene-CN, such as —$CH_2$—CN. In certain embodiments, $R_4$ represents independently for each occurrence hydrogen or $C_1$-$C_6$alkyl. In certain embodiments, $R_5$ represents independently for each occurrence $C_1$-$C_6$alkyl, halogen, hydroxyl, or $C_1$-$C_6$alkoxyl. In certain embodiments, B is a 5-6 membered heterocyclic ring. In certain embodiments, n is 0. In certain embodiments, p is 0.

In certain embodiments, the necrostatin is a Nec-5 related compound of Formula V-A:

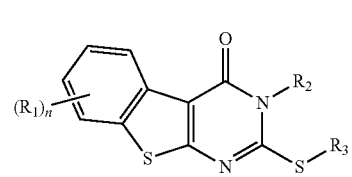

or a pharmaceutically acceptable salt, ester, or prodrug thereof, wherein:

$R_1$ is $C_1$-$C_6$alkyl, halogen, hydroxyl, $C_1$-$C_6$alkoxyl, or —$N(R_4)_2$;

$R_2$ is

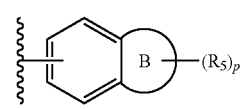

or

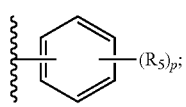

$R_3$ is —$C_1$-$C_6$alkylene-CN;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

B is a 5-6 membered heterocyclic or carbocylic ring; and n and p each represent independently 0, 1, or 2.

In certain embodiments, the Nec-5 compound is

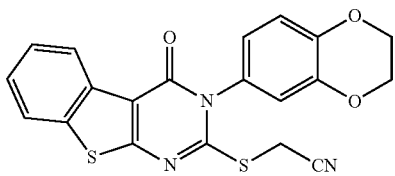 [SMILES: N#CCSc1nc2sc3ccccc3c2c(=O)n1-c1ccc2c(c1)OCCO2]

or a pharmaceutically acceptable salt thereof.

The Nec-5 related compounds described above can be prepared based on synthetic procedures described in the literature, such as in Degterev et al. in Nature Chemical Biology, (2008), vol. 4, 313-321; and International Patent Application Publication No. WO 2008/045406, both of which is hereby incorporated by reference.

In certain embodiments, the necrostatin is a Nec-7 related compound of Formula VII:

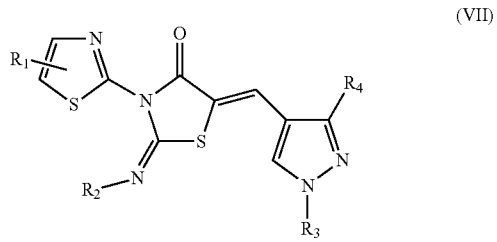

(VII)

or a pharmaceutically acceptable salt, ester, or prodrug thereof, wherein:

$R_1$, $R_2$, and $R_3$ each represent independently hydrogen or $C_1$-$C_4$alkyl;

$R_4$ is

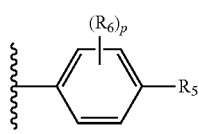

or

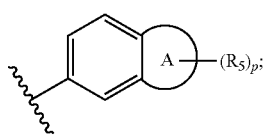

$R_5$ and $R_6$ each represent independently for each occurrence halogen, $C_1$-$C_6$alkyl, hydroxyl, $C_1$-$C_6$alkoxyl, —N($R_7$)$_2$, —NO$_2$, —S—$C_1$-$C_6$alkyl, —S-aryl, —SO$_2$-aryl, —C(O)$R_7$, —CO$_2$$R_7$, —C(O)N($R_7$)$_2$, heterocycloalkyl, aryl, or heteroaryl;

$R_7$ represents independently for each occurrence hydrogen, $C_1$-$C_6$alkyl, aryl, or aralkyl; or two occurrences of $R_7$ attached to the same nitrogen atom are taken together with the nitrogen atom to which they are attached to form a 3-7 membered heterocyclic ring;

A is a 5-6 membered heterocyclic ring; and p is 0, 1, or 2.

In certain embodiments, $R_1$ is hydrogen. In certain embodiments, $R_2$ is hydrogen. In certain embodiments, $R_3$ is hydrogen. In certain embodiments, $R_4$ is

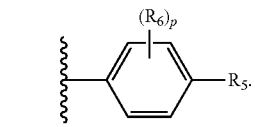

In certain embodiments, $R_5$ is halogen, $C_1$-$C_6$alkyl, hydroxyl, $C_1$-$C_6$alkoxyl, or —N($R_7$)$_2$. In certain other embodiments, $R_5$ is halogen, such as fluorine or chlorine. In certain embodiments, p is 0. In certain other embodiments, $R_4$ is

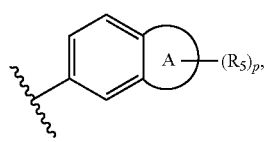

such as

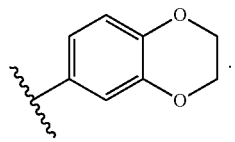 [SMILES: *c1ccc2c(c1)OCCO2]

In certain embodiments, the Nec-7 related compound is

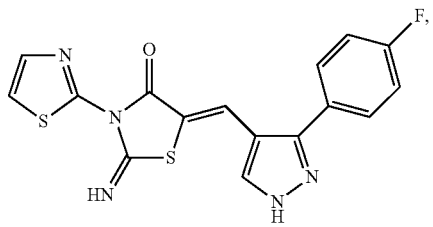 [SMILES: N=C1S/C(=C\c2c[nH]nc2-c2ccc(F)cc2)C(=O)N1c1nccs1]

or a pharmaceutically acceptable salt thereof.

The Nec-7 related compounds described above can be prepared based on synthetic procedures described in the literature, such as in Zheng et al. in BIOORG MED CHEM LETT, 2008, vol. 18, 4932-4935, which is incorporated herein by reference.

In certain embodiments, the necrostatin is a Nec-7 related compound of Formula VIII:

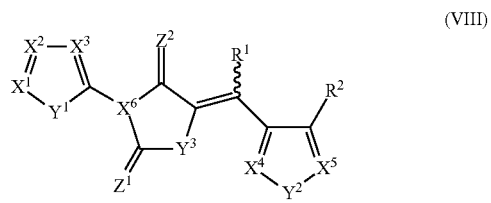

(VIII)

or a pharmaceutically acceptable salt, ester, or prodrug thereof, wherein:

each $X^1$, $X^2$, $X^3$, $X^4$, $X^5$, and $X^6$ is selected, independently, from N or $CR^{X1}$;

each $Y^1$, $Y^2$, and $Y^3$ is selected, independently, from O, S, $NR^{Y1}$, or $CR^{Y2}R^{Y3}$;

each $Z^1$ and $Z^2$ is selected, independently, from O, S, or $NR^{Z1}$;

each $R^{Y1}$ and $R^{Z1}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, optionally substituted heteroaryl, —C(=O)$R^{5A}$, —C(=O)O$R^{5A}$, or —C(=O)N$R^{5A}R^{6A}$;

each $R^{X1}$, $R^{Y2}$, and $R^{Y3}$ is selected, independently, from H, halogen, CN, NC, NO$_2$, N$_3$, O$R^3$, S$R^3$, N$R^3R^4$, —C(=O)$R^{5A}$, —C(=O)O$R^{5A}$, —C(=O)N$R^{5A}R^{6A}$, —S(=O)$R^{5A}$, —S(=O)$_2R^{5A}$, —S(=O)$_2$O$R^{5A}$, —S(=O)$_2$N$R^{5A}R^{6A}$, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl;

each $R^1$, $R^2$ $R^{5A}$, $R^{5B}$, $R^{6A}$, and $R^{6B}$ is selected from H, optionally substituted $C_{1-6}$ alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl; or $R^{5A}$ and $R^{6A}$, or $R^{5B}$ and $R^{6B}$ combine to form a heterocyclyl; and each $R^3$ and $R^4$ is selected from H, optionally substituted $C_{1-6}$ alkyl, optionally substituted cycloalkyl, optionally substituted heterocyclyl, optionally substituted aryl, optionally substituted heteroaryl, —C(=O)$R^{5B}$, —C(=S)$R^{5B}$, —C(N$R^{6B}$)$R^{5B}$, —C(=O)O$R^{5B}$, —C(=O)N$R^{5B}R^{6B}$, —S(=O)$R^{5B}$, —S(=O)$_2R^{5B}$, —S(=O)$_2$O$R^{5B}$, or —S(=O)$_2$N$R^{5B}R^{6B}$. In certain embodiments, when $R^1$ is H, $X^1$, $X^2$, and $X^4$ are each CH, $X^3$, $X^5$, and $X^6$ are each N, $Y^1$ and $Y^3$ are each S, $Y^2$ is NH, $Z^1$ is NH, and $Z^2$ is O, then $R^2$ is not 4-fluorophenyl.

In certain embodiments, the necrostatin is a Nec-7 related compound of Formula VIII-A:

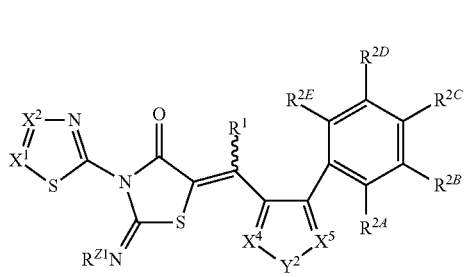

(VIII-A)

or a pharmaceutically acceptable salt, ester, or prodrug thereof, wherein:

$X^1$, $X^2$, $X^4$, $X^5$, $R^1$, $Y^2$, and $R^{Z1}$ are as defined for Formula (VIII);

each $R^{2A}$, $R^{2B}$, $R^{2C}$, $R^{2D}$, and $R^{2E}$ is selected, independently, from H, halogen, optionally substituted $C_{1-6}$ alkyl, optionally substituted $C_{2-6}$ alkenyl, optionally substituted $C_{2-6}$ alkynyl, optionally substituted cycloalkyl, optionally substituted heterocyclyl, optionally substituted aryl, optionally substituted heteroaryl, CN, NC, NO$_2$, N$_3$, O$R^7$, S$R^7$, S(=O)$R^{12}$, S(=O)$_2R^{12}$, S(=O)O$R^{12}$, S(=O)$_2$O$R^{12}$, N$R^7R^8$, C(=O)$R^{12}$, C(=O)O$R^{12}$, C(=O)N$R^{12}R^{13}$, C(=S) $R^{12}$, C(=S)O$R^{12}$, C(=S)N$R^{12}R^{13}$, C(=N$R^9$)$R^{12}$, C(=N$R^9$)O$R^{12}$, or C(=NR9)N$R^{12}R^{13}$, R or $R^{2A}$ and $R^{2B}$, $R^{2B}$ and $R^{2C}$, $R^{2C}$ and $R^{2D}$, or $R^{2D}$ and $R^{2E}$ combine to form an optionally substituted cycloalkyl or an optionally substituted heterocyclyl;

each $R^7$, $R^8$, and $R^9$ is selected, independently, from H, optionally substituted $C_{1-6}$ alkyl, optionally substituted cycloalkyl, optionally substituted heterocyclyl, optionally substituted aryl, optionally substituted heieroaryl, S(=O)$R^{10}$, S(=O)$_2R^{10}$, C(=O)$R_{10}$, C(O)O$R^{10}$, C(=O)N$R^{10}R^{11}$, C(=S)$R^{10}$, C(=S)O$R^{10}$, C(=S)N$R^{10}R^{11}$, C(N$R^{14}$)$R^{R10}$, C(N$R^{14}$)O$R^{10}$, or C(=N$R^{14}$)N$R^{10}R^{11}$, or $R^7$ and $R^8$ combine to form an optionally substituted heterocyclyl; and each $R^{10}$, $R^{11}$, $R^{12}$, $R^{13}$, and $R^{14}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl, or $R^{10}$ and $R^{11}$ or $R^{12}$ and $R^{13}$ combine to form an optionally substituted heterocyclyl.

In certain embodiments, each $R^{2A}$, $R^{2B}$, $R^{2C}$, $R^{2D}$, and $R^{2E}$ is selected, independently, from H, halogen, $C_{1-6}$ alkyl, $C_{2-6}$ alkenyl, $C_{2-6}$ alkynyl, cycloalkyl, heterocyclyl, aryl, or heteroaryl.

In certain embodiments, the necrostatin is a Nec-7 related compound selected from:

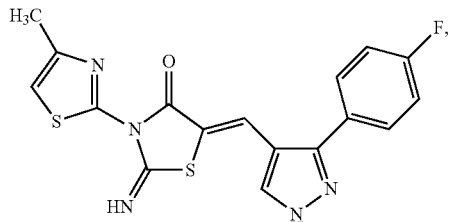

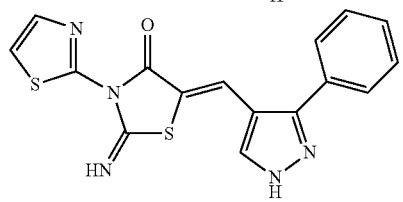

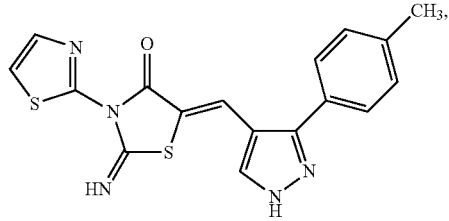

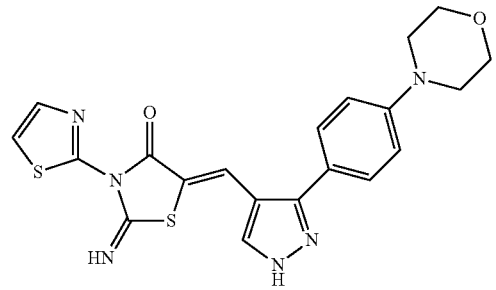

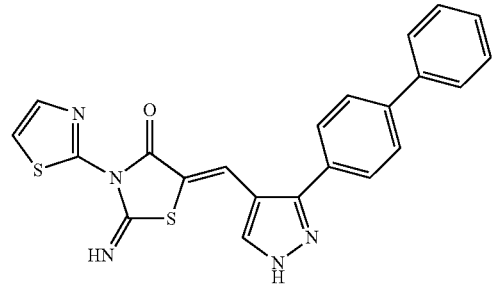

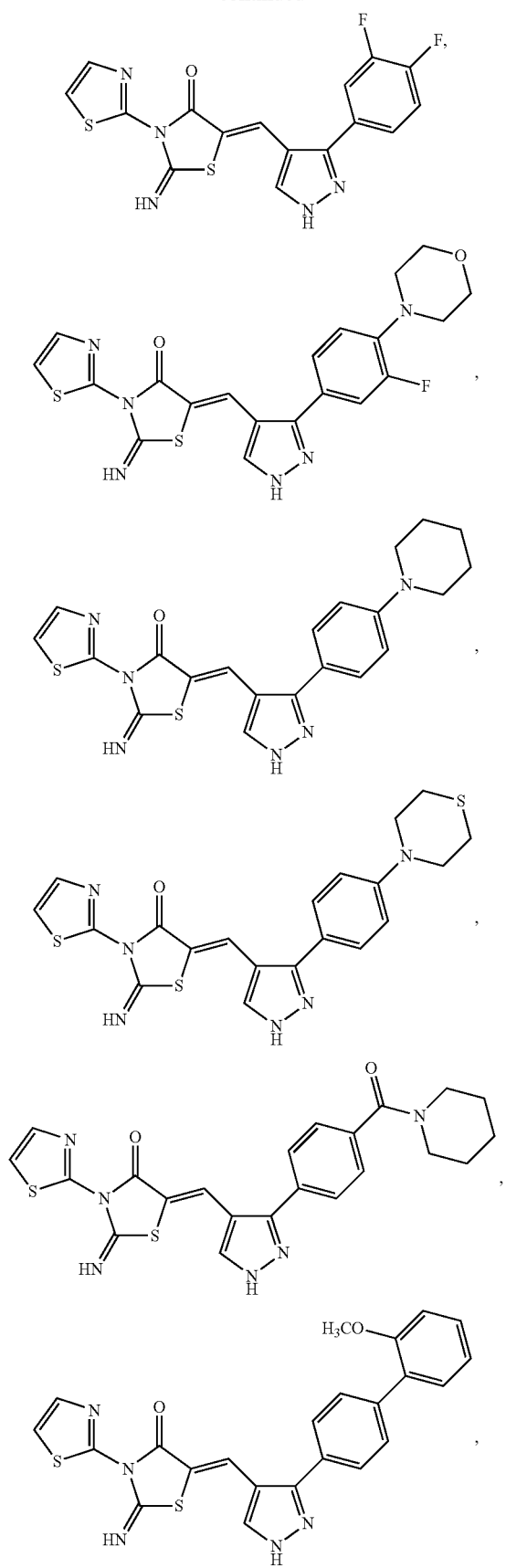

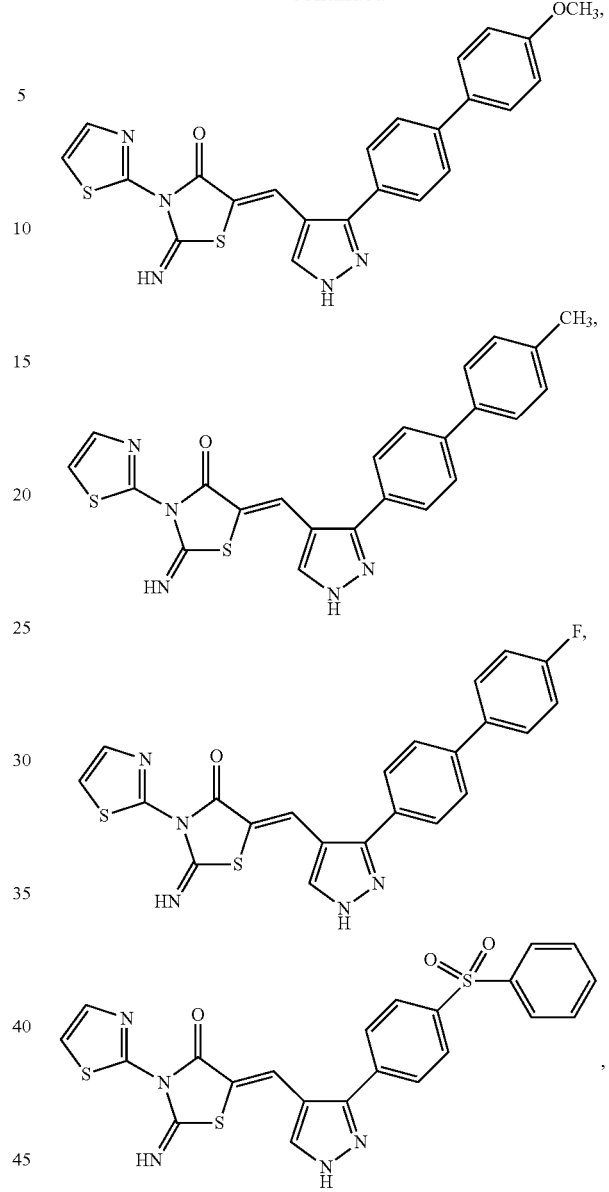

and pharmaceutically acceptable salts thereof.

The Nec-7 related compounds described above can be prepared based on synthetic procedures described in the literature, such as International Patent Application Publication No. WO 2010/075290, which is hereby incorporated by reference.

In certain embodiments, the necrostatin is a Nec-4 related compound of Formula IX:

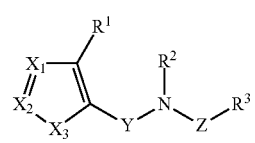

(IX)

or a pharmaceutically acceptable salt, ester, or prodrug thereof, wherein:

$X_1$ and $X_2$ are, independently, N or $CR^4$;

X₃ is selected from O, S, NR⁵, or —(CR⁵)₂;

Y is selected from C(O) or CH₂; and

Z is (CR⁶R⁷)ₙ;

R¹ is selected from H, halogen, optionally substituted C₁₋₆alkyl, or optionally substituted C₁₋₆cycloalkyl, or optionally substituted aryl;

R² is selected from H or optionally substituted C₁₋₆alkyl;

R³ is optionally substituted aryl;

each R⁴ is selected from H, halogen, carboxamido, nitro, cyano, optionally substituted C₁₋₆alkyl, or optionally substituted aryl;

R⁵ is selected from H, halogen, optionally substituted C₁₋₆alkyl, or optionally substituted aryl;

each R⁶ and R⁷ is, independently, selected from H, optionally substituted C₁₋₆alkyl, or aryl; and n is 0, 1, 2, or 3. In certain embodiments, when X₁ and X₂ are N, X₃ is S, Y is C(O), Z is CH₂, R² is H, and R³ is 2-chloro-6-fluoro-phenyl, then R¹ is not methyl.

In certain embodiments, the necrostatin is a Nec-4 related compound of Formula IX-A:

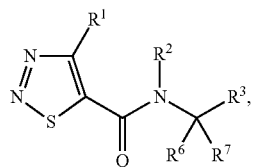

(IX-A)

or a pharmaceutically acceptable salt, ester, or prodrug thereof, wherein:

R¹, R², R³, R⁶ and R⁷ are as defined in Formula (IX).

In certain embodiments, the necrostatin is a Nec-4 related compound selected from:

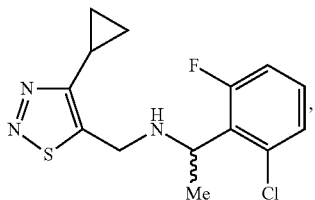

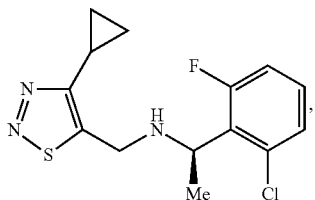

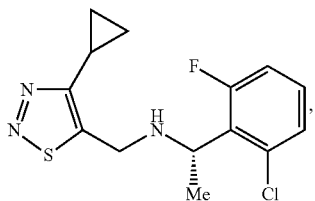

-continued

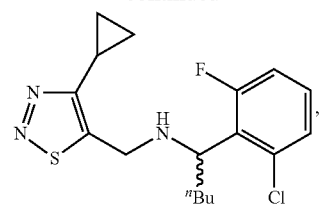

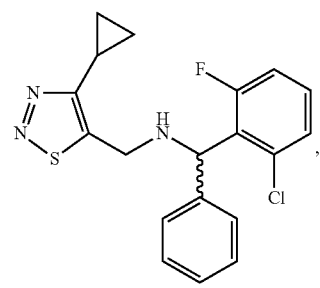

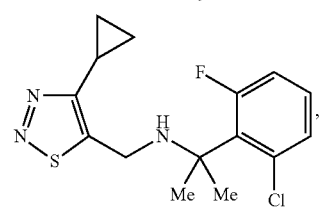

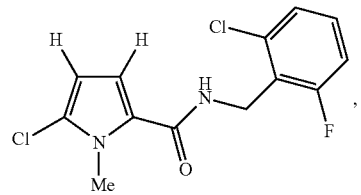

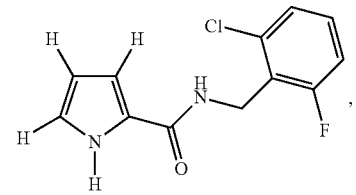

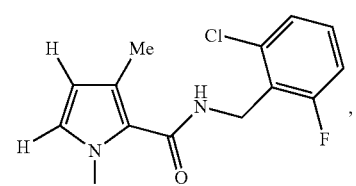

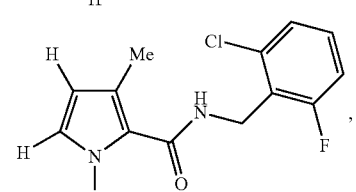

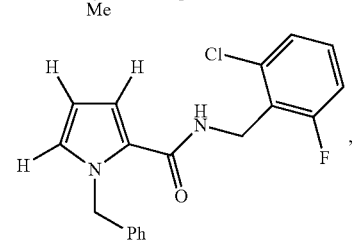

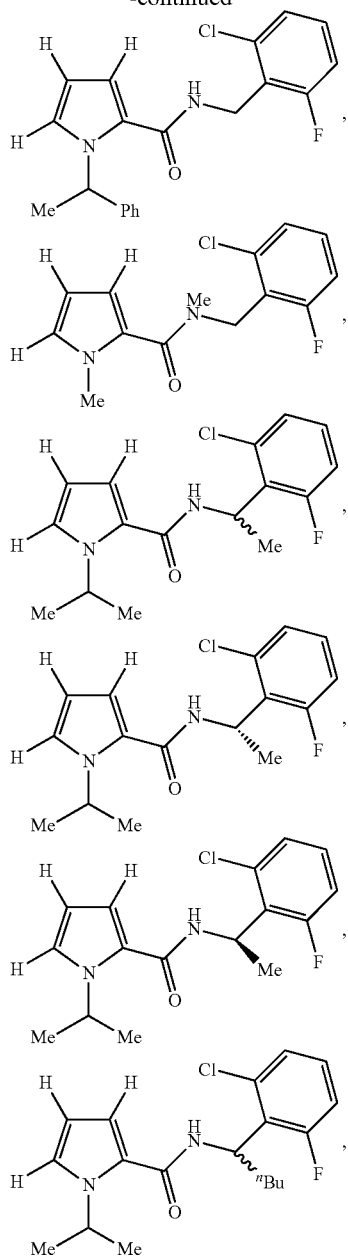

and pharmaceutically acceptable salts thereof.

The Nec-4 related compounds described above can be prepared based on synthetic procedures described in the literature, such as U.S. Patent Application Publication No. 2009/0099242, which is hereby incorporated by reference.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 10 or fewer carbon atoms in its backbone (e.g., $C_1$-$C_{10}$ for straight chain, $C_3$-$C_{10}$ for branched chain), and alternatively, 5, 4, 3, 2 or 1 carbon atoms in its backbone. Likewise, cycloalkyls have from about 3 to about 10 carbon atoms in their ring structure, and alternatively about 5, 6 or 7 carbons in the ring structure.

Exemplary alkyl groups include methyl, ethyl, n-propyl, isopropyl, n-butyl, sec-butyl, isobutyl, tert-butyl, cyclopropyl, and cyclobutyl.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, or —O-alkynyl. The term "alkylene" refers to a diradical of an alkyl group. An exemplary alkylene group is —CH$_2$CH$_2$—.

The term "aralkyl" refers to an alkyl group substituted with an aryl group.

The term "heteroaralkyl" refers to an alkyl group substituted with a heteroaryl group.

The term "alkenyl" refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as $C_2$-$C_{12}$alkynyl, $C_2$-$C_8$alkynyl, and $C_2$-$C_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, heteroaryl, —CF$_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls.

In certain embodiments, the aromatic group is not substituted, i.e., it is unsubstituted.

The term "phenylene" refers to a multivalent radical (e.g., a divalent or trivalent radical) of benzene. To illustrate, a divalent valent radical of benzene is illustrated by the formula

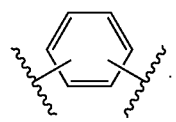

The terms "heterocyclyl" or "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocycyl group is not substituted, i.e., it is unsubstituted.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls.

The term "heteroarylene" refers to a multi-valent (e.g., di-valent or trivalent) aromatic group that comprises at least one ring heteroatom. An exemplary "heteroarylene" is pyridinylene, which is a multi-valent radical of pyridine. For example, a divalent radical of pyridine is illustrated by the formula

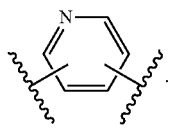

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "amine" and "amino" are art-recognized and refer to both unsubstituted and substituted amines, e.g., a moiety that may be represented by the general formula:

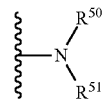

wherein $R^{50}$ and $R^{51}$ each independently represent hydrogen, alkyl, alkenyl, or —(CH$_2$)$_m$—R$^{61}$; or $R^{50}$ and $R^{51}$, taken together with the N atom to which they are attached complete a heterocycle having from 4 to 8 atoms in the ring structure; wherein $R^{61}$ is aryl, cycloalkyl, cycloalkenyl, a heterocycle or a polycycle; and m is zero or an integer in the range of 1 to 8. In certain embodiments, $R^{50}$ and $R^{51}$ each independently represent hydrogen or alkyl.

The term "amide" or "amido" as used herein refers to a radical of the form —R$_a$C(O)N(R$_b$)—, —R$_a$C(O)N(R$_b$)R$_c$—, —C(O)NR$_b$R$_c$, or —C(O)NH$_2$, wherein R$_a$, R$_b$ and R$_c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, R$_b$, R$_c$, or R$_a$. The amide also may be cyclic, for example R$_b$ and R$_c$, R$_a$ and R$_b$, or R$_a$ and R$_c$ may be joined to form a 3- to 12-membered ring, such as a 3- to 10-membered ring or a 5- to 6-membered ring. The term "carboxamido" refers to the structure —C(O)NR$_b$R$_c$.

The term "sulfonamide" or "sulfonamido" as used herein refers to a radical having the structure —N(R$_r$)—S(O)$_2$—R$_S$— or —S(O)$_2$—N(R$_r$)R$_S$, where R$_r$, and R$_S$ can be, for example, hydrogen, alkyl, aryl, cycloalkyl, and heterocyclyl. Exemplary sulfonamides include alkylsulfonamides (e.g., where R$_S$ is alkyl), arylsulfonamides (e.g., where R$_S$ is aryl), cycloalkyl sulfonamides (e.g., where R$_S$ is cycloalkyl), and heterocyclyl sulfonamides (e.g., where R$_S$ is heterocyclyl), etc.

The term "sulfonyl" as used herein refers to a radical having the structure R$_u$SO$_2$—, where R$_u$ can be alkyl, aryl, cycloalkyl, and heterocyclyl, e.g., alkylsulfonyl. The term "alkylsulfonyl" as used herein refers to an alkyl group attached to a sulfonyl group.

The symbol "⌇" indicates a point of attachment.

Unless specified otherwise, the term "optionally substituted" as used herein means that the specified group may be substituted at one, two or more positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, heteroaryl, —CF$_3$, —CN, or the like.

As used herein, the term "therapeutically effective amount" is understood to mean the amount of an active ingredient, for example, a necrostatin (e.g., necrostatin-1 or necrostatin-4) and/or a pan-caspase inhibitor (e.g., Z-VAD or IDN-6556) that is sufficient to reduce, minimize or eliminate the death of photoreceptor and/or RPE cells associated with certain ocular disorders described herein. The compounds of the invention are administered in amounts effective at, e.g., reducing the death of photoreceptor and/or RPE cells, increasing efficacy compared to monotherapy with either drug alone, preserving or improving vision, preserving or improving visual function, and/or preventing vision loss. It is understood that preserving vision or visual function, includes stabilizing vision or visual function and/or slowing the decline of vision or visual function prior to treatment.

As used herein, "pharmaceutically acceptable" or "pharmacologically acceptable" mean molecular entities and compositions that do not produce an adverse, allergic or other untoward reaction when administered to an animal, or to a human, as appropriate. The term, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Disclosed herein is a method of preserving the visual function of an eye of a subject with an ocular condition, wherein a symptom of the ocular condition is the loss of photoreceptor cell viability in the retina of the eye with the condition. The method comprises (a) administering to the eye of the subject an effective amount of a necrostatin and an effective amount of an apoptosis inhibitor thereby preserving the viability of the photoreceptor cells disposed within the retina of the eye, and (b) measuring the visual function (e.g., visual acuity) of the eye after the administration of the necrosis inhibitor and the apoptosis inhibitor. After administration of the necrosis inhibitor and the apoptosis inhibitor the visual function of the eye may be preserved or improved relative to the visual function of the eye prior to administration of the necrosis inhibitor and the apoptosis inhibitor.

Also disclosed is a method of preserving the visual function of an eye of a subject with an ocular condition wherein a symptom of the eye is the loss of photoreceptor cell and/or RPE cell viability in the retina of the eye. The method comprises reducing the production and/or activity of a RIP-1 kinase and/or a RIP-3 kinase in the eye to preserve the viability of the photoreceptor cells and/or RPE cells disposed within the eye. The reduction in the production and/or activity of the RIP-1 kinase and/or RIP-3 kinase may be achieved by administering an effective amount of a necrosis inhibitor (e.g., RIPK inhibitor, e.g., a necrostatin). The reduction in the production and/or activity of the RIP-1 kinase and/or RIP-3 kinase may be direct (e.g., the necrosis inhibitor modulates the production and/or activity the RIP-1 kinase and/or RIP-3 kinase directly) or indirect (e.g., the necrosis inhibitor acts upstream of the RIP-1 kinase and/or RIP-3 kinase but the administration of which indirectly modulates the production and/or activity of the RIP-1 kinase and/or RIP-3 kinase). Visual function of the eye may be measured before and/or after the administration of the necrosis inhibitor that directly or indirectly reduces the production and/or activity of a RIP-1 kinase and/or RIP-3 kinase. After administration of the necrosis inhibitor the visual function of the eye may be preserved or improved relative to the visual function of the eye prior to administration of the necrosis inhibitor.

In each of the foregoing methods, the ocular condition, wherein a symptom of the condition is the loss of photoreceptor cell viability in the retina of the eye, includes but is not limited to AMD (e.g., dry AMD or neovascular AMD), RP and allied diseases (i.e., diseases in the same spectrum, for example, Usher's Syndrome, Cone-Rod dystrophy, and Bardet-Biedl Syndrome), retinal detachment, macular edema (e.g, macular edema caused by vein occlusion, diabetes and intraocular inflammation), diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, and light induced toxicity.

Also disclosed is a method of preserving the viability of photoreceptor cells disposed within a retina of a mammalian eye affected by AMD, RP, macular edema, central areolar choroidal dystrophy, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. The method comprises administering a necrosis inhibitor and/or an apoptosis inhibitor to the eye in which a region of the retina has been affected in amounts sufficient to preserve the viability of photoreceptor cells disposed within the region of the affected retina.

Also disclosed is a method of preserving the viability of RPE cells of a subject with an ocular condition, wherein a symptom of the ocular condition is the loss of RPE cell in the retina of an eye with the condition. The method comprises administering a necrosis inhibitor and/or an apoptosis inhibitor to the eye in which a region of the retina has been affected in amounts sufficient to preserve the viability of the RPE cells.

In each of the foregoing methods, the ocular condition, wherein a symptom of the condition is the loss of RPE cell viability in the retina of the eye, includes but is not limited to AMD (e.g., dry AMD or neovascular AMD), BEST disease, Stargardt's disease, uveitis, adult foveomacular dystrophy, fundus flavimaclatus, myopic degeneration, multiple evanescent white dot syndrome, serpiginous choroidopathy, AMPPE, and other uveitis disorders.

Also disclosed is a method of preserving the viability of photoreceptor cells disposed within a retina of a mammalian eye following retinal detachment. The method comprises administering a necrostatin and an apoptosis inhibitor to the eye in which a region of the retina has been detached in amounts sufficient to preserve the viability of photoreceptor cells disposed within the region of the detached retina. In certain embodiments, when the only necrostatin administered is necrostatin-1, the region is exposed to a final concentration of necrostatin in the eye of greater than about 100 µM. The retinal detachment can be rhegmatogenous retinal detachment, tractional retinal detachment, or serous retinal detachment.

As discussed above, the prevention of photoreceptor death following retinal detachment by co-administration of an apoptotic inhibitor and a necrostatin, e.g., necrostatin-1, at concentrations that exceed 100 µM was surprising because it had been believed that concentrations of necrostatin-1 exceeding 100 µM were toxic and, therefore, could not be administered at such a dosage. It was an unexpected finding that the combination of a necrostatin, e.g., necrostatin-1, and a pan-caspase inhibitor, e.g., Z-VAD, achieved a synergistic effect in reducing photoreceptor cell death following retinal detachment compared to either drug alone.

Unless specified, the necrostatin can be administered to give a final concentration of greater than about 30 µM, for example, in the range of about 30 µM to about 1000 µM. In certain embodiments, the necrostatin can be administered in an amount sufficient to give a final concentration of necrostatin in the eye of greater than about 30 μM. For example, the necrostatin may be administered in an amount sufficient to give a final concentration of necrostatin in the eye in the range from about 30 μM to about 1000 μM, 50 μM to about 1000 μM, 80 μM to about 1000 μM, about 100 μM to about 1000 μM, about 150 μM to about 1000 μM, from about 200 μM to about 800 μM, or from about 200 μM to about 600 μM. In certain embodiments, the necrostatin is administered in an amount sufficient to give a final concentration of necrostatin in the eye of about 400 μM.

The apoptosis inhibitor, for example, the pan-caspase inhibitor, can be administered in an amount sufficient to give a final concentration of the inhibitor in the eye of greater than about 40 μM, for example, in the range of about 40 μM to about 500 μM. For example, the apoptosis inhibitor can be administered in an amount sufficient to give a final concentration of the inhibitor in the eye of greater than about 60 μM, 80 μM, or 100 μM. For example, the apoptosis inhibitor can be administered in an amount sufficient to give a final concentration of the inhibitor in the eye in the range from about 80 μM to about 500 μM, 100 μM to about 500 μM, 125 μM to about 500 μM, 150 μM to about 500 μM or from about 200 μM to about 400 μM. In certain embodiments, apoptosis inhibitor (e.g., the pan-caspase inhibitor) is administered in an amount sufficient to give a final concentration of the inhibitor in the eye of about 300 μM.

In view of the fact that the volume of the eye in a given subject is known (for example, typical human eye contains 4 to 6 mL of fluid (humor)) it is possible to calculate the dosage of the necrostatin and/or the pan-caspase inhibitor to be administered to give the therapeutically effective concentrations noted above. For example, from about 0.035 mg to about 2 mg of necrostatin-1 and from about 0.05 mg to about 1.5 mg of a pan-caspase inhibitor can be administered to achieve the concentrations noted above.

In certain embodiments, from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the necrosis inhibitor (e.g., a necrostatin) can be administered locally to the eye of a mammal. In one embodiment, 0.5 mg of necrostatin is administered locally to the eye of a mammal. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of an apoptosis inhibitor (e.g., a pan-caspase inhibitor, e.g., Z-VAD) can be administered locally to the eye of a mammal. In certain embodiments, about 0.7 mg of a pan-caspase inhibitor, e.g., Z-VAD, is administered locally to the eye of a mammal.

It is understood that one or more of a necrosis inhibitor, one or more of an apoptosis inhibitor, or one or more of a necrosis inhibitor and one or more of an apoptosis inhibitor can be administered to the eye in which a region of the retina has been affected in amounts sufficient to preserve the viability of photoreceptor cells disposed within the region of the affected retina.

In certain embodiments, the necrosis inhibitor is a necrostatin, for example, necrostatin-1, a necrostatin-2, a necrostatin-4, a necrostatin-5, and a necrostatin-7. One or more of these necrosis inhibitors can be administered with one or more of the apoptosis inhibitors (e.g., IDN-6556) listed below. Furthermore, it is contemplated that one or more of the necrostatins shown by Formua I, I-A, I-B, I-C, I-D, I-E, I-F, I-G, II, II-A, III, IV, IV-A, IV-B, V, V-A, VII, VIII, VIII-A, IX, or IX-A can be administered with one or more of the apoptosis inhibitors (e.g., IDN-6556 or IDN-6734) listed below.

In certain embodiment, the necrosis inhibitor reduces the production and/or activity of a RIP-1 kinase and/or a RIP-3 kinase. RIP kinase inhibitors (e.g., RIP-1 kinase and/or RIP-3 kinase inhibitors) as disclosed herein may further include RNAs, including small inhibitory RNAs (siRNAs) and short hairpin RNAs (shRNAs). Methods for designing and synthesizing siRNAs and shRNAs are well known in the art. Exemplary RIP-1 kinase inhibitors include, for example, a pSIREN-RIP-1 shRNA construct which targets RIP-1 kinase as disclosed in Kaiser et al. (2008) JOURNAL OF IMMUNOLOGY 181:6427-6434. Exemplary RIP-3 kinase inhibitors include, for example, sc-61482-SH and sc-135170 available from Santa Cruz Biotechnology. In another example, RIP kinase inhibitors (e.g., RIP-1 kinase and/or RIP-3 kinase inhibitors) as disclosed herein may include inhibitor of apoptosis proteins (IAPB), active fragments thereof, and nucleic acids encoding the same. It is well established that IAPB inhibit RIP-1 kinase by functioning as a E3 ligase for RIP-1 kinase (see, for example, Vanlangenakker et al. (2010) CELL DEATH AND DIFFERENTIATION 18: 656-665).

In certain embodiments, the one or more apoptosis inhibitors may include a pan-caspase inhibitor. The pan-caspase inhibitor can be Z-VAD (i.e., Z-Val-Ala-Asp(OMe)-CH$_2$F*), IDN-6556 available from Conatus Pharmaceuticals (i.e., (3-{2-[(2-tert-butyl-phenylaminoooxalyl)-amino]-propionylamino}-4-oxo-5-(2,3,5,6-tetrafluoro-phenoxy)-pentanoic acid) (3-{2-[(2-tert-butyl-phenylaminoooxalyl)-amino]-propionylamino}-4-oxo-5-(2,3,5,6-tetrafluoro-phenoxy)-pentanoic acid), IDN-6734 available from Conatus Pharmaceuticals, VX-799 available from Vertex Pharmaceuticals, MX1013 and MX2060 derivatives available from Maxim Pharmaceuticals, M-920 available from Merck-Frosst, small-molecule compounds available from Gemin X Pharmaceuticals, RGD peptides from Merck-Frost and Maxim Pharmaceuticals, or any other known pan-caspase inhibitor.

Alternatively, the pan-caspase inhibitor can be a cocktail of caspase inhibitors including two or more specific caspase inhibitors (e.g., synthetic caspase inhibitors) such as a caspase 1 inhibitor, a caspase 2 inhibitor, a caspase 3 inhibitor, a caspase 4 inhibitor, a caspase 5 inhibitor, a caspase 6 inhibitor, a caspase 7 inhibitor, a caspase 8 inhibitor, and a caspase 9 inhibitor. It is contemplated that one or more of the pan-caspase inhibitors may be used in combination with one or more necrostatins (e.g., necrostain-1 and/or necrostatin-4).

Exemplary synthetic caspase 1 inhibitors, include, for example, Ac-N-Me-Tyr-Val-Ala-Asp-aldehyde, Ac-Trp-Glu-His-Asp-aldehyde, Ac-Tyr-N-Me-Val-Ala-N-Me-Asp-aldehyde, Ac-Tyr-Val-Ala-Asp-Aldehyde, Ac-Tyr-Val-Ala-Asp-chloromethylketone, Ac-Tyr-Val-Ala-Asp-2,6-dimethylbenzoyloxymethylketone, Ac-Tyr-Val-Ala-Asp(OtBu)-aldehyde-dimethyl acetol, Ac-Tyr-Val-Lys-Asp-aldehyde, Ac-Tyr-Val-Lys(biotinyl)-Asp-2,6-dimethylbenzoyloxymethylketone, biotinyl-Tyr-Val-Ala-Asp-chloromethylketone, Boc-Asp(OBzl)-chloromethylketone, ethoxycarbonyl-Ala-Tyr-Val-Ala-Asp-aldehyde (pseudo acid), Z-Asp-2,6-dichlorobenzoyloxymethylketone, Z-Asp(OlBu)-bromomethylketone, Z-Tyr-Val-Ala-Asp-chloromethylketone, Z-Tyr-Val-Ala-DL-Asp-fluoromethlyketone, Z-Val-Ala-DL-Asp-fluoromethylketone, and Z-Val-Ala-DL-Asp(OMe)- fluoromethylketone, all of which can be obtained from Bachem Bioscience Inc., PA. Other exemplary caspase 1 inhibitors include, for example, Z-Val-Ala-Asp-fluoromethylketone, biotin-X-Val-Ala-Asp-fluoromethylketone, Ac-Val-Ala-Asp-aldehyde, Boc-Asp-fluoromethylketone, Ac-Ala-Ala-Val-Ala-Leu-Leu-Pro-Ala-Val-Leu-Leu-Ala-Leu-Leu-Pro-Tyr-Val-Ala-Asp-aldehyde (SEQ ID NO: 1), biotin-Tyr-Val-Ala-Asp-fluoroacyloxymethylketone, Ac-Tyr-Val-Ala-Asp-acyloxymethylketone, Z-Asp-CH2-DCB, and Z-Tyr-Val-Ala-Asp-fluoromethylketone, all of which are available from Calbiochem, IDN-11104 available from Conatus Pharmaceuticals, and VX-740 and VX-756 available from Vertex Pharmaceuticals.

Exemplary synthetic caspase 2 inhibitors, include, for example, Ac-Val-Asp-Val-Ala-Asp-aldehyde, which can be obtained from Bachem Bioscience Inc., PA, and Z-Val-Asp-Val-Ala-Asp-fluoromethylketone, which can be obtained from Calbiochem, CA.

Exemplary synthetic caspase 3 precursor protease inhibitors include, for example, Ac-Glu-Ser-Met-Asp-aldehyde (pseudo acid) and Ac-Ile-Glu-Thr-Asp-aldehyde (pseudo acid) which can be obtained from Bachem Bioscience Inc., PA. Exemplary synthetic caspase 3 inhibitors include, for example, Ac-Asp-Glu-Val-Asp-aldehyde, Ac-Asp-Met-Gin-Asp-aldehyde, biotinyl-Asp-Glu-Val-Asp-aldehyde, Z-Asp-Glu-Val-Asp-chloromethylketone, Z-Asp(OMe)-Glu(OMe)-Val-DL-Asp(OMe)-fluoromethylketone, and Z-Val-Ala-DL-Asp(OMe)-fluoromethylketone which can be obtained from Bachem Bioscience Inc., PA. Other exemplary caspase 3 inhibitors include, for example, Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), biotin-X-Asp-Glu-Val-Asp-fluoromethylketone, Ac-Asp-Glu-Val-Asp-chloromethylketone, all of which are available from Calbiochem. Another exemplary caspase 3 inhibitor includes, the caspase 3 inhibitor N-benzyloxycarbonal-Asp(OMe)-Glu(OMe)-Val-Asp(Ome)-fluoromethyketone (z-Asp-Glu-Val-Asp-fmk), which is available from Enzyme Systems Products. Additional exemplary caspase 3 inhibitors include M-826 and M-791 available from Merck-Frosst, Immunocasp-3, Ad-G/iCasp3, and PEF-F8-CP3.

Exemplary synthetic caspase 4 inhibitors include, for example, Ac-Leu-Glu-Val-Asp-aldehyde and Z-Tyr-Val-Ala-DL-Asp-fluoromethylketone, which can be obtained from Bachem Bioscience Inc., PA, and Ac-Ala-Ala-Val-Ala-Leu-Leu-Pro-Ala-Val-Leu-Leu-Ala-Leu-Leu-Ala-Pro-Leu-Glu-Val-Pro-aldehyde (SEQ ID NO: 3), which can be obtained from Calbiochem, CA.

Exemplary synthetic caspase 5 inhibitors include, for example, Z-Trp-His-Glu-Asp-fluoromethylketone, which can be obtained from Calbiochem, CA, and Ac-Trp-Glu-His-Asp-aldehyde and Z-Trp-Glu(O-Me)-His-Asp(O-Me) fluoromethylketone, which can be obtained from Sigma Aldrich, Germany.

Exemplary synthetic caspase 6 inhibitors include, for example, Ac-Val-Glu-Ile-Asp-aldehyde, Z-Val-Glu-Ile-Asp-fluoromethylketone, and Ac-Ala-Ala-Val-Ala-Leu-Leu-Pro-Ala-Val-Leu-Leu-Ala-Leu-Leu-Ala-Pro-Val-Glu-Ile-Asp-aldehyde (SEQ ID NO: 4), which can be obtained from Calbiochem. Another exemplary caspase 6 inhibitor includes Immunocasp-6.

Exemplary synthetic caspase 7 inhibitors include, for example, Z-Asp(OMe)-Gln-Met-Asp(OMe) fluoromethylketone, Ac-Asp-Glu-Val-Asp-aldehyde, Biotin-Asp-Glu-Val-Asp-fluoromethylketone, Z-Asp-Glu-Val-Asp-fluoromethylketone, Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), which can be obtained from Sigma Aldrich, Germany.

Exemplary synthetic caspase 8 inhibitors include, for example, Ac-Asp-Glu-Val-Asp-aldehyde, Ac-Ile-Glu-Pro-Asp-aldehyde, Ac-Ile-Glu-Thr-Asp-aldehyde, Ac-Trp-Glu-His-Asp-aldehyde and Boc-Ala-Glu-Val-Asp-aldehyde which can be obtained from Bachem Bioscience Inc., PA. Other exemplary caspase 8 inhibitors include, for example, Ac-Ala-Ala-Val-Ala-Leu-Leu-Pro-Ala-Val-Leu-Leu-Ala-Leu-Leu-Ala-Pro-Ile-Glu-Thr-Asp-aldehyde (SEQ ID NO: 5) and Z-Ile-Glu-Thr-Asp-fluoromethylketone, which can be obtained from Calbiochem, CA.

Exemplary synthetic caspase 9 inhibitors, include, for example, Ac-Asp-Glu-Val-Asp-aldehyde, Ac-Leu-Glu-His-Asp-aldehyde, and Ac-Leu-Glu-His-Asp-chloromethylketone which can be obtained from Bachem Bioscience Inc., PA. Other exemplary caspase 9 inhibitors include, for example, Z-Leu-Glu-His-Asp-fluoromethylketone and Ac-Ala-Ala-Val-Ala-Leu-Leu-Pro-Ala-Val-Leu-Leu-Ala-Leu-Leu-Ala-Pro-Leu-Glu-His-Asp-aldehyde (SEQ ID NO:6), which can be obtained from Calbiochem, CA. Another exemplary caspase 9 inhibitor includes FKBP12/caspase-9 fusion protein.

The pan-caspase inhibitor may also be an endogenous caspase inhibitor or a combination of an endogenous caspase inhibitor with one or more synthetic caspase inhibitors. For example, one useful class of endogenous caspase inhibitor includes proteins known as inhibitors of apoptosis proteins (IAPB) (Deveraux et al. (1998) EMBO J. 17(8): 2215-2223) including bioactive fragments and analogs thereof. One exemplary IAP includes X-linked inhibitor of apoptosis protein (XIAP), which has been shown to be a direct and selective inhibitor of caspase-3, caspase-7 and caspase-9. Another exemplary IAP includes survivin (see, U.S. Pat. No. 6,245,523; Papapetropoulos et al. (2000) J. BIOL. CHEM. 275: 9102-9105), including bioactive fragments and analogs thereof. Survivin has been reported to inhibit caspase-3 and caspase-7 activity.

In certain embodiments, the one or more apoptosis inhibitors may target the inhibitor of apoptosis proteins (IAPB) and second mitochondria-derived activator of caspases (SMACs). Exemplary apoptosis inhibitors that target IAPB and SMACs, include, for example, BIR3 antagonists available from Idun Pharmaceuticals, capped tripeptide XIAP antagonists from Abbot Laboratories, TWX024, polyphenylurea derivatives, SMAC-mimetic compounds, embelin, XIAP antisense and RNAi constructs, AEG35156/GEM®640 available from Aegera Therapeutics, HIV-Tat- and polyarginine conjugated SMAC peptides, and nonpeptide small-molecule SMAC mimetics. It is contemplated that one or more of the apoptosis inhibitors which target IAPB and SMACs may be used in combination with one or more necrostatins (e.g., necrostain-1 and/or necrostatin-4).

In certain embodiments, the one or more apoptosis inhibitors may target the TNF-related apoptosis-inducing ligand (TRAIL) receptors. Exemplary apoptosis inhibitors that target the TRAIL receptors, include, for example, HGS-ETR1, HGS-ETR2, and HGS-TR2J available from Human Genome Sciences, and PRO1762 available from Amgen. It is contemplated that one or more of the apoptosis inhibitors which target the TRAIL receptors may be used in combination with one or more necrostatins (e.g., necrostain-1 and/or necrostatin-4).

In certain embodiments, the one or more apoptosis inhibitors may target CD95/Fas. Exemplary apoptosis inhibitors that target CD95/FAS, include, for example, CD95-Fc available from ApoGenix GmbH. It is contemplated that one or more of the apoptosis inhibitors which target CD95/Fas may be used in combination with one or more necrostatins (e.g., necrostain-1 and/or necrostatin-4).

In certain embodiments, the one or more apoptosis inhibitors may be an anti-FasL factors. Exemplary anti-FasL factors include, for example, anti-FasL neutralizing antibody (available, for example, from Pharmingen, San Diego, Calif.); peptides and nucleic acids (for example, anti-FasL aptamers) that bind FasL to prevent or reduce its binding to its cognate receptor; certain antibodies and antigen binding fragments thereof and peptides that bind preferentially to the Fas receptor; antisense nucleotides and double stranded RNA for RNAi that ultimately reduce or eliminate the production of either FasL or the Fas receptor; soluble Fas; soluble FasL; decoy receptor-3 (DcR3) and analogues thereof; matrix metalloproteinases (MMPs); vasoactive intestinal peptide (VIP); pituitary adenylate cyclase-activating polypeptide (PACAP); forskolin; combined use of benazepril and valsartan; nonpeptidic corticotropin-releasing hormone receptor type 1 (CRH-R1)-specific antagonists; mimosine; peptides that produce a defective Fas-FasL complex; platelet-activating factor (PAF); and endothelin-1 (ET-1). These anti-FasL factors can act as direct or indirect antagonists of FasL activity.

In certain embodiments, the one or more apoptosis inhibitors may target the tumor necrosis factor (TNF). Exemplary apoptosis inhibitors that target TNF, include, for example, recombinant TNF-α, adalimumab available from Abbott, infliximab available from Centocor Ortho Biotech Inc., etanercept from Amgen, CDP571 available from Celltech, and ISIS 104838 (a 2'-O-methoxyethyl antisense construct against TNF-alpha) available from ISIS Pharmaceuticals. It is contemplated that one or more of the apoptosis inhibitors which target TNF may be used in combination with one or more necrostatins (e.g., necrostain-1 and/or necrostatin-4).

In certain embodiments, the one or more apoptosis inhibitors may target survivin. Exemplary apoptosis inhibitors that target survivin, include, for example, LY2181308 available from ISIS Pharmaceuticals and Ad-survivin T34A. It is contemplated that one or more of the apoptosis inhibitors which target survivin may be used in combination with one or more necrostatins (e.g., necrostain-1 and/or necrostatin-4).

In certain embodiments, the one or more apoptosis inhibitors may target the Bcl-2 proteins. Exemplary apoptosis inhibitors that target the Bcl-2 proteins, include, for example, Bcl-2 blockers available from Idun Pharmaceuticals and Abbot Laboratories, Gx01 series of compounds available from Gemin X Pharmaceuticals, Bcl-2 small-molecule antagonist, Tetrocarcin-A derivatives available from Kyowa Hakko Kogyo Co., Chelerythrine, antimycin A derivatives, HA14-1, synthetic compound binding to the BH3 of Bcl-2, Genasense available from Sanofi-Aventis, ISIS 22783 available from ISIS Pharmaceuticals, bispecific Bcl-2/Bcl-XL antisense, BH3 peptides from Bax, Bak, Bid or Bad, SAHBs, and BH3Is. It is contemplated that one or more of the apoptosis inhibitors which target the Bcl-2 proteins may be used in combination with one or more necrostatins (e.g., necrostain-1 and/or necrostatin-4).

In certain embodiments, the one or more apoptosis inhibitors may target p53. Exemplary apoptosis inhibitors that target p53, include, for example, INGN201 available from Invitrogen Therapeutics, SCH58500 available from Schering-Plough, ONYX-015 available from Onyx Pharmaceuticals, C-terminal p53 peptides, CDB3, Amifostine, CP31398 available from Pfizer, Prima-1, HPF E6-binding peptide aptamers, Nutlins available from Roche, Chalcones, Small peptide compounds, and Pifithrin-a. It is contemplated that one or more of the apoptosis inhibitors which target p53 may be used in combination with one or more necrostatins (e.g., necrostain-1 and/or necrostatin-4).

In certain embodiments, it is contemplated that one or more necrostatins (e.g., necrostatin-1 and/or necrostatin-4) may be used in combination with a pan-caspase inhibitor. For example, in one embodiment, necrostain-1 and/or necrostatin-4 may be used in combination with Z-VAD available from R&D Systems (Cat. No. FMK001) and Promega (Cat. No. G7231). In another embodiment, necrostain-1 and/or necrostatin-4 may be used in combination with IDN-6556 available from Conatus Pharmaceuticals. In yet another embodiment, necrostain-1 and/or necrostatin-4 may be used in combination with IDN-6734 available from Conatus Pharmaceuticals.

In certain embodiments, it is contemplated that one or more necrostatins (e.g., necrostatin-1 and/or necrostatin-4) may be used in combination with a TNF inhibitor. For example, in one embodiment, necrostain-1 and/or necrostatin-4 may be used in combination with adalimumab available from Abbot Laboratories. In another embodiment, necrostain-1 and/or necrostatin-4 may be used in combination with etanercept available from Amgen, Inc. In yet another embodiment, necrostain-1 and/or necrostatin-4 may be used in combination with infiximab available from Centocor Ortho Biotech, Inc.

In certain embodiments, it is contemplated that one or more necrostatins (e.g., necrostatin-1 and/or necrostatin-4) may be used in combination with a p53 agonist. For example, in one embodiment, necrostain-1 and/or necrostatin-4 may be used in combination with INGN 201 available from Invitrogen Therapeutics. In another embodiment, necrostain-1 and/or necrostatin-4 may be used in combination with nutlins, for example, nutlin-3 available from Cayman Chemical (Cat. No. 10004372). In yet another embodiment, necrostain-1 and/or necrostatin-4 may be used in combination with CP31398 available from Tocris Bioscience (Cat. No. 3023).

In certain embodiments, it is contemplated that one or more necrostatins (e.g., necrostatin-1 and/or necrostatin-4) may be used in combination with an anti-FasL factor. For example, in one embodiment, necrostain-1 and/or necrostatin-4 may be used in combination with anti-FasL neutralizing antibody available from Pharmingen (San Diego, Calif.).

Figure 19:
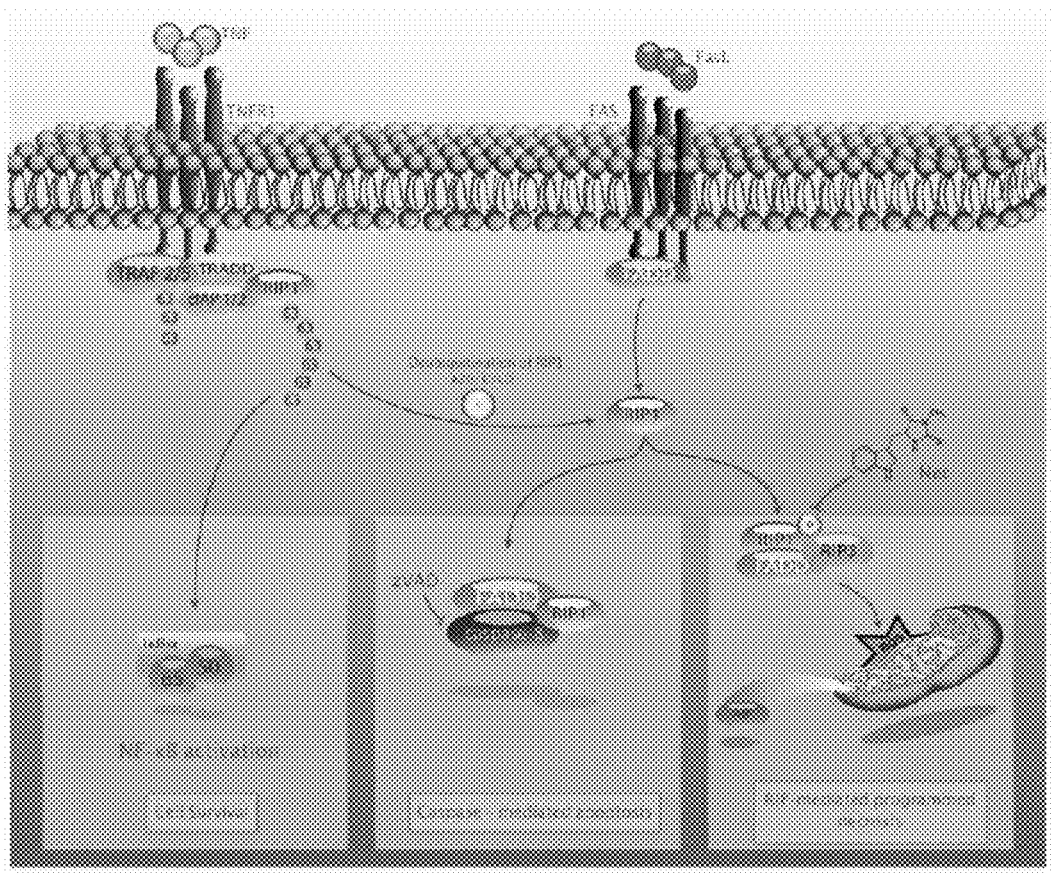
FIG. 19 is another schematic diagram of the RIP-1 signaling pathway.

As shown in FIG. 1A and FIG. 19, depending upon the specific apoptotic inhibitor chosen, it is possible that the apoptotic inhibitor can modulate both the apoptotic and necrotic pathways, and depending upon the specific necrosis inhibitor chosen, it is possible that the necrosis inhibitor can modulate both the necrotic and apoptotic pathways. For example, a RIP-1 inhibitor may inhibit both necrotic and apoptotic cell death thus preserving the viability of the photoreceptor and/or RPE cells in the retina of the eye of a subject with an ocular condition as disclosed herein.

As discussed herein, the methods and compositions of the invention can preserve the visual function of an eye of a subject with an ocular condition. Visual function can be measured using one or more of a variety of methods well-known in the art. For example, visual function can be assessed by measuring visual acuity. Visual acuity can be assessed, for example, by using conventional "eye charts" in which visual acuity is evaluated by the ability to discern letters of a certain size, with five letters of a given size present on each line (see, e.g., the "ETDRS" eye chart described in the Murphy, R. P., CURRENT TECHNIQUES IN OPTHALMIC LASER SURGERY, 3$^{rd}$ Ed., edited by L. D. Singerman, and G. Cascas, Butterworth Heinemann, 2000). Evaluation of visual acuity may also be achieved by measuring reading speed and reading time. Visual acuity may be measured to evaluate whether administration of a necrosis inhibitor and/or an apoptosis inhibitor to the affected eye preserves or permits improvement of visual acuity (e.g., to 20/40 vision or to 20/20 vision).

Visual function may also be measured by determining whether there is an increase in the thickness of the macula (e.g., macula thickness is 15% thicker than, 35% thicker than, 50% thicker than, 60% thicker than, 70% thicker than, or 80% thicker than a macula without the treatment as measured by optical coherence tomography (OCT); an improvement of the photoreceptor cell layer or its subdivisions as seen in the OCT; an improvement of visual field (e.g., by at least 10% in the mean standard deviation on the Humphrey Visual Field Test; an improvement of an electroretinograph (ERG), a measurement of the electrical response of the retina to light stimulation, (e.g., to increase ERG amplitude by at least 15%); and or preservation or improvement of multifocal ERG, which evaluates the response of the retina to multifocal stimulation and allows characterization of the function of a limited area of the retina.

Visual function may also be measured by electrooculography (EOG), which is a technique for measuring the resting potential of the retina. EOG is particularly useful for the assessment of RPE function. EOG may be used to evaluate whether administration of a necrosis inhibitor and/or an apoptosis inhibitor to the retina of the affected eye preserves or permits improvement in, for example, the Arden ratio (e.g., an increase in Arden ratio of at least 10%).

Visual function may also be assessed through fundus autofluorescence (AF) imaging, which is a clinical tool that allows evaluation of the interaction between photoreceptor cells and the RPE. For example, increased fundus AF or decreased fundus AF has been shown to occur in AMD and other ocular disorders. Fundus AF imaging may be used to evaluate whether administration of a necrosis inhibitor and/or an apoptosis inhibitor to the retina of the affected eye slows disease progression.

Visual function may also be assessed by evaluation of contrast sensitivity, which a measurement of the ability to discern between luminances of different levels in a static image. An evaluation of contrast sensitivity may be used to assess whether administration of a necrosis inhibitor and/or an apoptosis inhibitor to the retina of the affected eye preserves or permits improvement in the resolving power of the eye.

Visual function may also be assessed by microperimetry, which monitors retinal visual function against retinal thickness or structure and the condition of the subject's fixation over time. Microperimetry may be used to assess whether administration of a necrosis inhibitor and/or an apoptosis inhibitor to the retina of the affected eye preserves or permits improvement in retinal sensitivity and fixation.

It is understood that the methods and compositions described herein can be used to preserve the viability of photoreceptor and retinal pigment epithelial cells during treatment of the underlying conditions, e.g., AMD, RP, etc.

With regard to preserving the viability of photoreceptor cells following retinal detachment, it is contemplated herein that the necrosis inhibitor, e.g., a necrostatin, and/or an apoptosis inhibitor, e.g., a pan-caspase inhibitor such as Z-VAD or IDN-6556, may be administered before, during and/or after surgical reattachment of the detached retina. The necrosis inhibitor and/or the apoptosis inhibitor may be administered to the mammal from the time the retinal detachment is detected to the time the retina is repaired, for example, via surgical reattachment. The retina may be surgically reattached using procedures known in the art. An exemplary procedure for surgically reattaching a retina following detachment includes removing the vitreous fluid and aqueous humor from the eye and applying a gas, e.g., fluoropropane, to push the retina against the choroid. Alternatively, buckle surgery, which does not require removing the vitreous fluid and aqueous humor from the eye, may be performed to reattach the retina.

It is understood, however, that under certain circumstances, it may be beneficial to administer the necrosis inhibitor, e.g., a necrostatin, and/or the apoptosis inhibitor, e.g., a pan-caspase inhibitor such as Z-VAD or IDN-6556, even after the retina has been surgically repaired following retinal detachment. For example, even after the surgical reattachment of a detached retina in patients with rhegmatogenous retinal detachments, persistent subretinal fluid may exist under the fovea as detected by ocular coherence tomography long after the surgery has been performed (see, Hagimura et al. (2002) AM. J. OPHTHALMOL. 133:516-520). As a result, even after surgical repair the retina may still not be completely reattached to the underlying retinal pigment epithelium and choroid. Furthermore, when retinal detachments occur secondary to another disorder, for example, the neovascular form of age-related macular degeneration and ocular melanomas, as noted above, it may be beneficial to administer the necrosis inhibitor, the apoptosis inhibitor, or both the necrosis inhibitor and the apoptosis inhibitor to the individual while the underlying disorder is being treated so as to minimize loss of photoreceptor cell viability. Accordingly, in such cases, it may be beneficial to administer the necrosis inhibitor and/or the apoptosis inhibitor to the mammal for one week, two weeks, three weeks, one month, three months, six months, nine months, one year, two years or more (i) after retinal detachment has been identified, and/or (ii) after surgical reattachment of the retina has occurred, and/or (iii) after detection of an underlying degenerative disorder, so as to minimize photoreceptor cell death.

In certain embodiments, the necrosis inhibitor, e.g., a necrostatin, and/or the apoptosis inhibitor, e.g., a pan-caspase inhibitor such as Z-VAD or IDN-6556, may be administered locally to the eye of a subject, e.g., a human subject, following surgical reattachment of the retina or other treatments of the retina to preserve or to permit improvement of visual acuity (e.g., to 20/40 vision or to 20/20 vision); to increase the thickness of the macula (e.g., macula thickness is 15% thicker than, 35% thicker than, 50% thicker than, 60% thicker than, 70% thicker than, or 80% thicker than a macula without the treatment as measured by optical coherence tomography (OCT)); to permit improvement in the appearance and structure of the photoreceptor cell layer and its supporting RPE, to permit the improvement of visual field (e.g., by at least 10% in the mean standard deviation on the Humphrey Visual Field Test; and/or to permit the improvement of an electroretinograph (ERG), a measurement of the electrical response of the retina to light stimulation, (e.g., to increase ERG amplitude by at least 15%).

In certain embodiments, the necrosis inhibitor, e.g., a necrostatin, and/or the apoptosis inhibitor, e.g., a pan-caspase inhibitor such as Z-VAD or IDN-6556, are administered locally to the eye of a mammal by intravitreal injection. Both agents may be administered on the day of diagnosis and/or the same day that the retina is surgically reattached or has gone through other treatments and/or in the post-operative period. The agents may then be administered every three days, every five days, or every seven days until the mammal, e.g., a human, has improved vision (e.g., visual acuity has improved to 20/40 vision or to 20/20 vision), the thickness of the macula has increased (e.g., macula thickness is 15% thicker than, 35% thicker than, 50% thicker than, 60% thicker than, 70% thicker than, or 80% thicker than without treatment as measured by OCT); the appearance of the photoreceptor cell layer and RPE as detected by OCT; the visual field has improved by at least 10% in the mean standard deviation as determined by Humphrey Visual Field testing; and/or the mammal's retina shows an increased response to light stimulation (e.g., at least a 15% increase in amplitude as determined by electroretinography).

The necrosis inhibitor and the apoptosis inhibitor can be administered by the same route or by different routes. The necrosis inhibitor and/or the apoptosis inhibitor may be administered locally to the eye, for example, by intravitreal, intraocular, intraorbital, subconjuctival, subretinal or transscleral routes. For example, the necrosis inhibitor and/or the apoptosis inhibitor may be administered locally to the eye by intravitreal injection. It is contemplated that local modes of administration may reduce or eliminate the incidence of potential side effects (e.g., systemic toxicity) that may occur during systemic administration.

Alternatively, the necrosis inhibitor and/or the apoptosis inhibitor may be administered systemically, e.g., by oral or parenteral routes. Parenteral routes include, for example, intravenous, intrarterial, intramuscular, intradermal, subcutaneous, intranasal and intraperitoneal routes.

The necrosis inhibitor and the apoptosis inhibitor may be administered to a subject simultaneously or sequentially. It will be appreciated that when administered simultaneously, the necrosis inhibitor and the apoptosis inhibitor may be in the same pharmaceutically acceptable carrier (e.g., solubilized in the same viscoelastic carrier that is introduced into the eye) or the two drugs may be dissolved or dispersed in separate pharmaceutical carriers, which are administered at the same time. Alternatively, the drugs may be provided in separate dosage forms and administered sequentially. For example, in some embodiments, the necrostatin may be administered before the pan-caspase inhibitor. In other examples, the pan-caspase inhibitor may be administered before the necrostatin. In addition, it is appreciated that, in some embodiments, a single active agent may inhibit both necrosis and apoptosis.

Administration may be provided as a periodic bolus (for example, intravitreally or intravenously) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag, or a contact lens slow release formulation system). The necrosis inhibitor and/or the apoptosis inhibitor may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) INVEST. OPHTHALMOL. VIS. SCI. 41:1181-1185, and Ambati et al. (2000) INVEST. OPHTHALMOL. SCI. 41:1186-1191). A variety of devices suitable for administering the disclosed necrosis and/or apoptosis inhibitors locally to the inside of the eye are known in the art. See, for example, U.S. Pat. Nos. 6,251,090, 6,299,895, 6,416,777, 6,413,540, and 6,375,972, and PCT/US00/28187.

The necrosis inhibitor and/or the apoptosis inhibitor may be solubilized in a carrier, for example, a viscoelastic carrier, that is introduced locally into the eye. One or both inhibitors also may be administered in a pharmaceutically acceptable carrier or vehicle so that administration does not otherwise adversely affect the recipient's electrolyte and/or volume balance. The carrier may comprise, for example, physiologic saline or other buffer system. In exemplary embodiments, the necrostatin, the pan-caspase inhibitor, or both the necrostatin and the pan-caspase inhibitor may be solubilized in PBS or another aqueous buffer by sonication. Alternatively, one or both drugs may be solubilized using conventional solvent or solubilization systems, for example, dimethyl sulfoxide (DMSO), dimethoxyethane (DME), dimethylformamide (DMF), cyclodextran, micelles, liposomes, liposomal agents, and other solvents known in the art to aid in the solubilization and administration of hydrophobic agents.

In other embodiments, the necrosis inhibitor and/or the apoptosis inhibitor may be solubilized in a liposome or microsphere. Methods for delivery of a drug or combination of drugs in liposomes and/or microspheres are well-known in the art.

In addition, it is contemplated that the necrosis inhibitor and/or the apoptosis inhibitor may be formulated so as to permit release of one or both inhibitors over a prolonged period of time. A release system can include a matrix of a biodegradable material or a material, which releases the incorporated active agents. The active agents can be homogeneously or heterogeneously distributed within a release system. A variety of release systems may be useful in the practice of the invention, however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, under certain circumstances, synthetic release systems are preferred because generally they are more reliable, more reproducible and produce more defined release profiles. The release system material can be selected so that inhibitors having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

One of the primary vehicles currently being developed for the delivery of ocular pharmacological agents is the poly (lactide-co-glycolide) microsphere for intraocular injection. The microspheres are composed of a polymer of lactic acid and glycolic acid, which are structured to form hollow spheres. These spheres can be approximately 15-30 µm in diameter and can be loaded with a variety of compounds varying in size from simple molecules to high molecular weight proteins such as antibodies. The biocompatibility of these microspheres is well established (see, Sintzel et al. (1996) EUR. J. PHARM. BIOPHARM. 42: 358-372), and microspheres have been used to deliver a wide variety of pharmacological agents in numerous biological systems. After injection, poly(lactide-co-glycolide) microspheres are hydrolyzed by the surrounding tissues, which cause the release of the contents of the microspheres (Zhu et al. (2000) NAT. BIOTECH. 18: 52-57). As will be appreciated, the in vivo half-life of a microsphere can be adjusted depending on the specific needs of the system.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

EXAMPLES

The invention is further illustrated by the following examples, which are provided for illustrative purposes only, and should not be construed as limiting the scope or content of the invention in any way.

In the examples described herein, all animal experiments adhered to the Association for Research in Vision and Ophthalmology Statement for the Use of Animals in Ophthalmic and Vision Research, and protocols were approved by the Animal Care Committee of the Massachusetts Eye and Ear Infirmary. Adult male Brown Norway rats (200 to 300 g) and WT C57BL/6 mice were purchased from Charles River Laboratories (Wilmington, Mass.). The mice were fed standard laboratory chow and allowed free access to water in an air-conditioned room with a 12 hour light/12 hour dark cycle. RIP-3 knockout (RIP-3−/−) mice were kindly provided by Dr. V. M. Dixit (Genentech, San Francisco, Calif.). RIP-3−/− mice were generated as described previously and backcrossed to C57BL/6 mice (Newton et al. (2004) MOL CELL BIOL 24:1464-9). Rd10 mice were purchased from the Jackson Laboratory (Bar Harbor, Me.). CCL2/Cx3Cr1 double knockout mice were kindly provided by Dr. Chi-Chao Chan (National Eye Institute and National Institutes of Health, Bethesda, Md.). CCL2/Cx3Cr1/RIP-3 triple knockout mice were generated by breeding CCL2/Cx3Cr1 double knockout mice with RIP-3 knockout mice.

The following reagents are utilized: Z-VAD (Alexis, Plymouth Meeting Pa.), IDN-6556 (kindly provided by TetraLogics Pharmaceuticals), a Nec-1 compound of Formula I-C (a kind gift from Dr. J. Yuan, Harvard Medical School, Boston, Mass.), and a Nec-4 compound of Formula IV-A (kindly provided by TetraLogics Pharmaceuticals).

Experimental retinal detachment was induced as previously described (Hisatomi T et al. (2001) AM. J. PATHOL. 158:1271-1278. Briefly, a 30-gauge needle was inserted into the subretinal space via an external transscleral transchoroidal approach, and 1% sodium hyaluronate (Provisc; Alcon, Fort Worth, Tex.) containing either vehicle (control), Z-VAD (300 µM), IDN-6556 (200 µM), a Nec-1 compound of Formula I-C (400 µM), and/or Nec-4 compound of Formula IV-A (200 µM) was gently injected into the subretinal space to enlarge the retinal detachment.

All values disclosed below were expressed as the mean±SD. Statistical differences between two groups were analyzed by Mann-Whitney Utest. Multiple group comparison was performed by ANOVA followed by Tukey-Kramer adjustments. Differences were considered significant at $P<0.05$.

Example 1

Increased Expression of RIP-3 and RIP-1 after Retinal Detachment

Photoreceptor death after retinal detachment has been thought to be caused mainly by apoptosis (Cook et al. (1995) INVEST OPHTHALMOL VIS SCI 36: 990-996; Arroyo et al. (2005) AM J OPHTHALMOL 139:605-610. Although caspase-dependent pathway is known to be activated after retinal detachment, caspase inhibition by pan-caspase inhibitor fails to prevent photoreceptor death (Zacks et al. (2003) INVEST OPHTHALMOL VIS SCI 44: 1262-1267; Hisatomi et al. (2001) AM J OPHTHALMOL 158:1271-1278). In this example, other pathways leading to photoreceptor death were investigated. In particular, the expression levels of RIP-1 and RIP-3 proteins were measured after retinal detachment. RIP-3 is a key regulator of RIP-1 kinase activation (Galluzzi L et al. (2009) J. MOL. CELL BIOL.) and its expression level has been shown to correlate with responsiveness to programmed necrosis (He S et al. (2009) CELL 137:1100-1111). As described below, it was demonstrated that necrotic photoreceptor death occurs after retinal detachment although its frequency is about half that of apoptosis.

Total RNA extraction and reverse transcription were performed as previously reported (Nakazawa et al. (2006) MOL. VIS. 12:867-878; Hisatomi et al. (2008). J. CLIN. INVEST. 118:2025-2038). A real-time PCR assay was performed with Prism 7700 Sequence Detection System (Applied Biosystems, Foster City, Calif.). TaqMan Gene Expression assays were used to check the expression of RIP-1 (Rn01757378_m1) and RIP-3 (Rn00595154_m1). For relative comparison of each gene, the Ct value of real-time PCR data was analyzed with the ΔΔCt method and normalized by an endogenous control (18S ribosomal RNA).

Partial sequence of mouse RIP-3 gene was amplified by RT-PCR using primers AGCACAGGACACATCAGTTGG and CTTGAGGCAGTAGTTCTTGGTG, and cloned into the pCR-II vector (Invitrogen). Digoxigenin-labeled riboprobe was hybridized at 61° C. overnight, followed by stringent washes. The cryosections were then treated with an alkaline phosphatase-conjugated antidigoxigenin antibody (Roche, Indianapolis, Ind.). Hybridization signals were visualized with BM purple AP substrate (Roche).

The vitreous and neural retina combined was collected on day 3 after retinal detachment. Samples were run on 4-12% SDS-polyacrylamide gel electrophoresis and transferred onto PVDF membrane. After blocking with 3% nonfat dried milk, the membrane was reacted with RIP-3 (1:10000; Sigma, Saint Louis, Mo.), RIP-1 (1:2000; BD Biosciences), phosphoserine (1:2000; Enzo, Plymouth Meeting, Pa.) or anti-phosphorylated NF-κB p65 (1:1000; Cell signaling) antibody. Membranes were then developed with enhanced chemiluminescence. Lane-loading differences were normalized by β-tubulin (1:1000; Cell Signaling).

Equal amount of retinal lysates (1 mg) were incubated with 1 µg anti-RIP-1 antibody (BD Biosciences) and 20 µl of Protein A/G Agarose beads (Thermo Scientific, Rockford, Ill.) at 4° C. overnight. Beads were washed 5 times with lysis buffer and TBS, and the immunopellets were then subjected to Western blotting.

The expression levels of RIP-3 and RIP-1 mRNA were assessed in the retina three days after retinal detachment by quantitative real-time PCR. This time point was chosen because photoreceptor death peaks at three days after retinal detachment (Hisatomi T et al. (2001) AM. J. PATHOL. 158: 1271-1278). FIG. 1B-C provide graphs showing the quantitative real-time PCR analysis for RIP-3 (FIG. 1B) and RIP-1 (FIG. 1C) in control retina without retinal detachment and in retina three days after retinal detachment (n=9 each; **, P<0.01). RIP-3 expression increased 12-fold after retinal detachment compared to that in untreated retina (P=0.0003; FIG. 1B). RIP-1 expression also increased 2-fold after retinal detachment (P=0.0031; FIG. 1C).

Protein expression of RIP-3 and RIP-1 after retinal detachment (n=4 each) was analyzed by Western blot. Lane-loading differences were normalized by levels of β-tubulin. For RIP-3 analysis, spleen samples from wild-type (WT) and RIP-3−/− animals were used as positive and negative controls, respectively. The bar graphs indicate the relative level of RIP-3 and RIP-1 to β-tubulin by densitometric analysis, reflecting the results from four independent experiments (*, P<0.05). Western blot analysis confirmed that RIP-3 protein expression increased over 10-fold after retinal detachment (P=0.0209; FIG. 1D, black arrowhead: RIP-3; white arrowhead: non-specific band).

Figure 2:
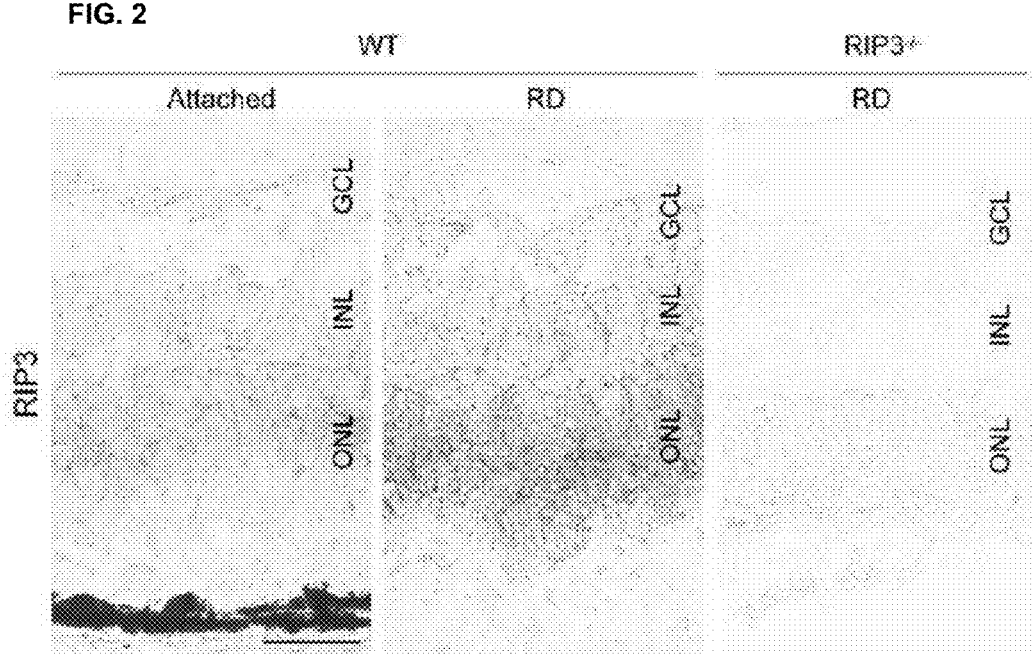
FIG. 2 depicts photographs showing results of in situ hybridization analysis of RIP-3.

In situ hybridization analysis of RIP-3 was also conducted. RIP-3 signal was detected in retinal tissues, especially in the outer nuclear layer (ONL) after retinal detachment. The retina from RIP-3−/− animals was used as negative control. In situ hybridization showed that RIP-3 signal was detected in neurosensory retina, especially in the ONL, after retinal detachment (FIG. 2; GCL: ganglion cell layer; INL: inner nuclear layer; scale bar, 50 µm).

These data indicate that RIP-mediated programmed necrosis is involved in photoreceptor loss after retinal detachment.

Example 2

Necrosis Inhibitor Prevents Retinal Detachment-Induced Photoreceptor Death in Combination with a Caspase Inhibitor Necrostatin-1 (Nec-1) is a potent and selective inhibitor of programmed necrosis, which targets RIP-1 kinase activity (Degterev A et al. (2008) NAT. CHEM. BIOL. 4:313-321). The effectiveness of a RIP-1 kinase inhibitor in combination with a capsase inhibitor to prevent retinal detachment induced photoreceptor death was investigated.

Figure 3A:
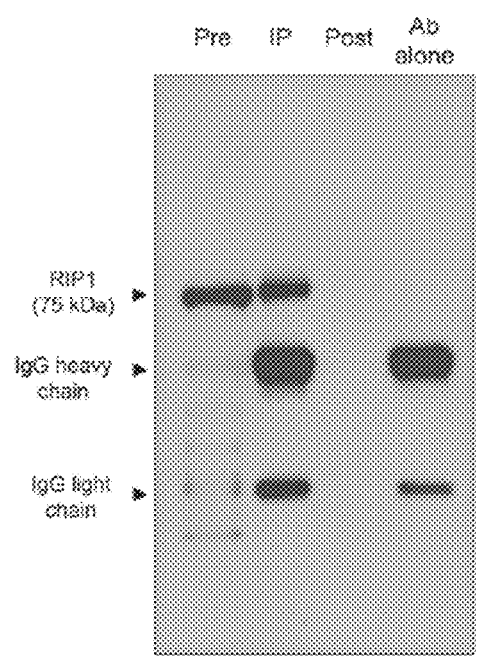
FIG. 3A-B are photographs of immunoblots of an immunoprecipitation of RIP-1 from retinal lysates (FIG. 3A) and phosphorylation of RIP-1 after retinal detachment (FIG. 3B).

RIP-1 is phosphorylated at several serine residues in its kinase domain during programmed necrosis and Nec-1 inhibits this phosphorylation (Degterev (2008) supra; Cho Y et al. (2009) Cell 137:1100-1111). To investigate the role of RIP-1 kinase in retinal detachment-induced photoreceptor death, the phosphorylation status of RIP-1 was first assessed by immunoprecipitating RIP-1 from the retina (FIG. 3A) and then blotting with an anti-phosphoserine antibody. RIP-1 was immunoprecipitated from retinal lysates. One mg of retinal lysates were incubated with anti-RIP-1 antibody and Protein A/G agarose beads. Extracts before (Pre) and after (Post) immunoprecipitation and the immunopellets (IP) were run on a 4-12% SDS-PAGE and blotted with anti-RIP-1 antibody. Anti-RIP-1 antibody alone was used as negative control. Extracts post-immunoprecipitation showed almost complete immunodepletion of RIP-1 from the retinal extract.

Figure 3B:
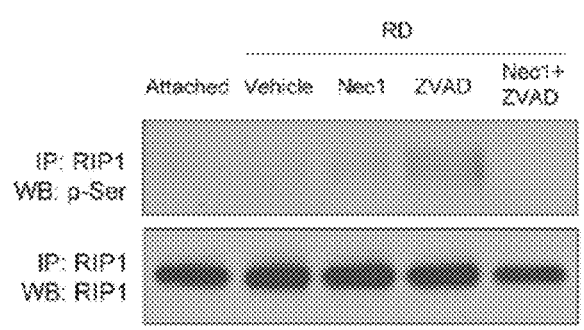

To determine the effect of Nec-1 and a pan-caspase inhibitor on the phosphorylation of RIP-1, Z-VAD (300 µM) and/or a Nec-1 compound of Formula I-C(400 µM) were injected subretinally in the animal at the time of retinal detachment induction. The dosage of compounds was selected based on previous studies which established that the half-life of the compounds is around 6 hours in the subretinal space. RIP-1 was immunoprecipitated from lysates of untreated retina and of retina treated with either vehicle, Nec-1, Z-VAD, or Nec-1+Z-VAD at two days after retinal detachment. Phosphorylation of RIP-1 was then assessed by Western blot analysis. After retinal detachment, RIP-1 phosphorylation was elevated in Z-VAD-treated retina compared to untreated retina (FIG. 3B). As shown in FIG. 3B, Nec-1 and Z-VAD combination treatment substantially inhibited this increase in RIP-1 phosphorylation.

Photoreceptor death was also assessed by TUNEL analysis at three days after retinal detachment in retina treated with either vehicle, Nec-1, Z-VAD or Nec-1+Z-VAD. TUNEL and quantification of TUNEL positive cells in ONL were performed as previously described (Nakazawa T et al. (2007) PROC. NATL. ACAD. SCI. USA 104:2425-2430) by using the ApopTag Fluorescein In Situ Apoptosis Detection Kit (Millipore, Billerica, Mass.). The ratio of the thickness of the ONL to the thickness of neuroretina in the central area of the detached retina was determined by National Institutes of Health ImageJ software and standardized by that in the attached retina. The data are expressed as normalized ONL thickness ratio [(ONL/neuroretina thickness in detached retina)/(ONL/neuroretina thickness in attached retina)]. Nine sections for each eye specimen were randomly selected, and the central area of detached retina and the mid-peripheral region of attached retina were photographed. The ONL thickness ratio was measured at ten points in each section by masked observers. The data are expressed as normalized ONL thickness ratio [(ONL/neuroretina thickness in detached retina/(ONL/neuroretina thickness in attached retina)]. FIG. 4A shows TUNEL (green) and DAPI (blue) staining in detached retina treated with vehicle, Z-VAD, Nec-1 (a Nec-1 of Formula I-C) or Nec-1+Z-VAD on day three after retinal detachment. FIG. 4B-C show quantification of TUNEL-positive photoreceptors (FIG. 4B) and ONL thickness ratio (FIG. 4C) on day three (vehicle, n=12; Z-VAD, n=12; Nec-1, n=6; Z-VAD+Nec-1, n=12) and day five (vehicle, n=8; Z-VAD, n=8; Nec-1, n=6; Z-VAD+Nec-1, n=8) after retinal detachment. (GCL: ganglion cell layer, INL: inner nuclear layer. *, P<0.05. Scale bar, 100 µm).

Treatment with Z-VAD or Nec-1 alone showed no significant effect on the number of TUNEL-positive cells in the ONL (1134.7±297.5 and 1067.5±95.5 cells/mm$^2$, respectively), as compared with vehicle treatment (1366.3±103.7 cells/mm$^2$; FIG. 4A-B). In comparison, combined treatment with Nec-1+Z-VAD significantly reduced the number of TUNEL-positive cells in the ONL (573.1±154.3 cells/mm$^2$, P<0.05; FIG. 4A-B). The appearance of TUNEL-positive cells was decreased to approximately 200 cells/mm$^2$ in each group five days after retinal detachment (FIG. 4B). Although detection of DNA fragmentation by TUNEL is used as a marker of apoptosis, it has been reported that necrosis, programmed or otherwise, also yields DNA fragments that react with TUNEL in vivo, rendering it difficult to discriminate between apoptosis and necrosis (Grasl-Kraupp B et al. (1995) HEPATOLOGY 21: 1465-1468).

The thickness ratio of ONL to the total retinal thickness in detached retina compared to normal attached retina was also measured. The normalized ONL thickness ratio was reduced to 0.65±0.10 in vehicle-treated detached retina three days (bars with stippled shading in FIG. 4C) after retinal detachment. Treatment with Z-VAD or Nec-1 alone had no protective effect on the reduction of ONL thickness ratio (0.72±0.08 and 0.71±0.09, respectively); whereas Z-VAD+Nec-1 treatment significantly prevented the reduction in retinal thickness (0.92±0.06, P<0.05; FIGS. 4A and 4C). Photoreceptor loss was more severe five days (bars with solid shading in FIG. 4C) after retinal detachment; with a normalized ONL thickness ratio reduced to 0.52±0.08 in vehicle-treated animals, 0.54±0.10 in Z-VAD-treated animals and 0.58±0.12 in Nec-1-treated animals, with substantial, synergistic preservation of retinal thickness in animals treated with Nec-1+Z-VAD (0.81±0.06, P<0.05; FIG. 4C).

Figure 5A:
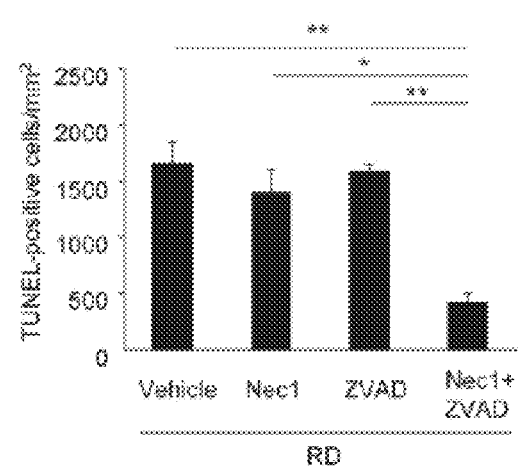
FIG. 5A-B are graphs showing that intravitreal injection of Z-VAD+Nec-1 at one day after retinal detachment prevents photoreceptor loss when measured three days after retinal detachment.
Figure 5B:
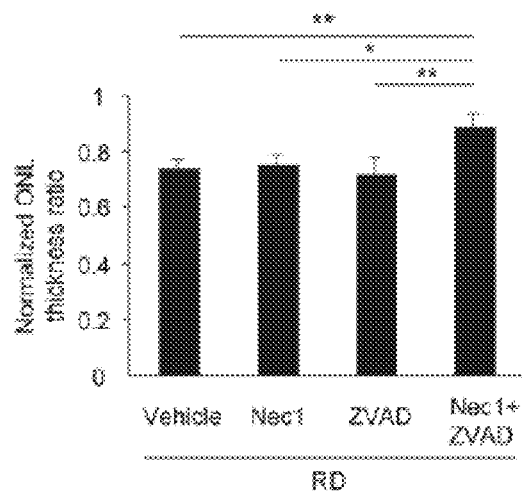

Treatment with both Nec-1 and Z-VAD also showed efficient neuroprotection when the compounds were injected intravitreally one day after retinal detachment induction. FIG. 5A-B shows quantification of TUNEL-positive photoreceptors (FIG. 5A) and ONL thickness ratio (FIG. 5B) on day three after retinal detachment in rats (n=4-5). Five µl of Nec-1 (2 mM) and/or Z-VAD (3 mM) were injected intravitreally one day after retinal detachment-induced photoreceptor death. Treatment with Nec-1+Z-VAD significantly decreased the number of TUNEL-positive cells and prevented the reduction of ONL thickness ratio after retinal detachment. *, P<0.05; **, P<0.01.

The effects of another necrostatin, Nec-4 (Teng et al., (2008) BIOORG MED CHEM LETT, 18: 3219-3223) and/or another pan-caspase inhibitor (IDN-6556—labeled PCI in FIG. 6A-F) (Hoglen N C et al. (2004) J PHARMACOL EXP THER 309:634-640) on retinal detachment-induced photoreceptor death were also assessed. TUNEL-positive photoreceptors were quantitated (FIG. 6 A, 6C, 6E) and ONL thickness ratio was measured (FIGS. 6 B, 6D, and 6F) on day three after retinal detachment in rats (n=5-6). Nec-4 (a compound of Formula IV-A), IDN-6556 and/or Z-VAD were injected subretinally at the doses indicated in FIG. 6A-F. Nec-4 or IDN-6556 alone did not show any neuroprotective effect (FIG. 6 A-D), while Nec-4+IDN-6556 and Nec-4+Z-VAD combination treatments significantly suppressed photoreceptor loss after retinal detachment (FIG. 6E-F) (P<0.05; **, P<0.01). Nec-4 and IDN-6556 were prepared as described in Teng et al., (2008) BIOORG MED CHEM LETT, 18: 3219-3223 and Hoglen et al. ((2004) J PHARMACOL EXP THER 309:634-640), respectively. These data indicate that RIP-1 kinase mediates photoreceptor death after retinal detachment in the presence of a pan-caspase inhibitor. As a result, simultaneous inhibition of both caspase and RIP-1 kinase pathways significantly limits photoreceptor death after retinal detachment. As demonstrated herein, the co-administration of a RIP-1 inhibitor, e.g., necrostatin-1 or necrostatin-4, and a pan-caspase inhibitor, e.g., Z-VAD or IDN-6556, achieved a synergistic effect compared to treatment with either drug alone. Co-administration of a RIP-1 inhibitor, e.g., necrostatin-1 or necrostatin-4, and a pan-caspase inhibitor, e.g., Z-VAD or IDN-6556, may be used to prevent vision loss in various retinal disorders associated with retinal detachment and other degenerative diseases.

Figure 15A:
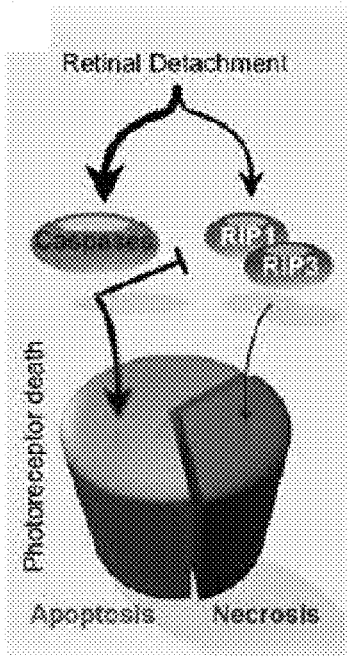
FIG. 15A-C are schematic representations showing a proposed mechanism of photoreceptor loss after retinal detachment.
Figure 15B:
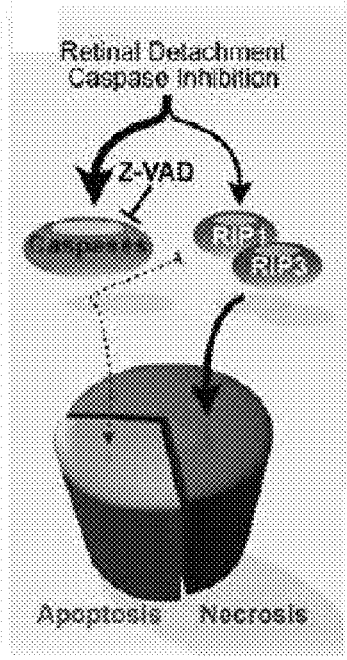
Figure 15C:
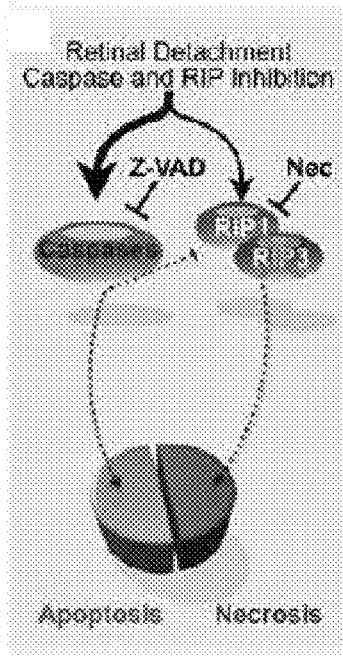

Consistent with our findings, Arimura et al. showed that the vitreous level of high-mobility group box1 protein, which is known to be released from necrotic cells but not apoptotic cells, is increased in human eyes with retinal detachment (Arimura et al. (2009) LAB INVEST 89: 278-289; Scaffidi et al. (2002) Nature 418:191-195). Furthermore, we found that Z-VAD treatment decreases apoptosis but increases necrotic photoreceptor death after retinal detachment, and that Nec-1 co-treatment effectively suppresses necrotic photoreceptor death. These findings clearly demonstrate programmed necrosis as an essential and complementary mechanism of photoreceptor death, which is further revealed when caspases are inhibited (FIG. 15A-C). In other retinal degenerative conditions such as inherited retinal degeneration and light-induced retinal injury, it has been shown that the photoreceptor death is not prevented by Z-VAD (Donovan & Cotter (2002) CELL DEATH DIFFER 9:1220-1231; Sanges et al. (2006) PROC NATL ACAD SCI USA 103:17366-17371; Murakami et al. (2008) AM J PATHOL 173-1326-1338), and thus it may be possible that programmed necrosis may underlie the death execution in these diseases as well.

Example 3

Caspase Inhibition Shifts Retinal Detachment-Induced Photoreceptor Death from Apoptosis to Programmed Necrosis The morphology of photoreceptors after retinal detachment was examined by transmission electron microscopy (TEM) and propidium iodide (PI) staining and the effect of treatment with Z-VAD and/or a Nec-1 compound of Formula I-C was analyzed.

TEM was performed as previously described (Hisatomi T et al. (2008). J. CLIN. INVEST. 118:2025-2038). The specimens were observed with Philips CM10 electron microscope. Over 200 photoreceptors each eye were photographed and subjected to quantification of cell death modes in a masked fashion. Photoreceptors showing cellular shrinkage and nuclear condensation were defined as apoptotic cells, while photoreceptors associated with cellular and organelle swelling and discontinuities in nuclear and plasma membrane were defined as necrotic cells. The presence of electron-dense granular materials were reported to occur subsequent to both apoptotic and necrotic cell death and cells with these findings were labeled simply as end-stage cell death/unclassified (Hisatomi T et al. (2003) AM. J. PATHOL. 162:1869-1879; Erickson P A et al. (1983) INVEST. OPHTHALMOL. VIS. SCI. 24:927-942).

FIG. 7A-E show TEM photomicrographs in the ONL on day three after retinal detachment in retina treated with vehicle (FIG. 7A), Z-VAD (FIG. 7B) or Nec-1+Z-VAD (the Nec-1 compound was a compound of Formula I-C) (FIG. 7C). On day three after retinal detachment, photoreceptor death caused by apoptosis was almost twice that caused by necrosis in vehicle-treated retina (% apoptotic cells: 21.7±1.3%, necrotic cells: 13.3±1.0%, unclassified: 4.4±1.4%; FIGS. 7A and 7E). Nec-1 treatment did not affect the percentage of apoptotic and necrotic cells after retinal detachment (% apoptotic cells: 19.8±2.0%, necrotic cells: 13.1±1.4%, unclassified: 2.8±0.4%; FIGS. 7 B and 7E). In comparison, Z-VAD treatment significantly decreased apoptotic photoreceptor death and increased necrotic cell death (% apoptotic cells: 11.4±1.2%, necrotic cells: 21.9±2.3%, unclassified: 5.6±1.4%, P<0.05; FIGS. 7 C and 7E). However, Nec-1 combined with Z-VAD substantially prevented the switch to necrotic cell death and led to a decrease in both forms of cell loss (% apoptotic cells: 6.9±2.9%, necrotic cells: 9.8±0.7%, unclassified: 1.0±0.2%, P<0.01; FIGS. 7D and 7E). FIG. 7E shows the quantification of apoptotic and necrotic photoreceptor death after retinal detachment (n=4 each).

These results indicate that Z-VAD, as compared with vehicle, increased necrotic cells and decreased apoptotic cells (P<0.05), and that Nec-1 combined with Z-VAD significantly suppressed necrotic cell death (P<0.01, vs. Z-VAD) (scale bar, 50 μm).

In vivo propidium iodide (PI) staining was performed by injecting 5 μl of PI (50 μg/ml) into the subretinal space three days after retinal detachment. After two hours, the eyes were enucleated and 10 μm thick cryosections were cut, air-dried, and fixed in 100% ethanol. DAPI was used to counterstain the nuclei. The center of the detached retina was photographed by fluorescence microscope, and the number of PI-positive cells in ONL was analyzed by ImageJ software.

FIG. 8A-D shows PI staining (FIG. 8A) and quantification of PI-positive photoreceptors (B) on day three after retinal detachment in retina treated with vehicle, Z-VAD or Nec-1+Z-VAD (the Nec-1 compound was a compound of Formula I-C) in wild-type retina (n=6 each). Consistent with the transmission electron microscopy findings, subretinal injection of PI prior to enucleation, a technique to demonstrate cells with disrupted cell membrane, showed increased number of PI-positive photoreceptors in Z-VAD-treated retina (817.4±104.2 cells/mm$^2$) compared to vehicle-treated retina three days after retinal detachment (366.5±82.1 cells/mm$^2$, P<0.05; FIG. 8A-B). Treatment with Nec-1+Z-VAD significantly suppressed the number of PI-positive cells in the ONL (16.0±7.6 cells/mm$^2$, P<0.05: FIG. 8A-B). (*, P<0.05; **, P<0.01; scale bar, 100 μm.)

Collectively, these results indicate that programmed necrosis as well as apoptosis are involved in photoreceptor death after retinal detachment, and that RIP-1-mediated programmed necrosis becomes a predominant form of photoreceptor death when the caspase-dependent apoptotic pathway is inhibited.

Example 4

RIP-3 Deficiency Inhibits Induction of Programmed Necrosis and Prevents Photoreceptor Death after Retinal Detachment The role of RIP-3 in RIP-mediated programmed necrosis in photoreceptor loss after retinal detachment was investigated in RIP-3 knockout (RIP-3–/–) mice. TUNEL assays were used to measure the amount of apoptotic and necrotic cell death (Grasl-Kraupp et al., HEPTALOGY (1995) 21(5): 1465-8). TUNEL and quantification of TUNEL positive cells in ONL were performed as described above by using the ApopTag Fluorescein In Situ Apoptosis Detection Kit (Millipore, Billerica, Mass.). The ratio of the ONL thickness to the thickness of neuroretina in the central area of the detached retina was determined by National Institutes of Health ImageJ software and standardized by that in the attached retina. The data are expressed as normalized ONL thickness ratio [(ONL/neuroretina thickness in detached retina)/(ONL/neuroretina thickness in attached retina)].

Figure 9A:
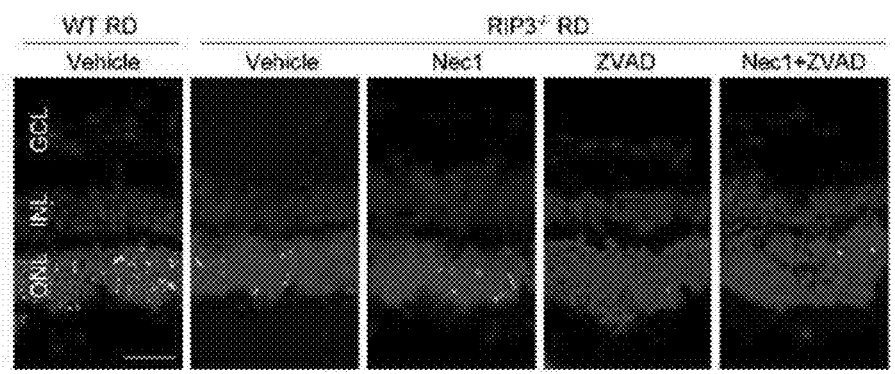
FIG. 9A-C are TUNEL photographs (FIG. 9A) and graphs (FIGS. 9B and 9C) showing the reduction of photoreceptor cell death following retinal detachment in RIP-3−/− mice and in RIP-3−/− mice treated with Z-VAD.
Figure 9B:
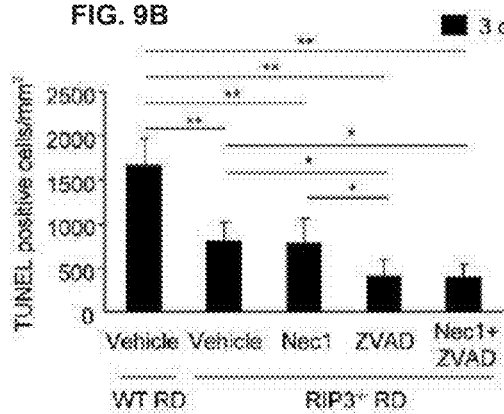
Figure 9C:
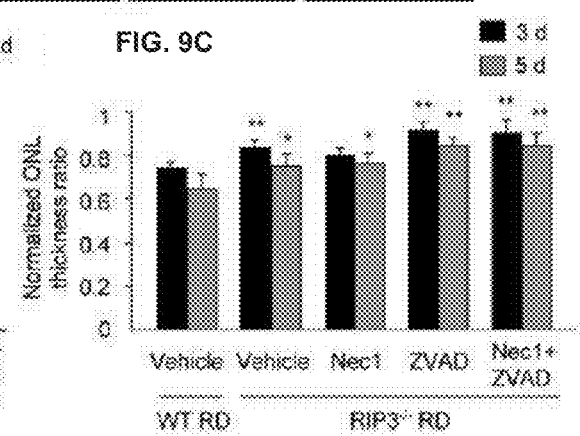

FIG. 9A shows TUNEL (green) and DAPI (blue) staining in detached retina in WT and RIP-3–/– mice treated with vehicle, Z-VAD, Nec-1, or Nec-1+Z-VAD (the Nec-1 compound was a compound of Formula I-C) at three days after retinal detachment. FIG. 9B shows quantification of TUNEL-positive photoreceptors on day three after retinal detachment (vehicle in WT mice, n=6; vehicle in RIP-3–/– mice, n=7; Z-VAD in RIP-3–/– mice, n=7; Nec-1+Z-VAD in RIP-3–/– mice, n=6). FIG. 9C shows ONL thickness on day three (vehicle in WT mice, n=6; vehicle in RIP-3–/– mice, n=7; Nec-1 in RIP-3–/– mice, n=8; Z-VAD in RIP-3–/– mice, n=7; Nec-1+Z-VAD in RIP-3–/– mice, n=6) and day five (vehicle in WT mice, n=7; vehicle in RIP-3–/– mice, n=6; Nec-1 in RIP-3–/– mice, n=6; Z-VAD in RIP-3–/– mice, n=6; Nec-1+Z-VAD in RIP-3–/– mice, n=6) after retinal detachment (*, P<0.05; **, P<0.01. Scale bar, 50 μm).

Without retinal detachment, the morphology of the retina and ONL thickness ratio were similar in RIP-3–/– and wild-type (WT) mice. Three days after retinal detachment, RIP-3–/– mice showed significantly less TUNEL-positive cells (804.7±204.5 cells/mm$^2$) than WT mice (1668.7±305.8 cells/mm$^2$, P<0.01; FIGS. 9A and 9B). In contrast to WT animals, Z-VAD treatment in RIP-3–/– mice further decreased the number of TUNEL-positive cells after retinal detachment (407.7±188.9 cells/mm$^2$, P<0.05, vs. RIP-3–/– mice treated with vehicle), whereas Nec-1 did not provide any additional effect (786.7±278.7 cells/mm$^2$; FIGS. 9A and 9B). RIP-3–/– retinas exhibited preserved ONL thickness ratio, which was augmented by Z-VAD treatment, on day 3 and 5 after retinal detachment (FIG. 9C).

In summary, suppression of RIP-3 gene expression in the RIP-3–/– mice significantly reduced the number of TUNEL positive cells consistent with RIP-3 playing a role in mediating programmed necrosis. Treatment with Z-VAD in the RIP-3–/– mice further reduced the number of TUNEL-positive cells in the ONL. In comparison, treatment with Z-VAD and Nec-1 did not result in further reductions in the number of TUNEL-positive cells in the ONL in the RIP-3–/– mice three days after retinal detachment (FIG. 9B) suggesting that the amount of necrotic cell death in RIP-3–/– mice is similar to the amount of necrotic cell death observed in mice treated with Nec-1.

The thickness ratio of ONL to the total retinal thickness in detached retina compared to normal attached retina was also measured (FIG. 9C). The normalized ONL thickness ratio increased in RIP-3–/– mice compared to WT mice five days after retinal detachment (WT: 0.644±0.064; RIP-3–/–: 0.754±0.049) suggesting that RIP-3–/– mice have a protective effect compared to WT mice following retinal detachment. Treatment with Nec-1 in RIP-3–/– mice did not provide any further protection following retinal detachment (RIP-3–/–+Nec1: 0.761±0.049); whereas treatment with Z-VAD in RIP-3–/– mice significantly prevented a reduction in retinal thickness (RIP-3–/–+ZVAD: 0.841±0.042).

Figure 10A:
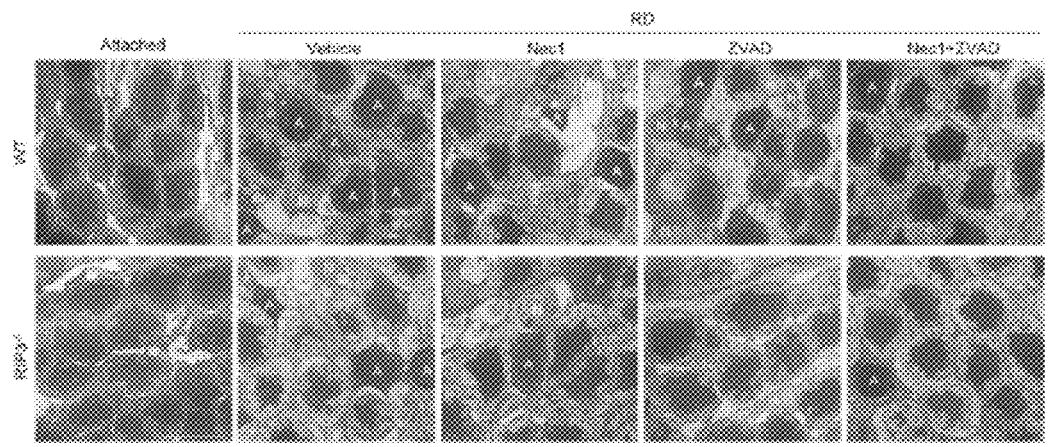
FIG. 10A-B are TEM photographs in the ONL on day 3 after retinal detachment in wild-type and RIP-3−/− retina treated with vehicle, Z-VAD, Nec-1, or Z-VAD+Nec-1.
Figure 10B:
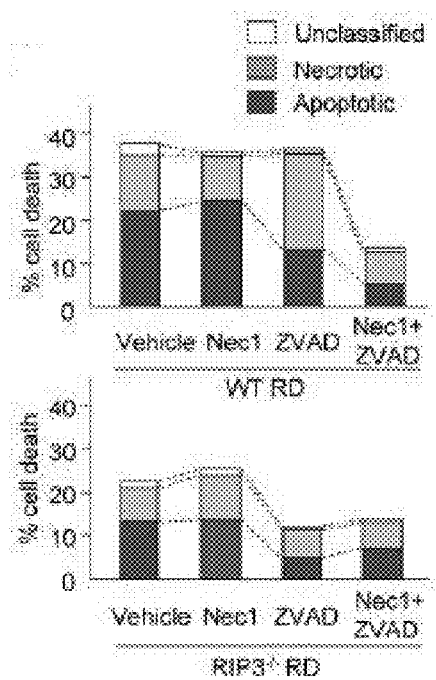

The morphology of the RIP-3–/– retina after retinal detachment was also assessed by TEM. In WT mice, the percentage of necrotic photoreceptors was significantly increased by Z-VAD treatment (% apoptotic cells: 13.3±1.5%, necrotic cells: 22.1±1.0%, unclassified: 1.0±0.6%) compared to vehicle treatment (% apoptotic cells: 22.2±4.0%, necrotic cells: 13.0±2.1%, unclassified: 2.5±1.3%, P<0.05; FIGS. 10A and B). In contrast, in RIP-3–/– mice, Z-VAD treatment substantially prevented photoreceptor death after retinal detachment without inducing necrotic cell death (% apoptotic cells: 4.8±1.3%, necrotic cells: 6.4±1.3%, unclassified: 0.9±0.4%). FIG. 10A shows TEM micrographs in the ONL on day three after retinal detachment in WT and RIP-3–/– retina treated with vehicle, Nec-1 (a Nec-1 of Formula 1-C), Z-VAD, or Nec-1+Z-VAD. In untreated attached retina, the retinal morphology was similar in WT and RIP-3–/– mice (A: apoptotic cell. N: Necrotic cell.) FIG. 10B shows the quantification of apoptotic and necrotic photoreceptor death after retinal detachment (n=4 each). RIP-3 deficiency inhibits the switch to necrotic cell death by Z-VAD treatment and prevents photoreceptor death after retinal detachment. Scale bar, 5 µm.

Consistent with these results, the number of photoreceptors with disrupted plasma membrane, as assessed by in vivo PI-labeling, was not increased by Z-VAD treatment in RIP-3−/− retinas (FIGS. 8C and 8D), confirming that RIP-3 plays an essential role to induce programmed necrosis after retinal detachment, especially in the presence of a caspase inhibitor. FIG. 8C-D show PI staining (FIG. 8C) and quantification of PI-positive photoreceptors (FIG. 8D) on day 3 after retinal detachment in retina treated with vehicle, Z-VAD or Nec-1 (a Nec-1 of Formula I-C) and Z-VAD in RIP-3−/− retina (n=5-6; C and D). *, P<0.05; **, P<0.01. Scale bar, 100 µm. In the WT mice, treatment with Z-VAD showed an increase in the number of PI-positive photoreceptors compared to vehicle-treated retina three days after retinal detachment suggesting increased necrotic cell death in pan-caspase inhibited photoreceptor cells. In comparison, treatment with Z-VAD in the RIP-3−/− mice did not show an increase in the number of PI-positive cells in the ONL indicating that there was no shift to necrotic cell death in the RIP-3−/− cells following treatment with a pan-caspase inhibitor after retinal detachment.

In addition, RIP-3−/− retinas showed less apoptotic cells after retinal detachment (% apoptotic cells: 13.4±1.1%, necrotic cells: 8.1±1.0%, unclassified: 1.2±0.5%) compared to WT retinas, suggesting that RIP-3 may be involved not only in RIP-1-mediated programmed necrosis but also in other cell death pathways. Alternatively, the kinetics of a single administration of Nec-1 to inhibit RIP kinase is different than the chronic loss of RIP kinase activity in RIP-3−/− animals.

These data indicate that RIP-3 mediates necrotic photoreceptor death after retinal detachment. Suppression of RIP-3 gene expression significantly limits necrotic photoreceptor death after retinal detachment via a similar pathway to Nec-1 treatment. Treatment with Nec-1 does not provide additional protection in RIP-3−/− mice. However, administration of Z-VAD in a RIP-3−/− mouse significantly limits photoreceptor death after retinal detachment suggesting that blocking both necrosis and apoptosis mediated cell death may be used to prevent vision loss in various retinal disorders associated with retinal detachment. Thus, RIP-3 deficiency provides neuroprotection after retinal detachment that is augmented by Z-VAD. These results indicate that the suppression of RIP-3 expression prevents a shift of retinal detachment-induced photoreceptor death from apoptosis to programmed necrosis following treatment with a pan-caspase inhibitor. These data further indicate that RIP-3 mediates programmed necrosis and that blockade of the RIP Kinase pathway is important and necessary in addition to blockade of the caspase pathway for effective protection of photoreceptor cells form cell death.

Example 5

RIP-1 Kinase Mediates Inflammatory Reactions after Retinal Detachment

In this example, the role of RIP-1 kinase activity in inflammatory reactions after retinal detachment was investigated.

Immunohistochemistry (IHC) was performed as previously reported (Murakami Y et al. (2008) AM J PATHOL 173:1326-1338). Rat anti-CD1 lb antibody (1:50; BD Biosciences, San Diego, Calif.) was used as the primary antibody. The specimens were imaged by confocal microscopy using the Leica HCX APOL40X lens.

Immunofluorescence was performed as previously reported (Hisatomi et al. (2008) J CLIN INVEST 118:2025-2038. The enucleated eyes were frozen in OCT compound (Sakura Finetechnical Co., Tokyo, Japan). Five µm-thick sections were cut, air dried and fixed in cold acetone for 10 minutes. Rat anti-CD11b (1:50; BD Biosciences, San Diego, Calif.) was used as the primary antibody and incubated at 4° C. overnight. A nonimmune serum was used as a negative control. Alexa Fluor 594-conjugated goat anti-rat IgG (Invitrogen, Carlsbad, Calif.) was used as the secondary antibody and incubated at room temperature for one hour. The specimens were imaged by confocal microscopy using the Leica HCX APOL40X lens.

Total RNA extraction and reverse transcription were performed as previously reported (Nakazawa T et al. (2006) MOL VIS 12: 867-878; Hisatomi T et al. (2008). J CLIN INVEST 118:2025-2038). A real-time PCR assay was performed with Prism 7700 Sequence Detection System (Applied Biosystems, Foster City, Calif.). TaqMan Gene Expression assays were also used to check the expression of MCP-1 (Rn00580555_m1), TNF-α (Rn99999017_m1), and Fas-L (Rn00563754_m1). For relative comparison of each gene, the Ct value of real-time PCR data was analyzed with the ΔΔCt method and normalized by an endogenous control (18S ribosomal RNA).

In addition, the MCP-1 protein contents in rat retina were determined using ELISA Kit for rat MCP-1 (Thermo, Rockford, Ill.).

Figure 11A:
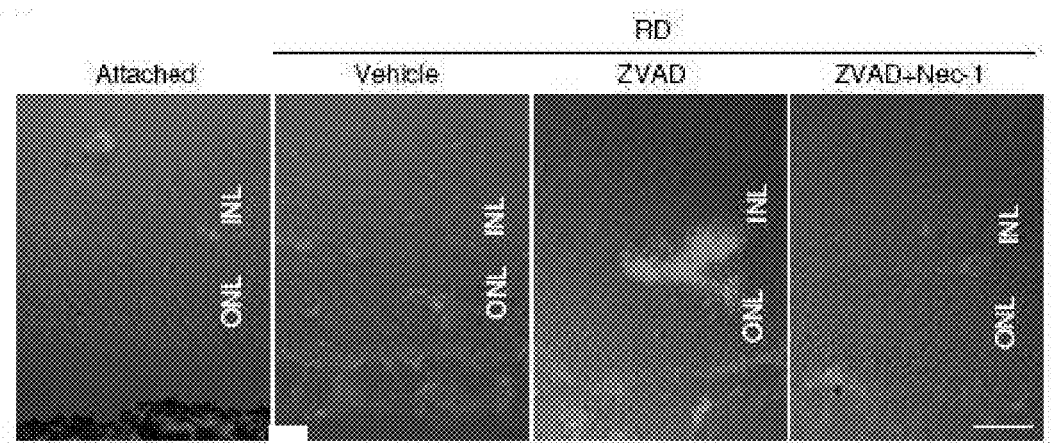
FIG. 11A-F are photographs and graphs showing that Nec-1 suppressed the inflammatory response after retinal detachment.
Figure 11B:
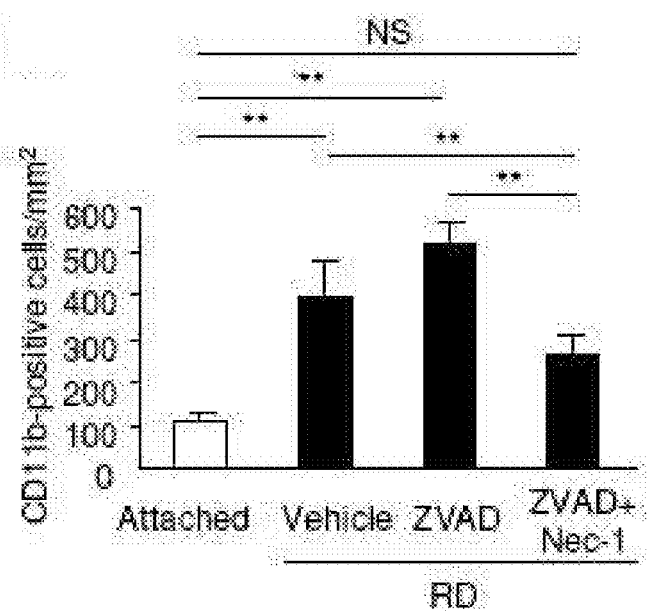

Since the release of intracellular content in necrosis results in secondary inflammation, changes in the inflammatory response after retinal detachment were investigated by immunohistochemistry and immunofluorescence with an antibody against CD11b. FIG. 11A-B show IHC for CD11b (FIG. 11A) and quantification of CD11b-positive cells in control retina without retinal detachment and in retina treated with vehicle, Z-VAD or Z-VAD+Nec-1 (n=6 each) (FIG. 11B) at three days after retinal detachment. (*, P<0.05; **, P<0.01; NS, not significant; Scale bar, 50 µm). On day three after retinal detachment, vehicle-treated detached retina showed infiltration of CD11b-positve macrophage/microglia in the retina and subretinal space (395.9±83.8 cells/mm$^2$; FIG. 11A-B). Eyes treated with Z-VAD demonstrated even greater infiltration of CD11b-positive cells in the retina (514.7±54.5 cells/mm$^2$) with clusters of these cells present in the ONL (FIG. 11A-B), indicating that necrotic cell death may promote inflammatory reaction. This infiltration of CD11b-positive cells was significantly suppressed with Z-VAD+Nec-1 treatment (262.9±44.6 cells/mm$^2$, P<0.01; FIG. 11A-B). In comparison, significantly fewer CD11-b cells infiltrated the retina and subretinal space of RIP-3−/− mice. Further, RIP-3−/− eyes treated with Z-VAD demonstrated even less infiltration of CD11-b positive cells in the retina and subretinal space.

Figure 11C:
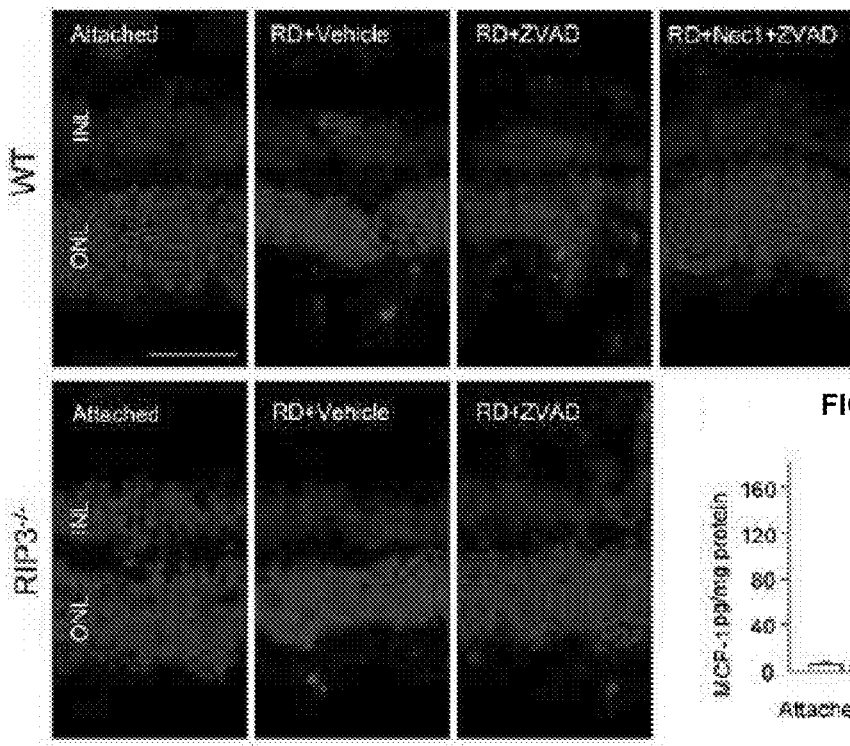
Figure 11D:
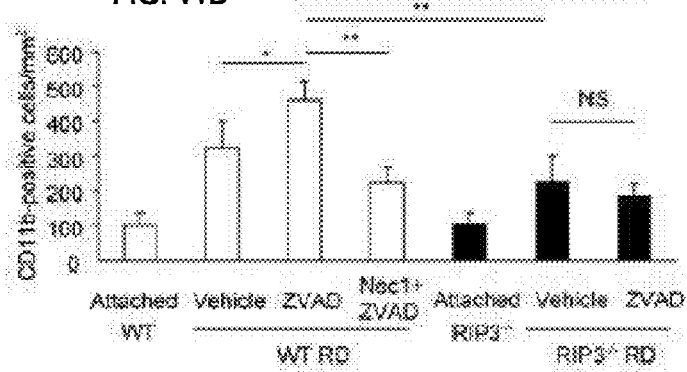

FIG. 11C-D show immunofluorescence for CD11b (FIG. 11C) and quantification of CD11b-positive macrophage/microglia (FIG. 11D) in WT and RIP-3−/− retina after retinal detachment. In WT mice, Z-VAD treatment significantly increased infiltration of CD11b-positive cells compared to vehicle treatment (P<0.05). This increase of CD11b-positive cells was significantly suppressed with Nec-1+Z-VAD treatment or RIP-3 deficiency (P<0.01; Scale bar, 50 µm).

Figure 11E:
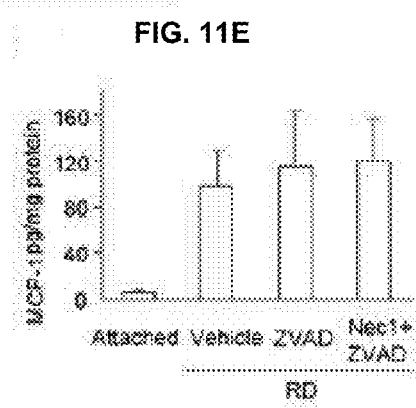
Figure 11F:
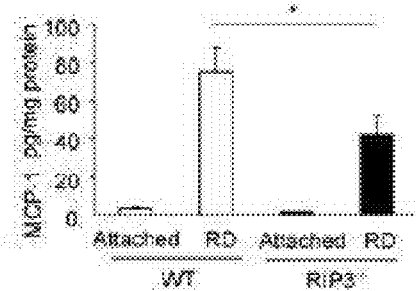
Figure 12A:
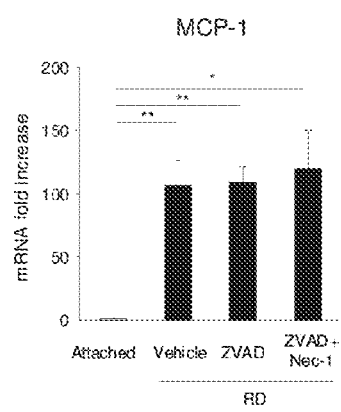
FIG. 12A-C are graphs showing quantitative real-time PCR analysis for MCP-1 (FIG. 12A), TNF-α (FIG. 12B), and Fas-L (FIG. 12C) in control retina without retinal detachment (n=9) and in retina three days after retinal detachment with treatment of vehicle (n=9), Z-VAD (n=8) or Z-VAD+Nec-1 (n=9). *, P<0.05; **, P<0.01.
Figure 12B:
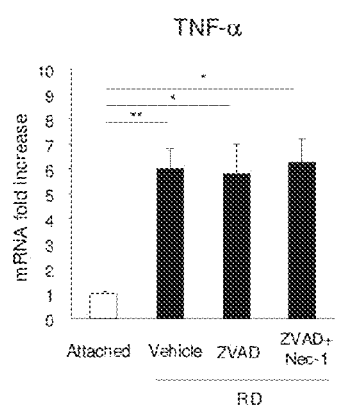

Although monocyte chemoattractant protein 1 (MCP-1) was previously described as an essential mediator of early infiltration of macrophage/microglia and the subsequent cell death after retinal detachment (Nakazawa T et al. (2007) PROC NATL ACAD SCI USA 104:2425-2430), Z-VAD+Nec-1 combination treatment did not affect MCP-1 expression (FIG. 12A and FIG. 13A). Further, FIG. 11E-F show an ELISA for MCP-1 on day three after retinal detachment in either WT or RIP-3−/− retinas (n=5 each; FIG. 11D) treated with vehicle (n=5), Z-VAD (n=5) or Nec-1+Z-VAD (n=6; FIG. 11C). Retinas without retinal detachment were used as controls. (*, P<0.05; **, P<0.01; NS, not significant). RIP-3−/− retinas also showed substantial upregulation of MCP-1 after retinal detachment, although its expression level was slightly decreased than that in WT retinas (FIG. 11F).

Cell death and inflammation communicate with each other during neurodegeneration (Zitvogel et al. (2010) CELL 141:798-804). Infiltrating inflammatory cells stimulate neuronal cell death (Nakazawa et al. (2007) PROC NATL ACAD SCI USA 104:2425-2430), and conversely dying cells, especially of the necrotic form, trigger inflammation (Cavassani et al. (2008) J EXP MED 205:2609-2621). We previously described that MCP-1 is a key mediator of early infiltration of macrophage/microglia after retinal detachment (Nakazawa et al. (2007) PROC NATL ACAD SCI USA 104:2425-2430). However, MCP-1 upregulation after retinal detachment was not substantially altered by Nec-1+Z-VAD combination treatment or by RIP-3 deficiency, suggesting that RIP kinases are not involved in the initiation of inflammation. The in situ hybridization data described herein indicate that RIP-3 is detected in the ONL after retinal detachment, suggesting that RIP kinase inhibition may target photoreceptors and suppress inflammation subsequent to photoreceptor death. However, since RIP-3 is known to be expressed in several cell types including macrophages (Newton et al. (2004) MOL CELL BIOL 24: 1464-9), and given the limited resolution of our in situ hybridization the possibility that RIP kinase inhibition may affect macrophage/microglia function cannot be excluded; defining the role of RIP kinases in cell death and inflammation warrants further studies using tissue-specific RIP-3−/− animals.

Example 6

RIP Kinases Mediate ROS Production and AIF Nuclear Translocation after Retinal Detachment The level of reactive oxygen species (ROS) production and apoptosis-inducing factor (AIF) nuclear translocation were measured after retinal detachment.

Immunohistochemistry (IHC) was performed as previously reported (Murakami Y et al. (2008) AM J PATHOL 173:1326-1338). Rabbit anti-AIF antibody (1:100; Cell Signaling Technology, Danvers, Mass.) was used as the primary antibody. The specimens were imaged by confocal microscopy using the Leica HCX APOL40X lens.

Immunofluorescence was performed as previously reported (Hisatomi et al. (2008) J CLIN INVEST 118:2025-2038. The enucleated eyes were frozen in OCT compound (Sakura Finetechnical Co., Tokyo, Japan). Five μm-thick sections were cut, air dried and fixed in cold acetone for 10 minutes. Rabbit anti-AIF antibody (1:100; Cell Signaling Technology, Danvers, Mass.) was used as the primary antibody and incubated at 4° C. overnight. A non-immune serum was used as a negative control. Alexa Fluor 488-conjugated goat anti-rabbit IgG was used as the secondary antibody and incubated at room temperature for one hour. The specimens were imaged by confocal microscopy using the Leica HCX APOL40X lens.

Figure 14A:
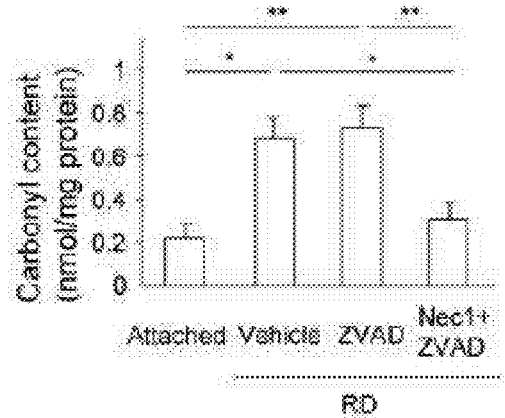
FIG. 14A-F are photographs and graphs showing RIP kinase inhibition prevents ROS production and AIF nuclear translocation after retinal detachment.
Figure 14B:
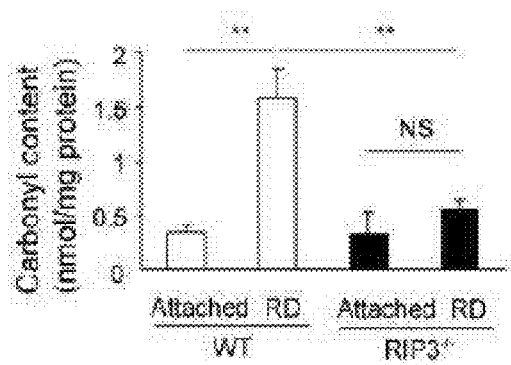
Figure 14C:
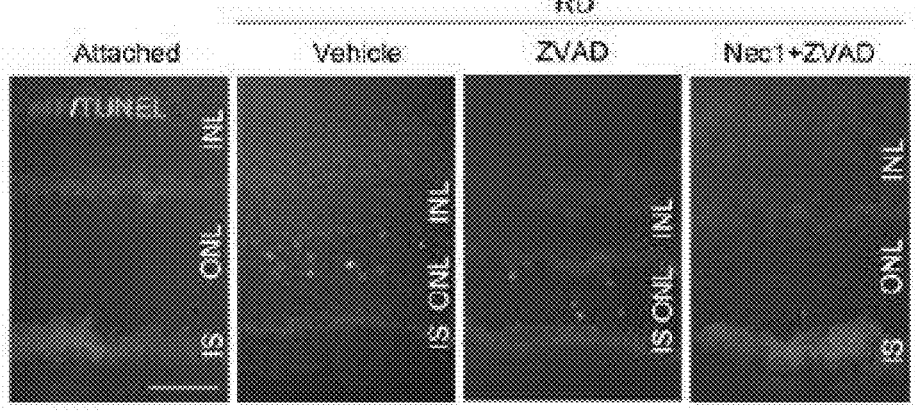
Figure 14D:
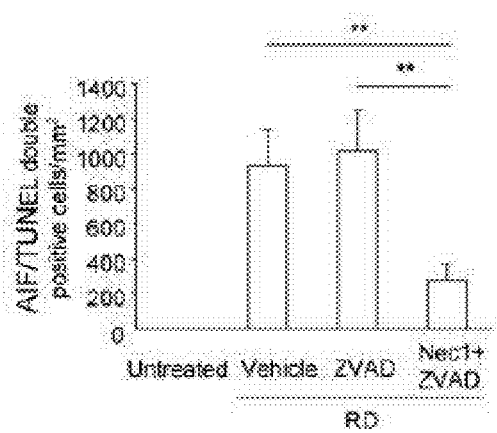

Recent studies reported that RIP kinases regulate downstream ROS production during programmed necrosis (Cho Y S et al. (2009) CELL 137:1112-1123; Zhang D W et al. (2009) SCIENCE 325:332-336; Kim et al. (2007) MOL CELL 26: 675-687). ELISA for carbonyl adducts of proteins was used to examine oxidative retinal damage following retinal detachment. Specifically, the amounts of protein carbonyls were determined by using OxiSelect™ Protein Carbonyl ELISA Kit (Cell Biolabs, San Diego, Calif.). As shown in FIG. 14A, the carbonyl contents in control retina without retinal detachment (n=6-8) and in retina three days after retinal detachment with treatment of vehicle, Z-VAD or Z-VAD+Nec-1 (the Nec-1 compound was a compound of Formula I-C; n=7 each) were detected by an ELISA in wild type (FIG. 14A) and in RIP-3−/− retina (n=10) (FIG. 14B). The results indicate that on day three after retinal detachment, the retina treated with vehicle or Z-VAD demonstrated significant increase of carbonyl contents per mg protein compared to untreated retina (P<0.05; FIG. 14A). In contrast, Z-VAD+Nec-1 treatment almost completely suppressed the increase of carbonyl contents after retinal detachment (P<0.05; FIG. 14A). RIP-3−/− retinas also showed significantly less carbonyl contents after retinal detachment compared to WT retinas (P<0.05; FIG. 14B).

Figure 14E:
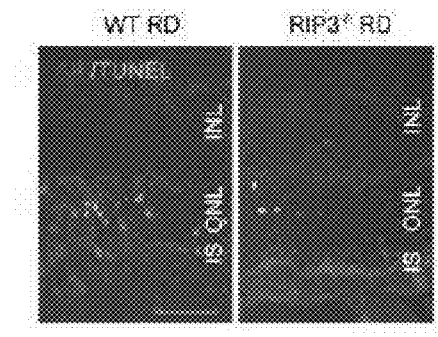
Figure 14F:
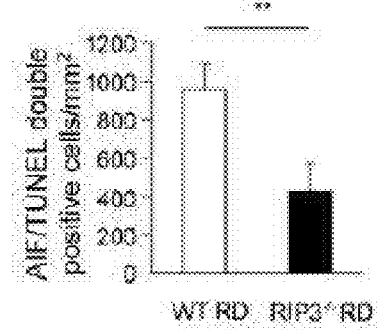

Apoptosis-inducing factor (AIF) is a caspase-independent inducer of cell death, which is released from the mitochondria and translocates into the nuclei during cell death (Susin S A et al. (1999) NATURE 397:441-446). The mitochondrial release of AIF is a critical event for the photoreceptor death after retinal detachment (Hisatomi T et al. (2001) AM. J. PATHOL. 158:1271-1278; Hisatomi T et al. (2008) J. CLIN. INVEST. 118:2025-2038). Because ROS overproduction is known to induce mitochondrial membrane permeabilization and AIF release (Krantic S et al. (2007) PROG. NEUROBIOL. 81:179-196), the cellular localization of AIF was examined by IHC and immunofluorescence. The untreated retina showed positive staining for AIF in the inner segment of photoreceptors, which are a mitochondrion-rich region. FIG. 14C-F show double staining for AIF and TUNEL (14C and E) and quantification of AIF/TUNEL double positive photoreceptors (14D and F) in control retina or in WT and RIP-3−/− retinas (n=5 each; FIGS. 14E and F) treated with vehicle, Z-VAD or Nec-1+Z-VAD (the Nec-1 compound was a compound of Formula I-C; n=6 each) three days after retinal detachment (IS: inner segment. *, P<0.05; **, P<0.01; Scale bar, 50 μm). In vehicle- or Z-VAD-treated retina, AIF staining was observed in TUNEL-positive photoreceptor nuclei (AIF/TUNEL-double positive cells: 933.9±210.6 cells/mm$^2$ and 1021.9±233.9 cells/mm$^2$, respectively). In contrast, Z-VAD+Nec-1 treatment significantly reduced AIF nuclear translocation (281.3±93.5 cells/mm$^2$, P<0.01; FIG. 7B-C). The data demonstrate that AIF translocation into TUNEL-positive photoreceptor nuclei was increased after retinal detachment; whereas Nec-1+Z-VAD combination treatment or RIP-3 deficiency substantially reduced AIF nuclear translocation. These data also demonstrate that ROS production and AIF nuclear translocation are downstream events of RIP signaling.

In addition, overproduction of ROS has been implicated in mitochondrial dysfunction and programmed necrosis (Vercammen D et al. (1998) J. EXP. MED. 188:919-930; Lin Y et al. (2004) J. BIOL. CHEM. 279:10822-10828). NADPH oxidase 1 has been shown to form a complex with RIP-1 and generate superoxide during programmed necrosis of L929 and MEF cells (Kim Y S et al. (2007) MOL. CELL 26: 675-687). Alternatively, RIP-3 activates metabolic enzymes such as glutamate dehydrogenase 1, and thereby increases mitochondrial ROS production in NIH3T3 cells (Zhang et al. (2009) SCIENCE 325:332-336). Although there might be several molecular pathways and cell sources for ROS production in vivo, the results disclosed herein indicate that RIP-1 kinase mediates, at least in part, the ROS generation after retinal detachment, and the mitochondrial release of AIF, a key effector of caspase-independent apoptosis and programmed necrosis (Susin S A et al. (2000) EXP. MED. 192:571-580; Moubarak R S et al. (2007) MOL. CELL BIOL. 27:4844-4862). Further, the results disclosed herein demonstrate that ROS production after retinal detachment was suppressed by RIP kinase inhibition, i.e., inhibition of RIP-1 kinase by Nec-1 efficiently prevents ROS production, AIF nuclear translocation, and necrotic photoreceptor death after retinal detachments. In addition, RIP kinases act upstream of AIF nuclear translocation. Recent studies also demonstrate that AIF is an essential mediator of programmed necrosis induced by alkylating DNA damage (Moubarak et al. (2007) MOL CELL BIOL 24: 4844-4862). These results suggest that RIP kinases, AIF translocation, and programmed necrosis are linked.

Figure 16:
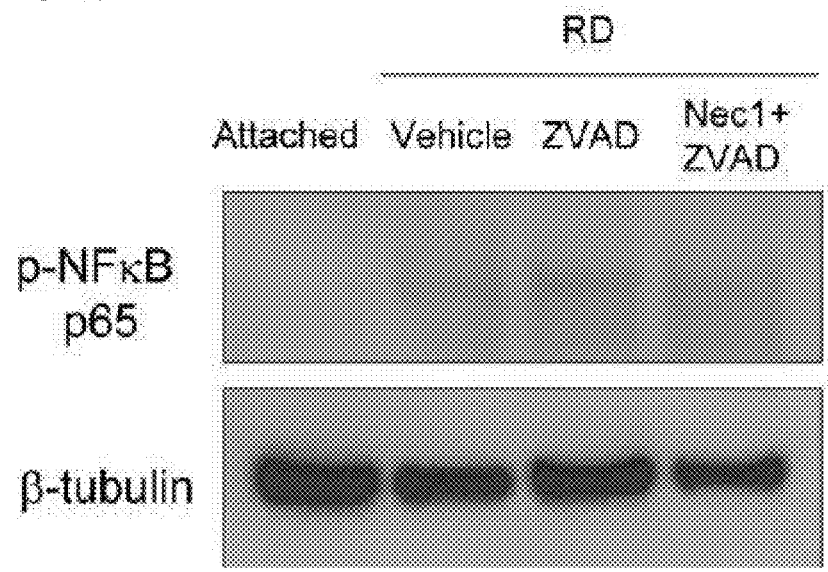
FIG. 16 is a photograph of an immunoblot from a Western blot analysis for phospho-NFκB p65 in control retina without a retinal detachment and in retina three days after retinal detachment with treatment of vehicle, Z-VAD or Z-VAD+Nec-1 (lane-loading differences were normalized by the level of β-tubulin).

The data suggests that RIP-1 is an adaptor kinase that acts downstream of death domain receptors and is essential for both cell survival and death (Vandenabeele et al. (2010) SCI SIGNAL 3: re4). The intermediate domain of RIP-1 mediates activation of the prosurvival transcriptional factor NF-κB through polyubiquitination of RIP-1 (Li H et al. (2006) J. BIOL. CHEM. 281:13636-13643), and RIP-1 knockout mice die soon after birth with reduced NF-κB activation and massive necrosis of lymphoid and adipose tissue (Kelliher M A et al. (1998) IMIVIUNITY 8:297-303). On the other hand, the N-terminal kinase functions of RIP-1 is crucial for programmed necrosis but dispensable for prosurvival of NF-κB activation (Holler N et al. (2000) NAT. IMMUNOL. 1:489-495; Degterev A et al. (2008) NAT. CHEM. BIOL. 4:313-321; Lee T H et al. (2004) J. BIOL. CHEM. 279:33185-33191). Consistent with these results, Nec-1 showed no effect on NF-κB p65 phosphorylation after retinal detachment (FIG. 16). RIP-1 switches function to a regulator of cell death when it is unubiquitinated and forms a death-signaling complex (Mahoney et al. 2008 PROC. NATL. ACAD. SCI. USA 105:11778-11783; Wang et al. (2008) CELL 133:693-703). In addition, recent studies revealed that formation of RIP-1-RIP-3 complex is a critical step in the RIP-1 kinase activation and induction of programmed necrosis (He et al. (2009) CELL 137:1100-1111; Cho et al. (2009) CELL 137:1112-1123; Zhang et al. (2009) SCIENCE 325:332-336). Further, He et al. showed that RIP-1 was expressed at similar levels in fourteen cell lines undergoing cell death, while RIP-3 expression levels correlated with the cellular necrotic response (He et al. (2009) CELL 137:1100-1111). After retinal detachment, RIP-3 expression increased over 10-fold and RIP-3 deficiency prevented the shift to necrotic photoreceptor death by Z-VAD suggesting that RIP-3 is a key regulator of programmed necrosis after retinal detachment. Thus, the greater fold increase of RIP-3 compared to RIP-1 that was observed after retinal detachment may be a crucial step that directs the photoreceptors to programmed necrosis.

Example 7

Suppression of Macroautophagy Induction in the Retina after Retinal Detachment

The level of macroautophagy induction in the retina was measured following retinal detachment. Cell death with autophagy is another form of cell death that is morphologically defined by the lack of chromatin condensation and accumulation of autophagic vacuoles (Kroemer G et al. (2009) CELL DEATH DIFFER. 16:3-11), and these morphological signs have been described in several neurodegenerative diseases (Kourtis N & Tavernarakis N (2009) CELL DEATH DIFFER. 16:21-30). Degterev et al. also reported that macroautophagy was activated during programmed necrosis (2005 NAT. CHEM. BIOL. 1:112-119).

The morphological change of photoreceptors after retinal detachment was analyzed by TEM, but photoreceptors associated with autophagic vacuoles were not apparent in each group.

For Western Blot analysis, the vitreous and neural retina combined, were collected at three days after retinal detachment. Samples were run on 4-12% SDS-polyacrylamide gel electrophoresis and transferred onto PVDF membrane. After blocking with 3% nonfat dried milk, the membrane was reacted with anti-light chain 3 antibody (1:1000; Cell signaling), anti-phosphorylated ribosomal protein S6 antibody (1:1000; Cell Signaling) or anti-phosphorylated NF-κB p65 antibody (1:1000; Cell Signaling). Immunoblots were then developed with enhanced chemiluminescence. Lane-loading differences were normalized by β-tubulin (1:1000; Cell Signaling).

Figure 17A:
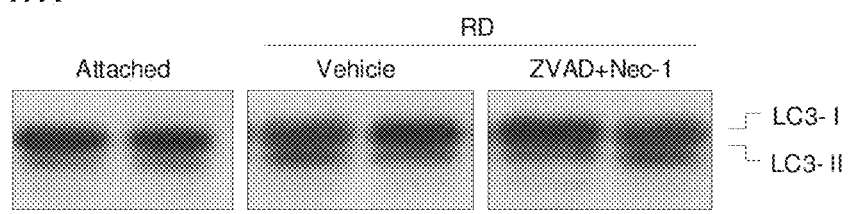
FIG. 17A-B are photographs of immunoblots from a (FIG. 17A) Western blot analysis for light chain 3 in control retina without retinal detachment and in retina three days after retinal detachment with treatment of vehicle or Z-VAD+Nec1 and a (FIG. 17B) Western blot analysis of phosphorylated ribosomal protein S6 in control retina without retinal detachment and in retina 3 days after retinal detachment.
Figure 17B:
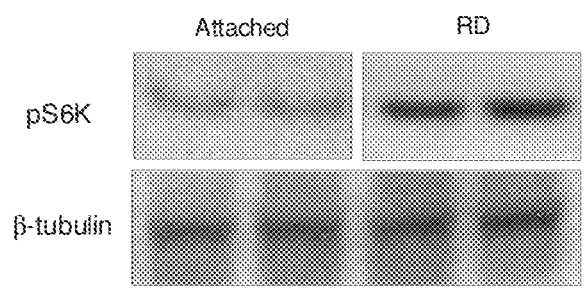

Western blot analysis of the lipidated form of light chain 3, a well-known marker of macroautophagy, demonstrated no significant difference in its expression after retinal detachment (FIG. 17A). Phosphorylated ribosomal protein S6, reflecting activity of ribosomal S6 kinase 1, an inhibitor of macroautophagy, was substantially upregulated in the retina after retinal detachment (FIG. 17B). These data indicate that macroautophagy induction may be suppressed in the retina after retinal detachment.

In addition, chaperone-mediated autophagy (CMA), another lysosomal degradation pathway, is known to be upregulated during starvation and oxidative stress (Dice J F (2007) AUTOPHAGY 3:295-299). Lysosomal-associated membrane protein type 2A (LAMP-2A), a lysosomal receptor involved in CMA, is a marker of CMA. Starvation increases LAMP-2A by preventing its degradation while oxidative stress results in transcriptional upregulation of LAMP-2A. However, LAMP-2A expression levels were unchanged in the retina after retinal detachment, although its localization in lysosomal membrane that directly correlates with CMA activity remains to be addressed in further studies (Cuervo A M & Dice J F (1996) SCIENCE 273:501-503).

Example 8

Z-VAD+Nec-1 Treatment was More Effective than TNF-α Blockage

Figure 12C:
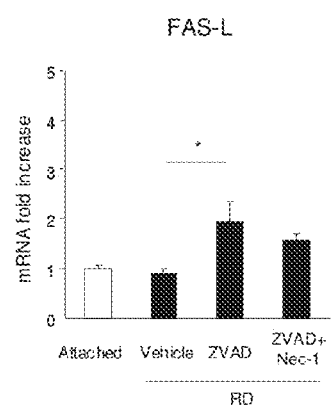

TNF-α and Fas-L are potent inducer of programmed necrosis as well as apoptosis (Degterev A (2005) NAT CHEM BIOL 1:112-119). The effectiveness of a TNF-α blockade after retinal detachment was measured. In particular, the role of TNF-α, one of the main stimuli responsible for the initiation of programmed necrosis of photoreceptors after retinal detachment, was investigated in part because TNF-α was increased in detached retina (FIGS. 18A and 18B) and treatment with a neutralizing anti-TNF-α antibody suppressed photoreceptor loss (FIG. 18C-D). However, other factors may also contribute to photoreceptor death, as the effect of TNF-α blockade was not as effective as that of Nec-1+Z-VAD treatment. Further, Fas ligand expression increased in Z-VAD-treated retina after retinal detachment compared to vehicle treatment (FIG. 12C), and may play a role in promoting necrotic photoreceptor death in Z-VAD-treated eyes.

TNF-α protein contents in rat retina were determined using ELISA Kit for rat TNF-α (Invitrogen, Carlsbad, Calif.). Goat anti-mouse/rat TNF-α blocking antibody was purchased from R&D Systems (Minneapolis, Minn.). The rat eyes were subretinally injected with 1% of sodium hyaluronate containing 0.1 mg/ml of anti-TNF-α antibody or control antibody.

The results indicate that TNF-blockade was not as effective as treatment with Z-VAD in combination with Nec-1. After retinal detachment, TNF-α was increased in detached retina (FIGS. 18A and 18B) and treatment with a neutralizing anti-TNF-α antibody suppressed photoreceptor loss (FIG. 18C), suggesting that TNF-α may contribute to the induction of apoptosis and programmed necrosis. In addition to TNF-α, Fas-L/Fas pathway is known to be activated and mediate photoreceptor death after retinal detachment (Zacks et al. (2004) INVEST OPHTHALMOL VIS SCI 45: 4563-4569; Zacks et al. (2007) ARCH OPTHALMOL 125:1389-1395), and may cooperate with TNF-α to activate RIP kinase and promote programmed necrosis in addition to apoptosis. (FIG. 19). As shown in FIG. 19, RIP-1 mediates prosurvival NF-κB activation through polyubiquitination of RIP-1 in response to TNF-α. When RIP-1 is unubiquitinated, RIP-1 switches function to a regulator of cell death. RIP-1 forms a death signaling complex with Fas-associated death domain (FADD) and caspase-8 after stimulation of death domain receptors, and induces caspase-dependent apoptosis. In conditions where caspase pathway is blocked, RIP-1 kinase is activated in RIP-1-RIP-3 complex and promotes programmed necrosis. TRAF2: tumor necrosis factor-receptor associated signaling adaptor. TRADD: TNF receptor—associated death domain. cIAP: cellular inhibitor of apoptosis. CYLD: cylindromatosis. Thus, RIP Kinases act as common intermediaries for various upstream death signals and their blockade in addition to caspases is likely necessary for effective neuroprotection.

Example 9

Figure 20A:
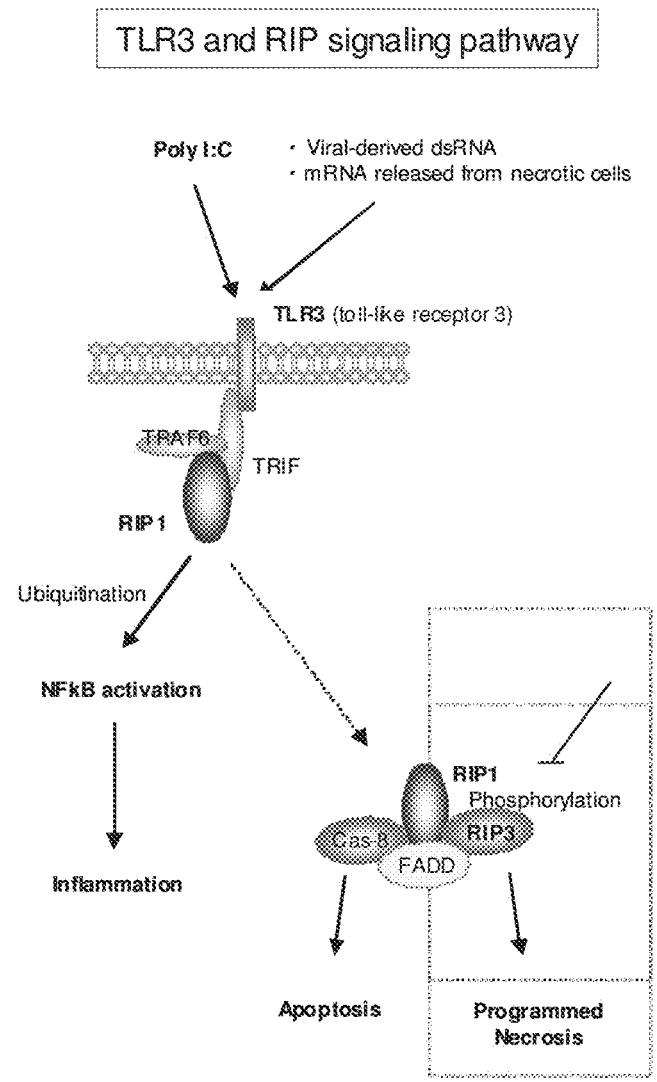
FIG. 20A is a schematic representation of the TLR3 and RIP signaling pathway.
Figure 20B:
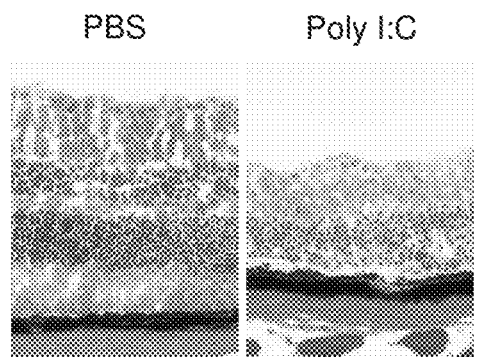
FIG. 20B is a photograph showing significant loss of photoreceptors and RPE in the ONL following poly I:C treatment.

Efficacy of a Necrosis Inhibitor and a Pan-Caspase Inhibitor in the Treatment of AMD A. Increased Expression of RIP-3 and RIP-1 in a Poly I:C Induced AMD Model In this example, the mechanism of photoreceptor cell death in dry AMD was investigated using a polyinosinic:polycytidylic acid (Poly I:C)-induced dry AMD model (Yang et al. (2009) NEJM 359(14):1456-63). Poly I:C is a synthetic double-stranded RNA (dsRNA) analog that activates toll-like receptor 3 (TLR3) signaling (FIG. 20A). Furthermore, dsRNA are known to exist in the drusen of human AMD patients. As depicted in FIG. 20A, activation of the TLR3 signaling results in activation of RIP-1 kinase pathway. FIG. 20B also shows that intraocular injection of poly I:C in mice caused significant geographic loss of photoreceptors and RPE thus mimicking human dry AMD (compare to PBS treated mice). In the experiments described herein, 2-3 µl of Poly I:C (1 mg/ml) was injected into the subretinal space of the eye (e.g., approximately 2-3 µg of Poly I:C was administered to the eye) to induce AMD.

Pathways leading to photoreceptor death in AMD were investigated. In particular, the expression levels of RIP-1 and RIP-3 proteins were measured in the Poly I:C-induced dry AMD model. RIP-3 is a key regulator of RIP-1 kinase activation (Galluzzi L et al. (2009) J. MOL. CELL BIOL.) and its expression level has been shown to correlate with responsiveness to programmed necrosis (He et al. (2009) CELL 137:1100-1111). As described below, it was demonstrated that necrotic photoreceptor death occurs in dry AMD.

Total RNA extraction and reverse transcription were performed as previously reported (Nakazawa T et al. (2006) MOL. VIS. 12:867-878) (Hisatomi T et al. (2008). J. CLIN. INVEST. 118:2025-2038). A real-time PCR assay was performed with Prism 7700 Sequence Detection System (Applied Biosystems, Foster City, Calif.). TaqMan Gene Expression assays were used to check the expression of RIP-1 (Rn01757378_m1) and RIP-3 (Rn00595154_m1). For relative comparison of each gene, the Ct value of real-time PCR data was analyzed with the ΔΔCt method and normalized by an endogenous control (18S ribosomal RNA).

Figure 21A:
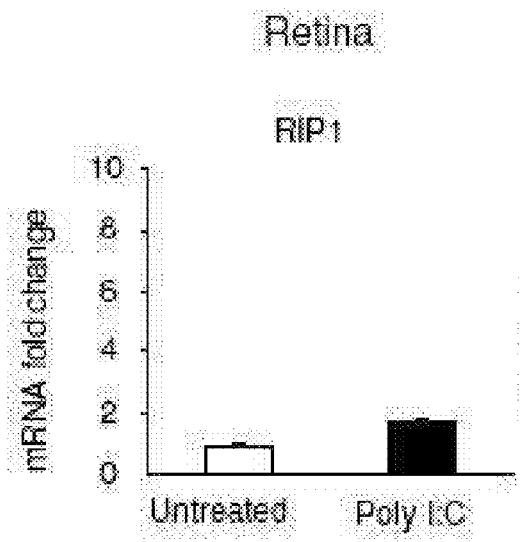
FIG. 21A-D are graphs showing RIP-1 (FIG. 21A) and RIP-3 (FIG. 21B) expression in the retina, as well as RIP-3 expression in the RPE cells (FIG. 21C) and macrophages (FIG. 21D), following poly I:C treatment, as determined by quantitative real-time PCR analysis.
Figure 21B:
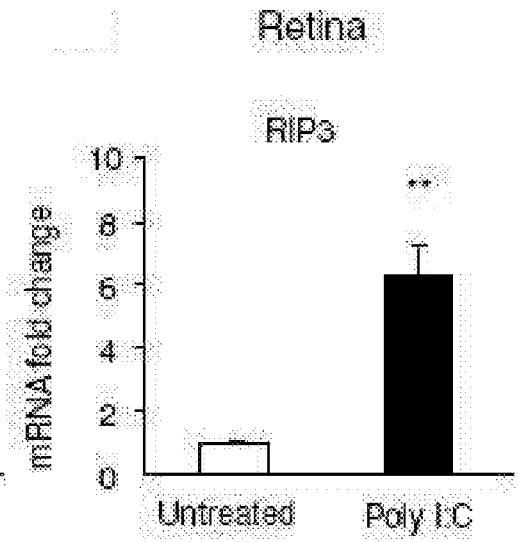
Figure 21C:
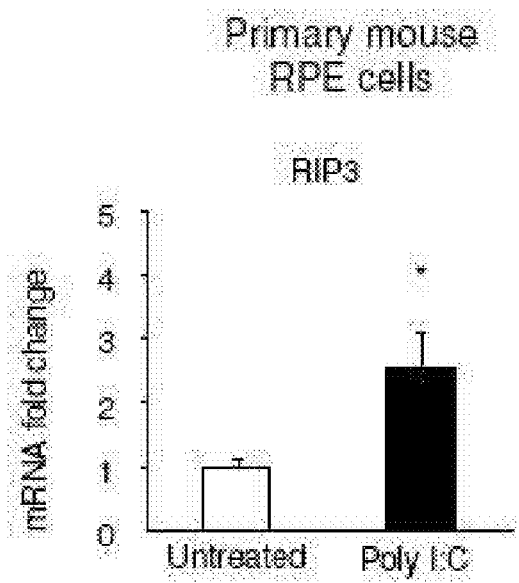
Figure 21D:
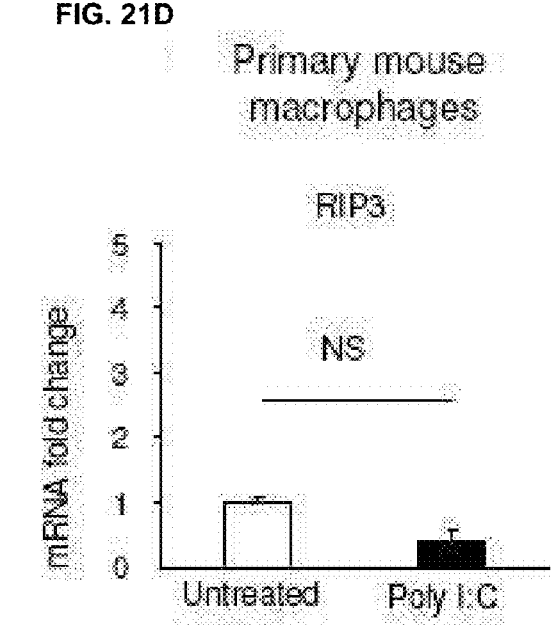

The expression levels of RIP-3 and RIP-1 mRNA were assessed in the retina by quantitative real-time PCR. FIG. 21A-B provide graphs showing the quantitative real-time PCR analysis for RIP-1 (FIG. 21A) and RIP-3 (FIG. 21B) in control retina (untreated) and in the retina of mice treated with poly I:C. RIP-1 expression increased approximately two-fold in the retina of mice treated with poly I:C compared to that in untreated retina (FIG. 21A). RIP-3 expression increased approximately 6-fold in poly I:C treated mice compared to control (FIG. 21B). The expression levels of RIP-3 in RPE cells and macrophages were also examined. As depicted in FIG. 21C, RIP-3 expression increased approximately three-fold in the RPE cells of mice treated with poly I:C compared to that in untreated RPE cells. In comparison, no significant difference in RIP-3 expression was observed in macrophage cells in mice treated with poly I:C compared to controls (FIG. 21D).

These data suggest that RIP-mediated programmed necrosis is involved in photoreceptor loss in dry AMD.

B. RIP-3 Deficiency Prevents Poly I:C-Induced Retinal Degeneration

Figure 22A:
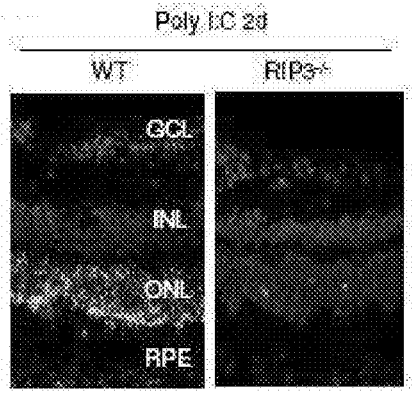
FIG. 22A-D are photographs and graphs showing quantification of TUNEL-positive photoreceptors (FIG. 22A and FIG. 22B) and ONL thickness (FIG. 22C and FIG. 22D) in RIP-3−/− mice two days after treatment with poly I:C.
Figure 22B:
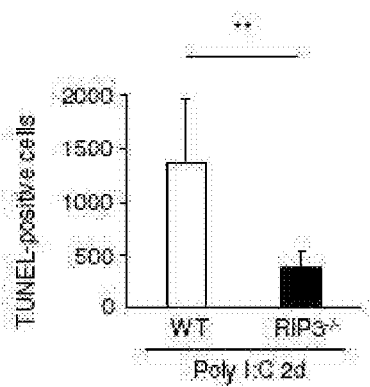

The role of RIP-3 in RIP-mediated programmed necrosis in photoreceptor loss in AMD was investigated using RIP-3−/− mice. TUNEL assays were used to measure the amount of apoptotic and necrotic cell death (Grasl-Kraupp et al., HEPTALOGY (1995) 21(5):1465-8). TUNEL and quantification of TUNEL positive cells in the ONL were performed as previously described (See Example 2). The thickness of the ONL was determined by the National Institutes of Health ImageJ software. FIG. 22A shows TUNEL (green) and DAPI (blue) staining in retina from wild type or RIP-3−/− mice treated with poly I:C. Two days after poly I:C treatment, RIP-3−/− mice showed significantly less TUNEL-positive cells than WT mice. Specifically, the number of TUNEL-positive cells in the RIP-3−/− mice treated with poly I:C was at least three fold less than control mice consistent with RIP-3 playing a role in mediating programmed necrosis in AMD (FIG. 22B).

Figure 22C:
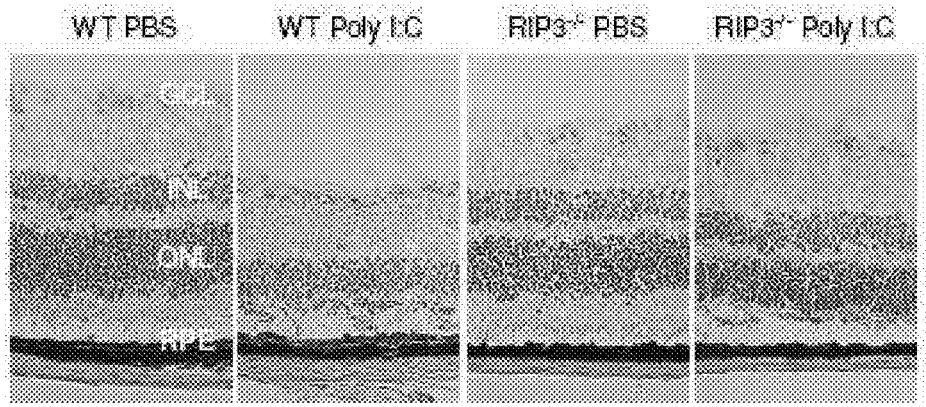
Figure 22D:
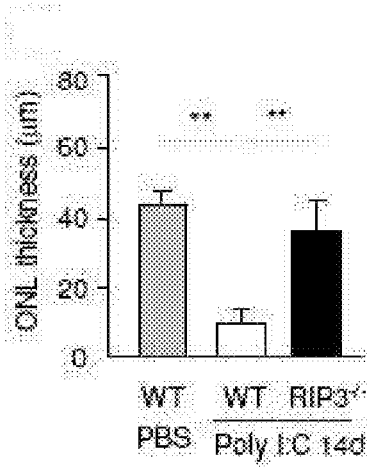

The thickness of the outer nuclear layer (ONL) was also determined in WT or RIP-3−/− mice at 14 days following treatment with poly I:C. Sections were randomly selected from either WT or RIP-3−/− mice following poly I:C treatment and the retina was photographed. The ONL thickness was measured in each section by masked observers. FIG. 22C-D show that ONL thickness was significantly reduced in WT retina treated with poly I:C. In comparison, ONL thickness was not affected in RIP-3−/− retina treated with poly I:C indicating that RIP-3 deficiency had a protective effect in photoreceptor loss in AMD.

Photoreceptors in WT or RIP-3−/− mice following poly I:C treatment were also examined by PI staining. In vivo PI staining was performed by injecting 5 μl of PI (50 μg/ml) into the subretinal space at two days after poly I:C treatment. After two hours, the eyes were enucleated and 10 μm thick cryosections were cut, air-dried, and fixed in 100% ethanol. DAPI was used to counterstain the nuclei. The center of the retina was photographed by fluorescence microscope, and the number of PI-positive cells in ONL was analyzed by ImageJ software.

Figure 23A:
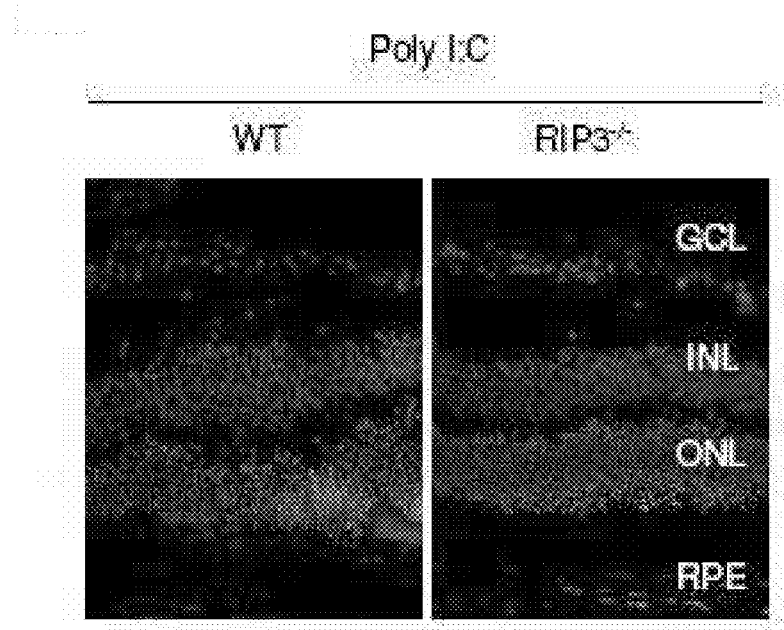
FIG. 23A-B are photographs of PI staining and graph showing quantification of PI-positive photoreceptors in RIP-3−/− mice two days after treatment with poly I:C.
Figure 23B:
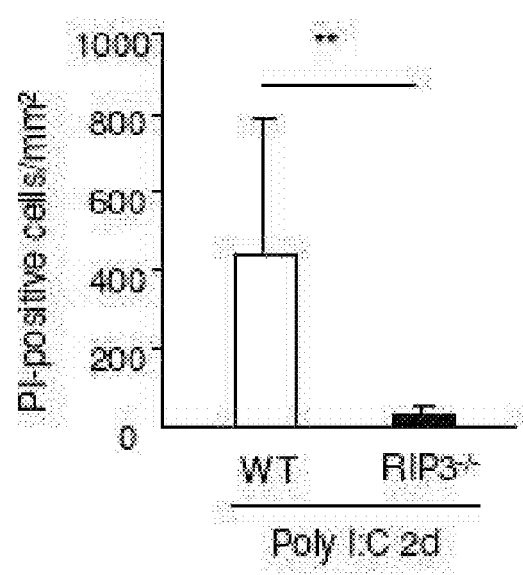

FIG. 23A-B show PI staining (FIG. 23A) and quantification of PI-positive photoreceptors (FIG. 23B) on day two after treatment with vehicle or poly I:C in wildtype or RIP-3−/− mice. Subretinal injection of PI prior to enucleation, a technique to demonstrate cells with disrupted cell membrane, showed decreased number of PI-positive photoreceptors in RIP-3−/− mice compared to wildtype mice. These findings are consistent with the TUNEL and ONL thickness studies, and indicate a involvement of RIP-mediated programmed necrosis in dry AMD.

C. Necrosis Inhibitor Prevents Poly I:C-Induced Retinal Degeneration in Combination with a Caspase Inhibitor Necrostatin-1 is a potent and selective inhibitor of programmed necrosis, which targets RIP-1 kinase activity (Degterev A et al. (2008) NAT. CHEM. BIOL. 4:313-321). The effectiveness of a RIP-1 kinase inhibitor in combination with a caspase inhibitor in the treatment of dry AMD was investigated.

Figure 24A:
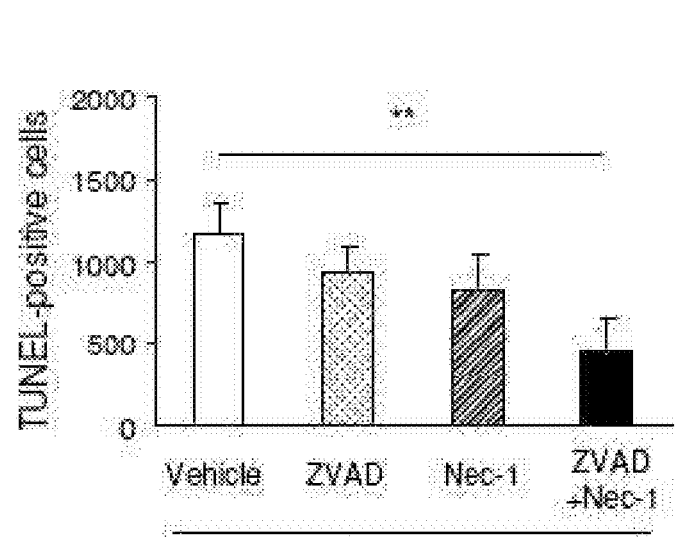
FIG. 24A-B are graphs showing quantification of TUNEL-positive photoreceptors (FIG. 24A) and ONL thickness (FIG. 24B) in mice treated with poly I:C.
Figure 24B:
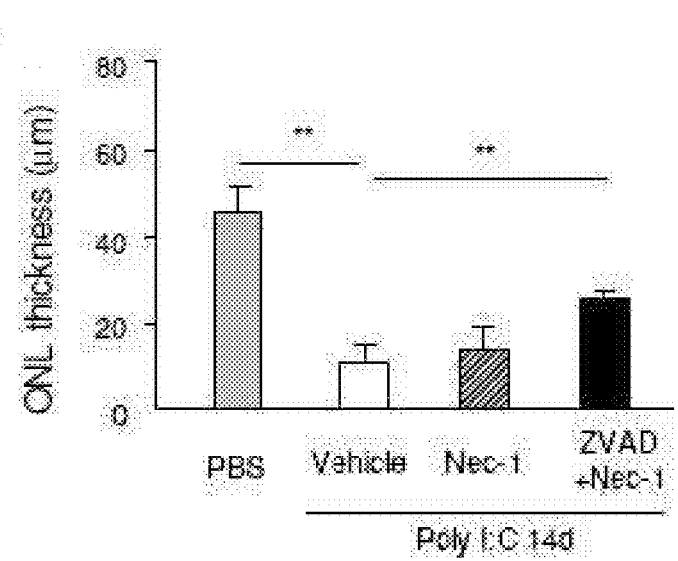

To determine the effect of Nec-1 and a pan-caspase inhibitor in the treatment of AMD, TUNEL assay was performed to assess photoreceptor cell death in the poly I:C induced AMD model. FIG. 24A shows that treatment with Z-VAD or Nec-1 alone had a slight effect on the number of TUNEL-positive cells in ONL as compared with vehicle treatment. In contrast, combined treatment with Nec-1+Z-VAD significantly reduced the number of TUNEL-positive cells in ONL. The thickness of ONL was also measured. As shown in FIG. 24B, the combination of Nec-1+Z-VAD significantly prevented the reduction in ONL thickness, whereas either Z-VAD or Nec-1 alone had minimal effect in preserving retinal thickness.

Collectively, these results indicate that programmed necrosis as well as apoptosis is involved in photoreceptor death in AMD, and that RIP-mediated programmed necrosis becomes a predominant form of photoreceptor death when caspase-dependent apoptotic pathway is inhibited.

Figure 25A:
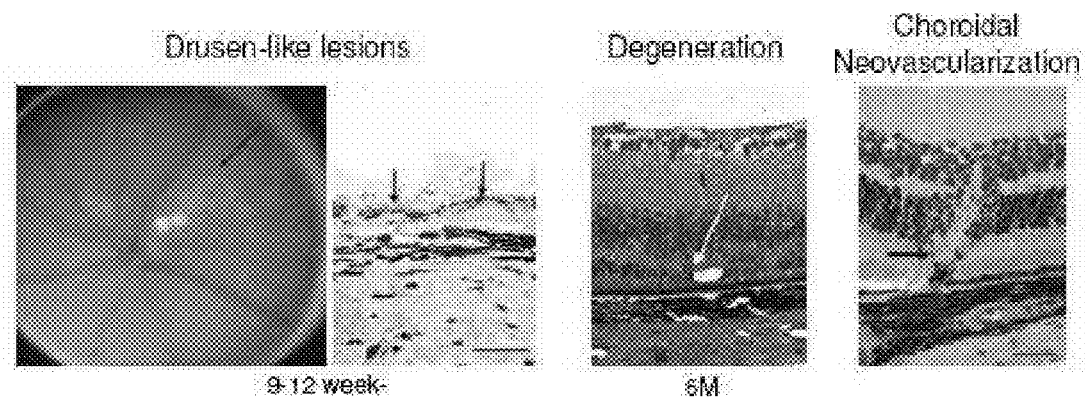
FIG. 25A are photographs showing the development of drusen-like lesions, retinal degeneration and choroidal neovascularization in CX3CR1−/−CCL2−/− double knockout mice.

D. Increased RIP-1 and RIP-3 Expression in the CX3CR1−/−CCL2−/− Mouse Model of AMD CX3CR1−/−CCL2−/− double knockout mice is a well-established model for dry and wet AMD (Tuo et al. IOVS (2007) 48(8): 3827-3836). At 9-12 weeks of age, these mice spontaneously develop drusen-like lesions characterized by heterogeneous, round or domed-shaped, soft-bordered, yellowish deposits within the subretina (FIG. 25A), which are associated with dry AMD. By 6 months of age, choroidal neovascularization, a hallmark of wet AMD, was observed in the eye of the CX3CR1−/−CCL2−/− double knockout mice (FIG. 25A).

Figure 25B:
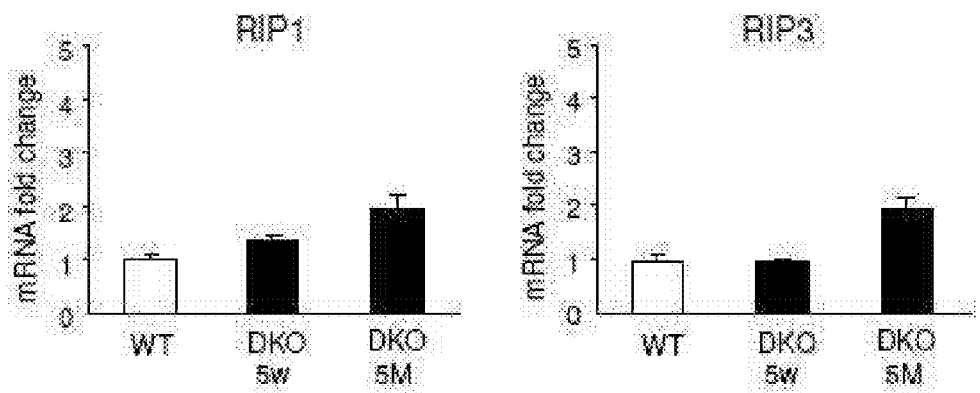

The expression levels of RIP-1 and RIP-3 mRNA were assessed in the retina of CX3CR1−/−CCL2−/− double knockout mice at 5 weeks (5w) and at 5 months (5M) of age. As shown in FIG. 25B, RIP-1 expression was elevated in the CX3CR1−/−CCL2−/− double knockout mice compared to WT mice. Further, RIP-1 expression progressively increased with age. Similarly, RIP-3 expression was also elevated in CX3CR1−/−CCL2−/− double knockout mice compared to WT mice. In addition, RIP-3 expression also increased with age (FIG. 25C). These results are consistent with results from the poly I:C-induced AMD model indicating that RIP-mediated programmed necrosis is involved photoreceptor death in AMD.

Together, the data from both the poly I:C induced and CX3CR1−/−CCL2−/− double knockout AMD models indicate that RIP-3 mediates necrotic photoreceptor death in AMD. To further confirm the role of RIP-3 mediated necrosis in AMD, CX3CR1/CCL2/RIP-3 triple knockout mice were generated. As described previously, CX3CR1−/−CCL2−/− double knockout mice spontaneously develop drusen-like lesions within the subretina by 9-12 weeks of age. In comparison, CX3CR1−/−CCL2−/−RIP-3−/− mice exhibited a significant reduction in the number of drusen-like lesions within the subretina (FIG. 26).

Collectively, these data indicate that suppression of RIP-3 gene expression significantly reduces the clinical features of AMD. These data further indicate that blockade of the RIP kinase pathway is important and necessary in addition to blockade of the caspase pathway for effective protection of photoreceptor cells in AMD.

E. RIP-3 Deficiency Reduces Inflammatory Cytokine Expression in the CX3CR1−/−CCL2−/− Mouse Model of AMD The expression levels of various inflammatory cytokines were assessed in the retina of CX3CR1−/−CCL2−/− double knockout mice at 2 months (2M) of age. As shown in FIG. 27, the expression of certain inflammatory cytokines such as TNF-α, CCL3 (MIP1-alpha), CCL5 (RANTES), and IL-6 were increased in the CX3CR1−/−CCL2−/− double knockout mice compared to WT mice. In comparison, RIP-3 deficiency in the context of the CX3CR1−/−CCL2−/−RIP-3−/− mice reduced the expression of these inflammatory cytokines. This data indicates that RIP-3 is involved in the inflammatory response associated with AMD. This data further suggests that inhibition of RIP-3 may provide effective protection against secondary inflammation associated with AMD.

Example 10

Efficacy of a Necrosis Inhibitor and a Pan-Caspase Inhibitor in the Treatment of Retinitis Pigmentosa Retinal degeneration 10 (rd10) mice are a model of autosomal recessive retinitis pigmentosa (RP), identified by Chang et al. in 2002 (Vision Res. 42:517-525). These mice carry a spontaneous mutation of the rod-phosphodiesterase (PDE) gene, leading to a rod degeneration that starts around post-natal day 18 (P18) and photoreceptor death which peaks at P25 (FIG. 28).

A. Increased Expression of RIP-3 and RIP-1 in rd10 Mice

To investigate the role of RIP-mediated programmed necrosis in RP, the expression levels of RIP-1 and RIP-3 mRNA were assessed in rd10 mice. As shown in FIG. 29A, RIP-1 expression was significantly elevated in rd10 mice compared to wild type mice and peaked at P28. The slight drop in RIP-1 expression by P35 was most likely due to significant death of photoreceptor cells by that time. RIP-3 expression was also elevated in rd10 mice when compared to control and its expression also peaked at P28 (FIG. 29B). These data suggest that RIP-mediated programmed necrosis is involved in photoreceptor loss in RP.

B. Simultaneous Inhibition of RIP Kinases and Caspases Prevented Photoreceptor Cell Death in rd10 Mice To determine the effect of Nec-1 and a pan-caspase inhibitor in the treatment of RP, ONL thickness was measured to assess photoreceptor cell death in rd10 mice. Mice were injected with Nec-1 (50 μs/g/day) and Z-VAD (10 μs/g/day). At postnatal day 25 (P25) through P28, mice received daily intraperitoneal injections. As shown in FIG. 30A-B, the combination of Nec-1+Z-VAD significantly prevented the reduction in ONL thickness in rd10 mice compared to vehicle treated mice, indicating that RIP-mediated necrosis as well as apoptosis are involved in photoreceptor cell death in RP.

C. RIP-3 Deficiency Inhibits Induction of Programmed Necrosis and Prevents Photoreceptor Death in RP.

The role of RIP-3 in RIP-mediated programmed necrosis in photoreceptor death in RP was investigated in RIP-3 knockout mice. ONL thickness was measured at postnatal day 28 (P28) to assess photoreceptor cell death in rd10 RIP-3 double mutant mice. As shown in FIG. 31A-B, RIP-3 deficiency significantly prevented the reduction in ONL thickness in rd10 mice consistent with RIP-3 playing a role in mediating programmed necrosis in RP.

Collectively, these data indicate that programmed necrosis and apoptosis are involved in photoreceptor loss in RP, and that RIP-3 mediates necrotic photoreceptor death in this retinal disorder. Suppression of RIP-3 gene expression significantly limits necrotic photoreceptor death in RP via a similar pathway to Nec-1 treatment. These data further indicate that blockade of the RIP kinase pathway is important and necessary in addition to blockade of the caspase pathway for effective protection of photoreceptor cells in RP.

Example 11

Increased Expression of RIP-1 and RIP-3 in RPE Cells Following Poly I:C Treatment As described previously in Example 9, poly I:C is a dsRNA analog that activates TLR3 signaling and the RIP-1 kinase pathway. Further, intraocular injection of poly I:C in mice caused significant geographic loss of photoreceptors and RPE cells thus mimicking human dry AMD (FIG. 20B). In this Example, pathways leading to RPE cell death following poly I:C treatment were investigated.

Primary RPE cells were extracted from the retina of mice and cultured in the presence of 5 μg/ml of poly I:C for 48 hours or with PBS. Total RNA extraction and reverse transcription were performed as previously reported (Nakazawa T et al. (2006) MOL. VIS. 12:867-878) (Hisatomi T et al. (2008). J. CLIN. INVEST. 118:2025-2038). A real-time PCR assay was performed with Prism 7700 Sequence Detection System (Applied Biosystems, Foster City, Calif.). TaqMan Gene Expression assays were used to check the expression of RIP-1 (Rn01757378_m1) and RIP-3 (Rn00595154_m1). For relative comparison of each gene, the Ct value of real-time PCR data was analyzed with the ΔΔCt method and normalized by an endogenous control (18S ribosomal RNA).

The expression levels of RIP-1 and RIP-3 mRNA were assessed in primary RPE cells treated with poly I:C. FIG. 32A-B provide graphs showing the quantitative real-time PCR analysis for RIP-1 (FIG. 32A) and RIP-3 (FIG. 32B) in control RPE cells treated with PBS and in RPE cells after treatment with poly I:C. RIP-1 expression increased approximately two-fold in RPE cells treated with poly I:C compared to untreated RPE cells. RIP-3 expression in RPE cells also increased approximately three-fold after poly I:C treatment.

These data indicate that RIP-mediated programmed necrosis is involved in RPE cell loss following poly I:C treatment.

Example 12

Necrosis Inhibitor or RIP-3 Deficiency Prevents Poly I:C induced RPE Cell Death

In this Example, the effectiveness of a necrosis inhibitor (i.e., necrostatin-1) to prevent poly I:C induced RPE cell death was investigated.

As described in Example 11, primary RPE cells were extracted from the retina of mice and cultured in the presence of 5 μg/ml of poly I:C for 48 hours or with PBS. Cell viability was measured using Cell Counting Kit-8 (Dojindo Laboratories, Kumamoto, Japan). This assay is based on the cleavage of 2-(2-methoxy-4-nitrophenyl)-3-(4-nitrophenyl)-5-(2,4-disulfophenyl)-2H-tetrazolium, monosodium salt (WST-8) by the mitochondrial dehydrogenase enzyme to produce a formazan dye. After incubation with WST-8 for two hours at 37° C., absorbance was measured at 450 nm to determine cell viability.

FIG. 33A shows the viability of RPE cells treated with poly I:C in combination with Z-VAD or Nec-1+Z-VAD. Z-VAD or Nec-1 treatment alone did not protect RPE cells from poly I:C induced cell death. In comparison, Nec-1 combined with Z-VAD substantially restored cell viability and prevented poly I:C induced cell death. This data indicates that programmed necrosis as well as apoptosis are involved in poly I:C induced RPE cell death, and that the RIP-1 and RIP-3 mediated programmed necrosis becomes a predominant form of RPE cell death when the caspase-dependent pathway is inhibited.

The role of RIP-3 in RIP-mediated programmed necrosis in RPE cells was further investigated using poly I:C treated RIP-3−/− cells. FIG. 33B shows the viability of WT or RIP-3−/−RPE cells treated with poly I:C in combination with Z-VAD. Without poly I:C treatment, the viability of RPE cells was similar in WT and RIP-3−/− cells. Z-VAD treatment did not protect WT RPE cells from poly I:C induced cell death. In contrast, RIP-3−/− cells treated with both poly I:C and Z-VAD were protected from cell death.

Further, as described in Example 9, CX3CR1−/−CCL2−/−RIP-3−/− mice exhibited a significant reduction in the number of drusen-like lesions within the subretina when compared to CX3CR1−/−CCL2−/− mice (FIG. 26). Drusen is usually located between the RPE cells and their vascular supply, the choriocapillaris. The presence of drusen may therefore interfere with RPE function by depriving the RPE cells of oxygen and nutrients. Additionally, drusen formation is thought to signify RPE dysfunction (i.e., result as a function of diseased RPE). Our data that RIP-3 deficiency reduces drusen-like lesions in the context of CX3CR1−/−CCL2−/−RIP-3−/− mice provides further evidence that blockade of the RIP-3 kinase pathway may have a protective effect on RPE function.

Collectively, these results indicate that programmed necrosis as well as apoptosis are involved in poly I:C induced RPE cell death. Without wishing to be bound by theory, it is contemplated that blockage of the RIP kinase pathway in addition to blockage of the caspase pathway, is necessary for effective protection of RPE cell death.

Example 13

Efficacy of a Necrosis Inhibitor and/or an Apoptosis Inhibitor in the Treatment of Retinal Detachment in Human Subjects The efficacy of a necrosis inhibitor (e.g., necrostain-1 or necrostatin-4) and/or an apoptosis inhibitor (e.g., a pan-caspase inhibitor, e.g., IDN-6556) in the treatment of retinal detachment will be tested in human subjects.

Specifically, a necrostatin-1 or necrostatin-4 either alone or in combination with IDN-6556 will be administered during one of three standard surgical procedures for treating patients over the age of 18 with a macula-off retinal detachment. There are approximately 25,000 new patients diagnosed with macula-off retinal detachment each year in the United States, with the average age of these patients being in the 50s. The onset of the disease is fairly rapid, and patients usually present within a few days to the eye doctor with photopsias (light sensation), floaters and rapid vision loss. The only treatment option for macula-off retinal detachment is surgery, and currently there is no pharmacotherapy to prevent photoreceptor cell loss in these patients. The three types of surgical procedures used to treat macula-off retinal detachment are pneumatic retinopexy, scleral buckle and vitrectomy.

For those patients treated with pneumatic retinopexy, intravitral injections of the necrosis inhibitor (e.g., necrostatin-1 or necrostatin-4) either alone or in combination with the apoptosis inhibitor (e.g., IDN-6556) will be administered before the surgery (e.g., at the time of diagnosis or at least one day before the surgery), at one week post-surgery, and possibly at two weeks post-surgery. In some cases, the necrosis inhibitor either alone or in combination with an apoptosis inhibitor will also be administered at the time of surgery. It is contemplated that 15 mM of IDN-6556 and/or 20 mM of necrostain-1 or necrostatin-4 (in a total volume of 100 µL) can be administered to the patient to achieve a final concentration of 300 µM and 400 µM, respectively, in the eye (assuming that the average volume of an eye is approximately 5 mL).

For patients treated with scleral buckle, intravitral injections of the necrosis inhibitor (e.g., necrostatin-1 or necrostatin-4) either alone or in combination with the apoptosis inhibitor (e.g., IDN-6556) will be administered before the surgery (e.g., at the time of diagnosis or at least one day before the surgery), at the time of the surgery, at one week post-surgery, and possibly at two weeks post-surgery.

For patients treated with vitrectomy, intravitral injections of the necrosis inhibitor (e.g., necrostatin-1 or necrostatin-4) either alone or in combination with the apoptosis inhibitor (e.g., IDN-6556) will be administered before the surgery (e.g., at the time of diagnosis or at least one day before the surgery), at the time of the surgery, at one week post-surgery, and possibly at two-weeks post-surgery.

Patients who undergo surgical intervention only will serve as controls. The study endpoint measures the proportion of patients achieving 20/40 vision or better at three months after treatment. It is contemplated that a higher proportion of patients treated with a combination of a necrosis inhibitor (e.g., necrostatin-1 or necrostatin-4) and an apoptosis inhibitor (e.g., IDN-6556) in addition to surgery will achieve a 20/40 reading vision or better and/or will show an improvement in levels of visual acuity gain when compared to controls.

Example 14

Efficacy of a Necrosis Inhibitor and/or an Apoptosis Inhibitor in the Treatment of Neovascular AMD in Human Subjects The efficacy of a necrosis inhibitor (e.g., a necrostain-1 or necrostatin-4) and/or an apoptosis inhibitor (e.g., a pan-caspase inhibitor, e.g., Z-VAD or IDN-6556) in the treatment of AMD will be tested in human subjects.

Specifically, a necrostatin-1 or necrostatin-4 either alone or in combination with IDN-6556 will be administered in combination with anti-VEGF therapy for the treatment of patients over the age of 18 who are affected with wet AMD. It is contemplated that 15 mM of IDN-6556 and/or 20 mM of necrostain-1 or necrostatin-4 (in a total volume of 100 µL) can be administered to the patient to achieve a final concentration of 300 µM and 400 µM, respectively, in the eye (assuming that the average volume of an eye is approximately 5 mL). Alternatively, a slow release formulation of the necrosis inhibitor either alone or in combination with an apoptosis inhibitor may be administered.

For those patients treated anti-VEGF therapy, intravitral injections of the necrosis inhibitor (e.g., necrostatin-1 or necrostatin-4) either alone or in combination with the apoptosis inhibitor (e.g., IDN-6556) will be administered at the time of diagnosis, at one-month, three-months, six-months, and possibly twelve-months after the initial injection. Patients who receive anti-VEGF injections alone will serve as controls.

The study endpoint measures the proportion of patients achieving a 20/40 vision or better at six months and at twelve months after the first injection of necrostatin-1 or necrostatin-4 alone or in combination with IDN-6556. It is contemplated that a higher proportion of patients treated with a combination of a necrostatin-1 and IDN-6556 or a combination of necrostatin-4 and IDN-6556 in addition to anti-VEGF therapy will achieve a 20/40 reading vision or better and/or will show an improvement in levels of visual acuity gain when compared to controls.

Example 15

Efficacy of a Necrosis Inhibitor and/or an Apoptosis Inhibitor in the Treatment of Ocular Disorders in Human Subjects The efficacy of a necrosis inhibitor (e.g., a necrostain-1 or necrostatin-4) and/or an apoptosis inhibitor (e.g., a pan-caspase inhibitor, e.g., IDN-6556) as an adjunct to the treatment of the underlying ocular disorder will be tested in human subjects. The effectiveness of combination therapy can be measured in patients with an ocular disorder selected from retinitis pigmentosa, Stargardt's disease, retinopathies (e.g., inflammatory retinopathy, infectious retinopathy, and infectious retinopathy), dry AMD, myopic degeneration, diabetic retinopathy, macular edema, and central serous retinopathy. Specifically, a necrostatin-1 or necrostatin-4 either alone or in combination with Z-VAD or IDN-6556 will be administered for the treatment of patients affected with these ocular disorders.

For patients affected with retinitis pigmentosa, efficacy of treatment may be measured by determining whether there is an increase or preservation in the thickness of the macula as measured by optical coherence tomography (OCT); a preservation or an improvement of visual field (e.g., by at least 10% in the mean standard deviation on the Humphrey Visual Field Test; and/or an improvement or preservation of an electroretinograph (ERG), a measurement of the electrical response of the retina to light stimulation, (e.g., to increase ERG amplitude by at least 15%).

For patients affected with Stargardt's disease, efficacy of treatment may be measured by determining whether there is a preservation or an increase in the thickness of the macula as measured by OCT; and/or an improvement or preservation of a multifocal ERG.

For patients affected with Cone-Rod Dystrophy, efficacy of treatment may be measured by determining whether there is an increase in the thickness of the macula as measured by OCT; an improvement of an ERG, and/or preservation of a multifocal ERG.

For patients affected with dry AMD with geographic atrophy, efficacy of treatment may be evaluated by microperimetry and by measurement of fundus autofluorescence. Alternatively, visual acuity of these patients may be assessed.

INCORPORATION BY REFERENCE

The entire disclosure of each of the patent documents and scientific articles cited herein are incorporated by reference in their entirety for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

We claim:

1. A method of preserving visual function of an eye of a subject with an ocular condition selected from the group consisting of retinal detachment, age-related macular degeneration and retinitis pigmentosa, wherein a symptom of the ocular condition is the loss of photoreceptor cell viability in the retina of the eye with the condition, the method comprising:
 (a) administering to the eye of the subject an effective amount of a necrostatin and an effective amount of an apoptosis inhibitor selected from the group consisting of a pan-caspase inhibitor, a caspase-1 inhibitor, a caspase-3 inhibitor, a caspase-8 inhibitor, and a caspase-9 inhibitor thereby to preserve the viability of photoreceptor cells disposed within the retina of the eye; and
 (b) after step (a), measuring visual function of the eye; wherein the necrostatin is selected from the group consisting of:
 (i) a Nec-1 related compound of Formula I:

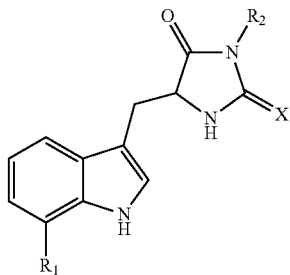

(I)

or a pharmaceutically acceptable salt, ester, or prodrug thereof, wherein
X is O or S;
$R_1$ is hydrogen, $C_1$-$C_6$alkyl, $C_1$-$C_6$ alkoxyl, or halogen; and
$R_2$ is hydrogen or $C_1$-$C_6$alkyl;
(ii) a Nec-1 related compound of Formula I-A:

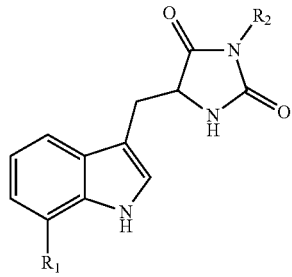

or a pharmaceutically acceptable salt, ester, or prodrug thereof,
wherein $R_1$ is H, alkyl, alkoxyl, or a halogen and $R_2$ is H or an alkyl;
(iii) a Nec-1 related compound of Formula I-B:

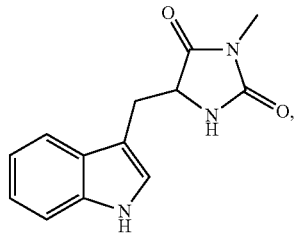 [SMILES: CN1C(=O)NC(Cc2c[nH]c3ccccc23)C1=O]

or a pharmaceutically acceptable salt, ester, or prodrug thereof;
(iv) a Nec-1 related compound of Formula I-C

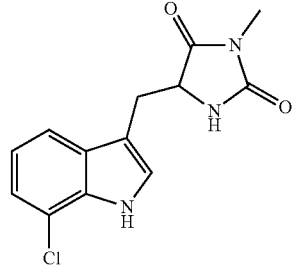 [SMILES: CN1C(=O)NC(Cc2c[nH]c3c(Cl)cccc23)C1=O]

or a pharmaceutically acceptable salt, ester, or prodrug thereof;
(v) a Nec-1 related compound of Formula I-D

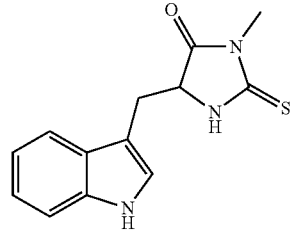 [SMILES: CN1C(=O)C(Cc2c[nH]c3ccccc23)NC1=S]

or a pharmaceutically acceptable salt thereof;

(vi) a Nec-1 related compound of Formula I-E:

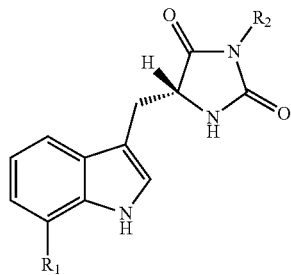

or a pharmaceutically acceptable salt, ester, or prodrug thereof,
wherein $R_1$ is H, alkyl, alkoxyl, or a halogen and $R_2$ is H or an alkyl;

(vii) a Nec-2 related compound of Formula II:

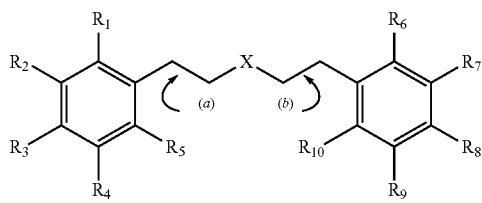

or a pharmaceutically acceptable salt, ester, or prodrug thereof, wherein:
X is —$CH_2$—, —$C(H)(R_{14})$—, —$C(=S)$—, —$C(=NH)$—, or —$C(O)$—;
$R_1$, $R_2$, $R_3$, $R_4$, $R_5$, $R_6$, $R_7$, $R_8$, $R_9$, and $R_{10}$ each represent independently hydrogen, acyl, acetyl, alkyl, halogen, amino, $C_1$-$C_6$alkoxyl, nitro, —$C(O)R_{12}$, —$C(S)R_{12}$, —$C(O)OR_{12}$, —$C(O)NR_{12}R_{13}$, —$C(S)NR_{12}R_{13}$, or —$S(O_2)R_{12}$;
$R_{11}$ is hydrogen, acyl, acetyl, alkyl, or acylamino;
$R_{12}$ and $R_{13}$ each represent independently hydrogen, an optionally substituted alkyl, an optionally substituted aryl, an optionally substituted heteroaryl, an optionally substituted aralkyl, or an optionally substituted heteroaralkyl;
$R_{14}$ is acyl, acetyl, alkyl, halogen, amino, acylamino, nitro, —$SR_{11}$, —$N(R_{11})_2$, or —$OR_{11}$;
the bond indicated by (a) can be a single or double bond; and
the bond indicated by (b) can be a single or double bond;

(viii) a Nec-2 related compound of Formula II-A:

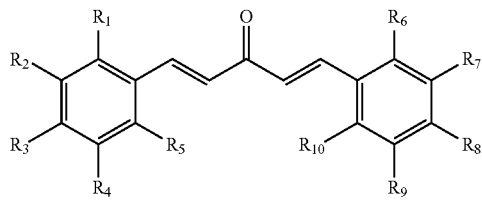

or a pharmaceutically acceptable salt thereof, wherein:
$R_1$, $R_2$, $R_5$, $R_6$, $R_7$, and $R_{10}$ each represent independently hydrogen, alkyl, halogen, amino, or methoxyl; and
$R_3$, $R_4$, $R_8$, and $R_9$ are $C_1$-$C_6$alkoxyl;

(ix) a Nec-3 related compound of Formula III:

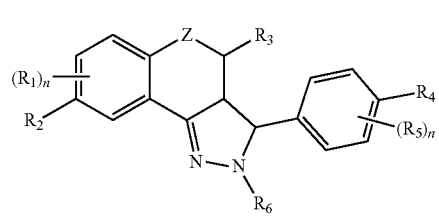

or a pharmaceutically acceptable salt, ester, or prodrug thereof, wherein:
Z is —$CH_2$—, —$CH_2CH_2$—, —O—, —S—, —S(O)—, —$S(O_2)$—, or —$N(R_7)$—;
$R_1$, $R_3$, and $R_5$ each represent independently for each occurrence hydrogen, halogen, hydroxyl, amino, $C_1$-$C_6$alkyl, $C_1$-$C_6$alkoxy, $C_1$-$C_6$alkoxy-$C_1$-$C_6$alkyl, $C_1$-$C_6$alkanoyl, $C_1$-$C_6$alkylsulfinyl, $C_1$-$C_6$alkylsulfonyl, $C_1$-$C_6$alkylsulfonyl-$C_1$-$C_6$alkyl, aryl, aralkyl, heterocycloalkyl, heteroaryl, or heteroaralkyl;
$R_2$ and $R_4$ are $C_1$-$C_6$alkoxy;
$R_6$ is —$C(O)R_8$, —$C(S)R_8$, —$C(O)OR_8$, —$C(O)NR_8R_9$, —$C(S)NR_8R_9$, —$C(NH)R_8$, or —$S(O_2)R_8$;
$R_7$ is alkyl, aralkyl, or heteroaralkyl;
$R_8$ and $R_9$ each represent independently hydrogen, $C_1$-$C_6$alkyl, heteroalkyl, aryl, heteroaryl, aralkyl, or heteroaralkyl; and
n represents independently for each occurrence 0, 1, or 2;

(x) a Nec-4 related compound of Formula IV:

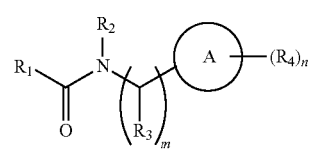

or a pharmaceutically acceptable salt, ester, or prodrug thereof, wherein:
$R_1$ is

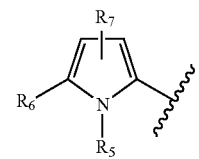

or

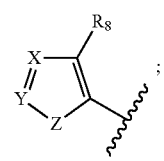

;

$R_2$ and $R_3$ each represent independently for each occurrence hydrogen or methyl;
$R_4$ represents independently for each occurrence halogen, hydrogen, $C_1$-$C_6$alkyl, $C_2$-$C_6$alkenyl, or $C_2$-$C_4$alkynyl;

$R_5$ is $C_1$-$C_4$alkyl;
$R_6$ is hydrogen, halogen, or —CN;
$R_7$ is hydrogen or $C_1$-$C_4$alkyl;
$R_8$ is $C_1$-$C_6$alkyl, or $R_8$ taken together with $R_9$, when present, forms a carbocyclic ring;
$R_9$ is hydrogen or $C_1$-$C_6$alkyl, or $R_9$ taken together with $R_8$ forms a carbocyclic ring;
$R_{10}$ is hydrogen or $C_1$-$C_6$alkyl;
A is phenylene or a 5-6 membered heteroarylene;
X is N or —C($R_9$)—;
Y is N or —C($R_{10}$)—;
Z is S or O; and
m and n each represent independently 1, 2, or 3;
(xi) a Nec-5 related compound of Formula V:

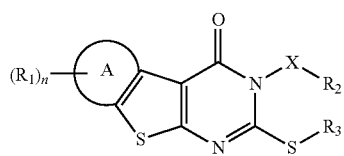
(V)

or a pharmaceutically acceptable salt, ester, or prodrug thereof, wherein:
A is a saturated or unsaturated 5-6 membered carbocyclic ring;
X is a bond or $C_1$-$C_4$alkylene;
$R_1$ is $C_1$-$C_6$ alkyl, halogen, hydroxyl, $C_1$-$C_6$alkoxyl, —N($R_4$)$_2$, —C(O)$R_4$, $CO_2R_4$, or C(O)N($R_4$)$_2$;
$R_2$ is

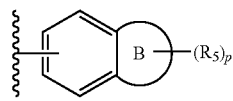

or

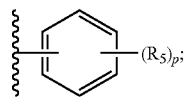

$R_3$ is —$C_1$-$C_6$alkylene-CN, —CN, $C_1$-$C_6$alkyl, or $C_2$-$C_6$alkenyl;
$R_4$ represents independently for each occurrence hydrogen, $C_1$-$C_6$alkyl, aryl, or aralkyl;
$R_5$ represents independently for each occurrence $C_1$-$C_6$alkyl, halogen, hydroxyl, $C_1$-$C_6$alkoxyl, —N($R_4$)$_2$, —C(O)$R_4$, $CO_2R_4$, or C(O)N($R_4$)$_2$;
B is a 5-6 membered heterocyclic or carbocylic ring; and
n and p each represent independently 0, 1, or 2;
(xii) a Nec-5 related compound of Formula V-A:

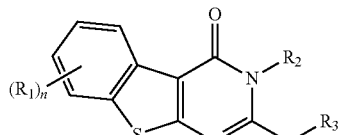
(V-A)

or a pharmaceutically acceptable salt, ester, or prodrug thereof, wherein:
$R_1$ is $C_1$-$C_6$alkyl, halogen, hydroxyl, $C_1$-$C_6$alkoxyl, or —N($R_4$)$_2$;
$R_2$ is

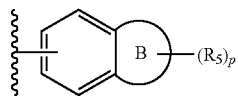

or

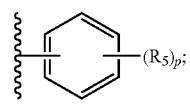

$R_3$ is —$C_1$-$C_6$alkylene-CN;
$R_4$ represents independently for each occurrence hydrogen, $C_1$-$C_6$alkyl, aryl, or aralkyl;
$R_5$ represents independently for each occurrence $C_1$-$C_6$alkyl, halogen, hydroxyl, $C_1$-$C_6$alkoxyl, —N($R_4$)$_2$, —C(O)$R_4$, $CO_2R_4$, or C(O)N($R_4$)$_2$;
B is a 5-6 membered heterocyclic or carbocylic ring; and
n and p each represent independently 0, 1, or 2;
(xiii) a Nec-7 related compound of Formula VII:

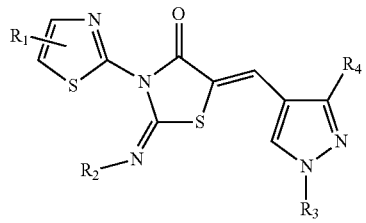
(VII)

or a pharmaceutically acceptable salt, ester, or prodrug thereof, wherein:
$R_1$, $R_2$ and $R_3$ each represent independently hydrogen or $C_1$-$C_4$alkyl;
$R_4$ is

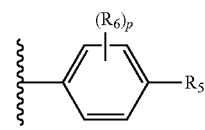

or

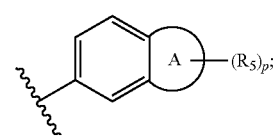

$R_5$ and $R_6$ each represent independently for each occurrence halogen, $C_1$-$C_6$alkyl, hydroxyl, $C_1$-$C_6$alkoxyl, —N($R_7$)$_2$, —NO$_2$, —S—$C_1$-$C_6$alkyl, —S-aryl, —SO$_2$—C$_1$-C$_6$alkyl, —SO$_2$-aryl, —C(O)R$_7$, —CO$_2$R$_7$, —C(O)N(R$_7$)$_2$, heterocycloalkyl, aryl, or heteroaryl;

R$_7$ represents independently for each occurrence hydrogen, C$_1$-C$_6$alkyl, aryl, or aralkyl; or two occurrences of R$_7$ attached to the same nitrogen atom are taken together with the nitrogen atom to which they are attached to form a 3-7 membered heterocyclic ring;

A is a 5-6 membered heterocyclic ring; and p is 0, 1, or 2;

(xiv) a Nec-7 related compound of Formula VIII:

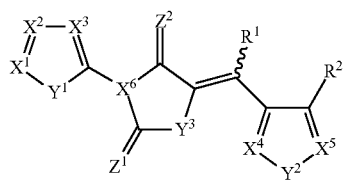

(VIII)

or a pharmaceutically acceptable salt, ester, or prodrug thereof, wherein:

each X$^1$, X$^2$, X$^3$, X$^4$, X$^5$, and X$^6$ is selected, independently, from N or CR$^{X1}$;

each Y$^1$, Y$^2$, and Y$^3$ is selected, independently, from O, S, NR$^{Y1}$, or CR$^{Y2}$R$^{Y3}$;

each Z$^1$ and Z$^2$ is selected, independently, from O, S, or NR$^{Z1}$;

each R$^{Y1}$ and R$^{Z1}$ is selected, independently, from H, optionally substituted C$_{1-6}$alkyl, optionally substituted C$_{2-6}$alkenyl, optionally substituted C$_{2-6}$alkynyl, optionally substituted cycloalkyl, optionally substituted heterocyclyl, optionally substituted aryl, optionally substituted heteroaryl, —C(=O)R$^{5A}$, —C(=O)OR$^{5A}$, or —C(=O)NR$^{5A}$R$^{6A}$;

each R$^{X1}$, R$^{Y2}$, and R$^{Y3}$ is selected, independently, from H, halogen, CN, NC, NO$_2$, N$_3$, OR$^3$, SR$^3$, NR$^3$R$^4$, —C(=O)R$^{5A}$, —C(=O)OR$^{5A}$, —C(=O)NR$^{5A}$R$^{6A}$, —S(=O)$_2$R$^{5A}$, —S(=O)$_2$R$^{5A}$, —S(=O)$_2$OR$^{5A}$, —S(=O)$_2$NR$^{5A}$R$^{6A}$, optionally substituted C$_{1-6}$alkyl, optionally substituted C$_{2-6}$alkenyl, optionally substituted C$_{2-6}$alkynyl, optionally substituted cycloalkyl, optionally substituted heterocyclyl, optionally substituted aryl, or optionally substituted heteroaryl;

each R$^1$, R$^2$, R$^{5A}$, R$^{5B}$, R$^{6A}$, and R$^{6B}$ is selected from H, optionally substituted C$_{1-6}$ alkyl, optionally substituted C$_{2-6}$alkenyl, optionally substituted C$_{2-6}$alkynyl, optionally substituted cycloalkyl, optionally substituted heterocyclyl, optionally substituted aryl, or optionally substituted heteroaryl; or R$^{5A}$ and R$^{6A}$, or R$^{5B}$ and R$^{6B}$ combine to form a heterocyclyl; and each R$^3$ and R$^4$ is selected from H, optionally substituted C$_{1-6}$ alkyl, optionally substituted cycloalkyl, optionally substituted heterocyclyl, optionally substituted aryl, optionally substituted heteroaryl, —C(=O)R$^{5B}$, —C(=S)R$^{5B}$, —C(=NR$^{6B}$)R$^{5B}$, —C(=O)OR$^{5B}$, —C(=O)NR$^{5B}$R$^{6B}$, —S(=O)R$^{5B}$, —S(=O)$_2$R$^{5B}$, —S(=O)$_2$OR$^{5B}$, or —S(=O)$_2$NR$^{5B}$R$^{6B}$; and (xv) a Nec-4 related compound of Formula IX:

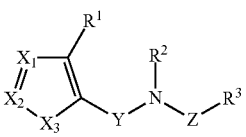

(IX)

or a pharmaceutically acceptable salt, ester, or prodrug thereof, wherein:

X$_1$ and X$_2$ are, independently, N or CR$^4$;

X$_3$ is selected from O, S, NR$^5$, or —(CR$_5$)$_2$;

Y is selected from C(O) or CH$_2$; and

Z is (CR$^6$R$^7$)$_n$;

R$^1$ is selected from H, halogen, optionally substituted C$_{1-6}$alkyl, or optionally substituted C$_{1-6}$cycloalkyl, or optionally substituted aryl;

R$^2$ is selected from H or optionally substituted C$_{1-6}$alkyl;

R$^3$ is optionally substituted aryl;

each R$^4$ is selected from H, halogen, carboxamido, nitro, cyano, optionally substituted C$_{1-6}$alkyl, or optionally substituted aryl;

R$^5$ is selected from H, halogen, optionally substituted C$_{1-6}$alkyl, or optionally substituted aryl;

each R$^6$ and R$^7$ is, independently, selected from H, optionally substituted C$_{1-6}$alkyl, or aryl; and n is 0, 1, 2, or 3.

2. The method of claim 1, wherein, after administration of the necrostatin and the apoptosis inhibitor, the visual function of the eye is preserved or improved relative to the visual function prior to administration of the necrostatin and the apoptosis inhibitor.

3. The method od claim 2, wherein the visual function is visual acuity.

4. The method of claim 1, wherein the necrostatin is selected from the group consisting of necrostatin-1, necrostatin-2, necrostatin-3, necrostatin-4, necrostatin-5, and necrostatin-7, or a combination thereof.

5. The method of claim 1, wherein the necrostatin is administered to provide a final concentration of necrostatin in the eye greater than about 100 μM.

6. The method of claim 1, wherein from about 0.05 mg to about 2 mg of necrostatin is administered.

7. The method of claim 1, wherein the apoptosis inhibitor is a pan-caspase inhibitor.

8. The method of claim 7, wherein the pan-caspase inhibitor is zVAD, IDN-6556 or a combination thereof.

9. The method of claim 7, wherein the pan-caspase inhibitor is administered to provide a final concentration in the eye greater than about 100 μM.

10. The method of claim 1, wherein the necrostatin, the apoptosis inhibitor, or both the necrostatin and the apoptosis inhibitor are administered to the eye.

11. The method of claim 1, wherein the necrostatin, the apoptosis inhibitor, or both the necrostatin and the apoptosis inhibitor are administered systemically.

12. The method of claim 1, wherein, when the ocular condition is a retinal detachment, the necrostatin and/or the apoptosis inhibitor is administered to the subject prior to reattachment of the retina or a region of the retina that has detached.

13. The method of claim 1, wherein, when the ocular condition is a retinal detachment, the necrostatin and/or the apoptosis inhibitor is administered to the subject after reattachment of the retina or a region of the retina that has detached.

14. A method of preserving the viability of photoreceptor cells disposed within a retina of a mammalian eye following retinal detachment, the method comprising:
administering a necrostatin and an apoptosis inhibitor selected from the group consisting of a pan-caspase inhibitor, a caspase-1 inhibitor, a caspase-3 inhibitor, a caspase-8 inhibitor, and a caspase-9 inhibitor to the eye in which a region of the retina has been detached in amounts sufficient to preserve the viability of photoreceptor cells disposed within the region of the detached retina, provided that, when necrostatin-1 is the only necrostatin administered, the region is exposed to a final concentration of necrostatin-1 in the eye greater than about 100 µM;
wherein the necrostatin is selected from the group consisting of:
(i) a Nec-1 related compound of Formula I:

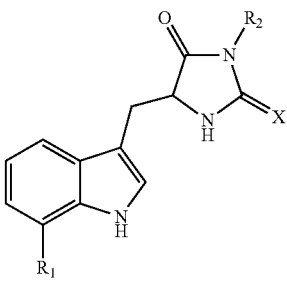

(I)

or a pharmaceutically acceptable salt, ester, or prodrug thereof, wherein
X is O or S,
$R_1$ is hydrogen, $C_1$-$C_6$ alkyl, $C_1$-$C_6$ alkoxyl, or halogen; and
$R_2$ is hydrogen or $C_1$-$C_6$ alkyl;
(ii) a Nec-1 related compound of Formula I-A:

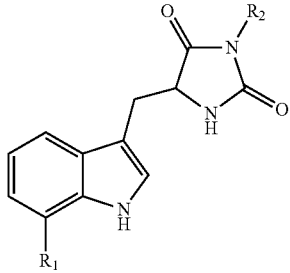

or a pharmaceutically acceptable salt, ester, or prodrug thereof,
wherein $R_1$ is H, alkyl, alkoxyl, or a halogen is H or an alkyl;
(iii) a Nec-1 related compound of Formula I-B:

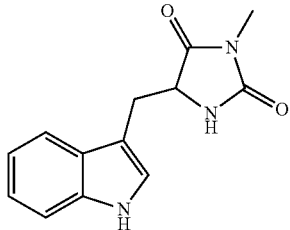 [SMILES: CN1C(=O)NC(Cc2c[nH]c3ccccc23)C1=O]

or a pharmaceutically acceptable salt, ester, or prodrug thereof;

(iv) a Nec-1 related compound of Formula I-C

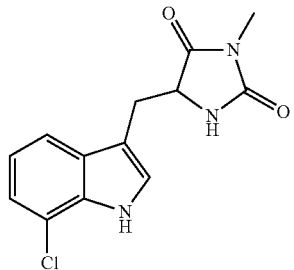 [SMILES: CN1C(=O)NC(Cc2c[nH]c3c(Cl)cccc23)C1=O]

or a pharmaceutically acceptable salt, ester, or prodrug thereof;
(v) a Nec-1 related compound of Formula I-D

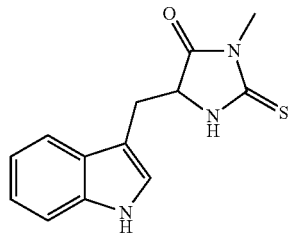 [SMILES: CN1C(=O)C(Cc2c[nH]c3ccccc23)NC1=S]

or a pharmaceutically acceptable salt thereof;
(vi) a Nec-1 related compound of Formula I-E:

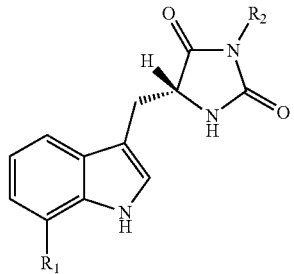

or a pharmaceutically acceptable salt, ester, or prodrug thereof,
wherein $R_1$ is H, alkyl, alkoxyl, or a halogen and $R_2$ is H or an alkyl;
(vii) a Nec-2 related compound of Formula II:

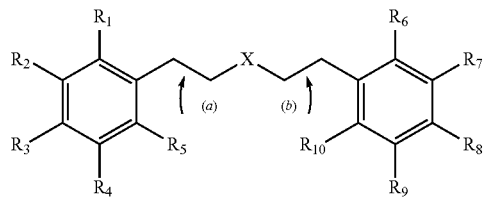

(II)

or a pharmaceutically acceptable salt, ester, or prodrug thereof, wherein:
X is —$CH_2$—, —C(H)($R_{14}$)—, —C(=S)—, —C(=NH)—, or —C(O)—;
$R_1$, $R_2$, $R_3$, $R_4$, $R_5$, $R_6$, $R_7$, $R_8$, $R_9$, and $R_{10}$ each represent independently hydrogen, acyl, acetyl, alkyl, halogen, amino, $C_1$-$C_6$ alkoxyl, nitro, —C(O)$R_{12}$, —C(S)$R_{12}$, —C(O)O$R_{12}$, —C(O)N$R_{12}R_{13}$, —C(S)N$R_{12}R_{13}$, or —S($O_2$)$R_{12}$;

R₁₁ is hydrogen, acyl, acetyl, alkyl, or acylamino;

R₁₂ and R₁₃ each represent independently hydrogen, an optionally substituted alkyl, an optionally substituted aryl, an optionally substituted heteroaryl, an optionally substituted aralkyl, or an optionally substituted heteroaralkyl;

R₁₄ is acyl, acetyl, alkyl, halogen, amino, acylamino, nitro, —SR₁₁, —N(R₁₁)₂, or —OR₁₁;

the bond indicated by (a) can be a single or double bond; and the bond indicated by (b) can be a single or double bond;

(viii) a Nec-2 related compound of Formula II-A:

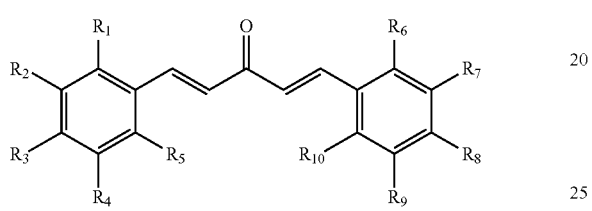

(II-A)

or a pharmaceutically acceptable salt thereof, wherein:

R₁, R₂, R₅, R₆, R₇, and R₁₀ each represent independently hydrogen, alkyl, halogen, amino, or methoxyl; and R₃, R₄, R₈, and R₉ are C₁-C₆alkoxyl;

(ix) a Nec-3 related compound of Formula III:

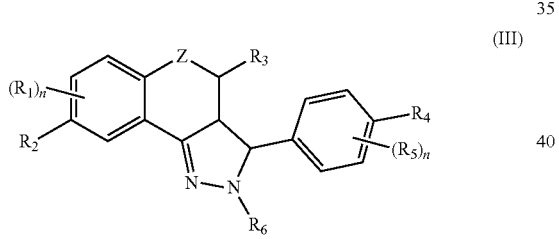

(III)

or a pharmaceutically acceptable salt, ester, or prodrug thereof, wherein:

Z is —CH₂—, —CH₂CH₂—, —O—, —S—, —S(O)—, —S(O₂)—, or —N(R₇)—;

R₁, R₃, and R₅ each represent independently for each occurrence hydrogen, halogen, hydroxyl, amino, C₁-C₆alkyl, C₁-C₆alkoxy, C₁-C₆alkoxy-C₁-C₆alkyl, C₁-C₆alkanoyl, C₁-C₆alkylsulfinyl, C₁-C₆alkylsulfinyl-C₁-C₆alkyl, C₁-C₆alkylsulfonyl, C₁-C₆alkylsulfonyl-C₁-C₆alkyl, aryl, aralkyl, heterocycloalkyl, heteroaryl, or heteroaralkyl;

R₂ and R₄ are C₁-C₆alkoxy;

R₆ is —C(O)R₈, —C(S)R₈, —C(O)OR₈, —C(O)NR₈R₉, —C(S)NR₈R₉, —C(NH)R₈, or —S(O₂)R₈;

R₇ is alkyl, aralkyl, or heteroaralkyl;

R₈ and R₉ each represent independently hydrogen, C₁-C₆alkyl, heteroalkyl, aryl, heteroaryl, aralkyl, or heteroaralkyl; and n represents independently for each occurrence 0, 1, or 2;

(x) a Nec-4 related compound of Formula IV:

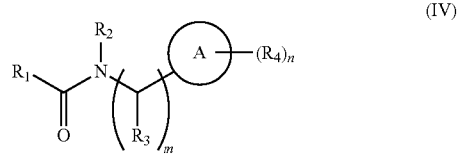

(IV)

or a pharmaceutically acceptable salt, ester, or prodrug thereof, wherein:

R₁ is

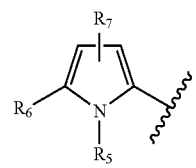

or

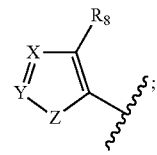

;

R₂ and R₃ each represent independently for each occurrence hydrogen or methyl;

R₄ represents independently for each occurrence halogen, hydrogen, C₁-C₆alkyl, C₂-C₆alkenyl, or C₂-C₄alkynyl;

R₅ is C₁-C₄alkyl;

R₆ is hydrogen, halogen, or —CN,

R₇ is hydrogen or C₁-C₄alkyl;

R₈ is C₁-C₆alkyl, or R₈ taken together with R₉, when present, forms a carbocyclic rind;

R₉ is hydrogen or C₁-C₆alkyl, or R₉ taken together with R₈ forms a carbocyclic ring;

R₁₀ is hydrogen or C₁-C₆alkyl;

A is phenylene or a 5-6 membered heteroarylene;

X is N or —C(R₉)—;

Y is N or —C(R₁₀)—;

Z is S or O; and m and n each represent independently 1, 2, or 3;

(xi) a Nec-5 related compound of Formula V:

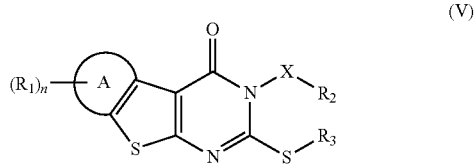

(V)

or a pharmaceutically acceptable salt, ester, or prodrug thereof, wherein:

A is a saturated or unsaturated 5-6 membered carbocyclic ring;

X is a bond or C₁-C₄alkylene;

$R_1$ is $C_1$-$C_6$ alkyl, halogen, hydroxyl, $C_1$-$C_6$alkoxyl, —N($R_4$)$_2$, —C(O)$R_4$, CO$_2R_4$, or C(O)N($R_4$)$_2$;

$R_2$ is

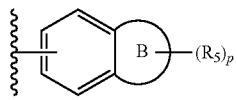

or

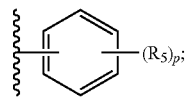

$R_3$ is —$C_1$-$C_6$alkylene-CN, —CN, $C_1$-$C_6$alkyl, or $C_2$-$C_6$alkenyl;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —N($R_4$)$_2$, —C(O)$R_4$, CO$_2R_4$, or C(O)N($R_4$)$_2$;

B is a 5-6 membered heterocyclic or carbocyclic ring; and n and p each represent independently 0, 1, or 2;

(xii) a Nec-5 related compound of Formula V-A:

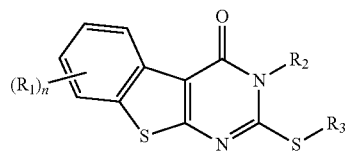

or a pharmaceutically acceptable salt, ester, or prodrug thereof, wherein:

$R_1$ is $C_1$-$C_6$alkyl, halogen, hydroxyl, $C_1$-$C_6$alkoxyl, or —N($R_4$)$_2$;

$R_2$ is

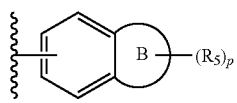

or

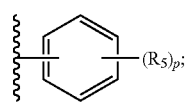

$R_3$ is —$C_1$-$C_6$alkylene-CN;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —N($R_4$)$_2$, —C(O)$R_4$, CO$_2R_4$, or C(O)N($R_4$)$_2$;

B is a 5-6 membered heterocyclic or carbocyclic ring; and n and p each represent independently 0, 1, or 2;

(xiii) a Nec-7 related compound of Formula VII:

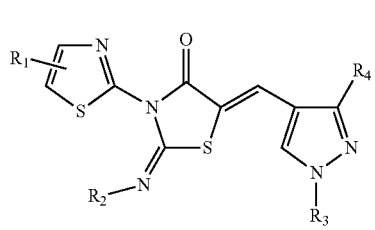

or a pharmaceutically acceptable salt, ester, or prodrug thereof, wherein:

$R_1$, $R_2$, and $R_3$ each represent independently hydrogen or $C_1$-$C_4$alkyl;

$R_4$ is

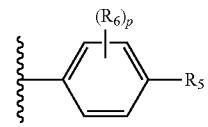

or

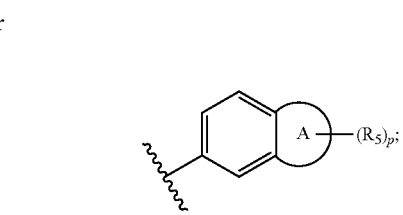

$R_5$ and $R_6$ each represent independently for each occurrence halogen, $C_1$-$C_6$alkyl, hydroxyl, $C_1$-$C_6$alkoxyl, —N($R_7$)$_2$, —NO$_2$, —S—$C_1$-$C_6$alkyl, —S-aryl, —SO$_2$—$C_1$-$C_6$alkyl, —SO$_2$-aryl, —C(O)$R_7$, —CO$_2R_7$, —C(O)N($R_7$)$_2$, heterocycloalkyl, aryl, or heteroaryl;

$R_7$ represents independently for each occurrence hydrogen, $C_1$-$C_6$alkyl, aryl, or aralkyl; or two occurrences of $R_7$ attached to the same nitrogen atom are taken together with the nitrogen atom to which they are attached to form a 3-7 membered heterocyclic ring;

A is a 5-6 membered heterocyclic ring; and p is 0, 1, or 2;

(xiv) a Nec-7 related compound of Formula VIII:

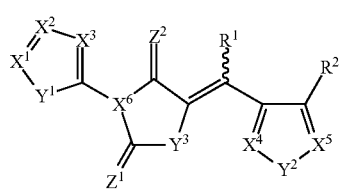

or a pharmaceutically acceptable salt, ester, or prodrug thereof, wherein:

each $X^1$, $X^2$, $X^3$, $X^4$, $X^5$, and $X^6$ is selected, independently, from N or CR$^{X1}$;

each $Y^1$, $Y^2$, and $Y^3$ is selected, independently, from O, S, NR$^{Y1}$, or CR$^{Y2}$R$^{Y3}$;

each $Z^1$ and $Z^2$ is selected, independently, from O, S, or $NR^{Z1}$;

each $R^{Y1}$ and $R^{Z1}$ is selected, independently, from H, optionally substituted $C_{1-6}$alkyl, optionally substituted $C_{2-6}$alkenyl, optionally substituted $C_{1-6}$alkynyl, optionally substituted cycloalkyl, optionally substituted heterocyclyl, optionally substituted aryl, optionally substituted heteroaryl, —C(=O)$R^{5A}$, —C(=O)O$R^{5A}$, or —C(=O)N$R^{5A}R^{6A}$;

each $R^{X1}$, $R^{Y2}$, and $R^{Y3}$ is selected, independently, from H, halogen, CN, NC, $NO_2$, $N_3$, $OR^3$, $SR^3$, $NR^3R^4$, —C(=O)$R^{5A}$, —C(=O)O$R^{5A}$, —C(=O)N$R^{5A}R^{6A}$, —S(=O)$R^{5A}$, —S(=O)$_2R^{5A}$, —S(=O)$_2OR^{5A}$, —S(=O)$_2NR^{5A}R^{6A}$, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl;

each $R^1$, $R^2$, $R^{5A}$, $R^{5B}$, $R^{6A}$, and $R^{6B}$ is selected from H, optionally substituted $C_{1-6}$ alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl; or $R^{5A}$ and $R^{6A}$, or $R^{5B}$ and $R^{6B}$ combine to form a heterocyclyl; and each $R^3$ and $R^4$ is selected from H, optionally substituted $C_{1-6}$ alkyl, optionally substituted cycloalkyl, optionally substituted heterocyclyl, optionally substituted aryl, optionally substituted heteroaryl, —C(=O)$R^{5B}$, —C(=S)$R^{5B}$, —C(=N$R^{6B}$)$R^{5B}$, —C(=O)O$R^{5B}$, —C(=O)N$R^{5B}R^{6B}$, —S(=O)$R^{5B}$, —S(=O)$_2R^{5B}$, —S(=O)$_2OR^{5B}$, or —S(=O)$_2NR^{5B}R^{6B}$; and (xv) a Nec-4 related compound of Formula IX:

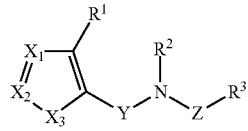

(IX)

or a pharmaceutically acceptable salt, ester, or prodrug thereof, wherein:

$X_1$ and $X_2$ are, independently, N or $CR^4$;

$X_3$ is selected from O, S, $NR^5$, or —$(CR^5)_2$;

Y is selected from C(O) or $CH_2$; and

Z is $(CR_6R_7)_n$;

$R^1$ is selected from H, halogen, optionally substituted $C_{1-6}$alkyl, or optionally substituted $C_{1-6}$cycloalkyl, or optionally substituted aryl;

$R^2$ is selected from H or optionally substituted $C_{1-6}$alkyl;

$R^3$ is optionally substituted aryl;

each $R^4$ is selected from H, halogen, carboxamido, nitro, cyano, optionally substituted $C_{1-6}$alkyl, or optionally substituted aryl;

$R^5$ is selected from H, halogen, optionally substituted $C_{1-6}$alkyl, or optionally substituted aryl;

each $R^6$ and $R^7$ is independently, selected from H, optionally substituted $C_{1-6}$alkyl, or aryl; and n is 0, 1, 2, or 3.

15. The method of claim 14, wherein the retinal detachment is a rhegmatogenous retinal detachment, a tractional retinal detachment, or a serous retinal detachment.

* * * * *

UNITED STATES PATENT AND TRADEMARK OFFICE
CERTIFICATE OF CORRECTION

PATENT NO. : 9,492,432 B2
APPLICATION NO. : 14/934810
DATED : November 15, 2016
INVENTOR(S) : Demetrios Vavvas et al.

It is certified that error appears in the above-identified patent and that said Letters Patent is hereby corrected as shown below:

In the Claims

Claim 1, Column 108, at Line 36, replace "Formula I-C" with --Formula I-C:--; and at Line 54, replace "Formula I-D" with --Formula I-D:--.

Claim 1, Column 110, at Line 20, insert --$C_1$-$C_6$alkylsulfinyl-$C_1$-$C_6$alkyl,-- after "$C_1$-$C_6$alkylsulfinyl,".

Claim 1, Column 111, at Line 30, replace "$C_1$-$C_6$ alkyl" with --$C_1$-$C_6$alkyl--; and at Line 55, replace "carbocylic" with --carbocyclic--.

Claim 1, Column 112, at Line 27, replace "carbocylic" with --carbocyclic--; and at Line 45, replace "$R_2$" with --$R_2$,--.

Claim 1, Column 113, at Line 47, replace the first instance of "-$S(=O)_2R^{5A}$" with -- -$S(=O)R^{5A}$--.

Claim 1, Column 114, at Line 14, replace "-$(CR_5)_2$" with -- -$(CR^5)_2$--.

Claim 3, Column 114, at Line 35, replace "od" with --of--.

Claim 14, Column 115, at Line 33, replace "S," with --S;--; at Line 52, insert --and R2-- directly after "halogen"; and at Line 65, insert --,-- directly after " 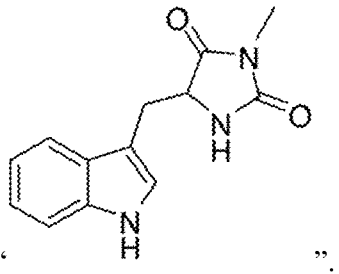 ".

Signed and Sealed this
Twenty-sixth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,492,432 B2

Claim 14, Column 117, at Line 52, replace "amino" with --amino,--.

Claim 14, Column 118, at Line 39, replace "-CN," with --CN--; and at Line 42, replace "rind" with --ring--.

Claim 14, Column 119, at Line 1, replace "$C_1$-$C_6$ alkyl" with --$C_1$-$C_6$alkyl--; and at Lines 26 and 66, replace "carbocylic" with --carbocyclic--.

Claim 14, Column 120, at Line 45, replace "nitro en atom are taken to ether" with --nitrogen atom are taken together--; and at Line 46, replace "nitro en" with --nitrogen--.

Claim 14, Column 121, at Line 5, replace "$C_{1-6}$alkynyl" with --$C_{2-6}$alkynyl--; and at Lines 21 and 28, replace "$C_1$-$C_6$ alkyl" with --$C_1$-$C_6$alkyl--.

Claim 14, Column 122, at Line 16, replace "$(CR_6R_7)_n$" with --$(CR^6R^7)_n$--; and at Line 26, replace "is" with --is,--.